US012600965B2

(12) United States Patent
Foster et al.

(10) Patent No.: US 12,600,965 B2
(45) Date of Patent: Apr. 14, 2026

(54) MODIFIED DOUBLE STRANDED OLIGONUCLEOTIDE

(71) Applicant: Alnylam Pharmaceuticals, Inc., Cambridge, MA (US)

(72) Inventors: Donald Foster, Cambridge, MA (US); Mark K. Schlegel, Cambridge, MA (US); Christopher Brown, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1179 days.

(21) Appl. No.: 17/291,775

(22) PCT Filed: Nov. 5, 2019

(86) PCT No.: PCT/US2019/059818

§ 371 (c)(1),
(2) Date: May 6, 2021

(87) PCT Pub. No.: WO2020/097044

PCT Pub. Date: May 14, 2020

(65) Prior Publication Data

US 2021/0388356 A1 Dec. 16, 2021

Related U.S. Application Data

(60) Provisional application No. 62/758,094, filed on Nov. 9, 2018.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/343* (2013.01); *C12N 2310/344* (2013.01)

(58) Field of Classification Search
CPC .............. C12N 15/113; C12N 2310/11; C12N 2310/315; C12N 2310/344
See application file for complete search history.

(56) References Cited

U.S. PATENT DOCUMENTS

| | | | |
|---|---|---|---|
| 11,260,134 | B2 | 3/2022 | Yokota et al. |
| 2012/0157509 | A1 | 6/2012 | Hadwiger et al. |
| 2018/0201929 | A1 | 7/2018 | Butler et al. |

FOREIGN PATENT DOCUMENTS

| | | | | |
|---|---|---|---|---|
| JP | 2017535552 | A | 11/2017 | |
| JP | 2017538679 | A | 12/2017 | |
| JP | 2018512155 | A | 5/2018 | |
| WO | 2013074974 | A2 | 5/2013 | |
| WO | 2013075035 | A1 | 5/2013 | |
| WO | 2013163430 | A2 | 10/2013 | |
| WO | 2014190157 | A1 | 11/2014 | |
| WO | 2015042564 | A1 | 3/2015 | |
| WO | 2015051318 | A1 | 4/2015 | |
| WO | WO-2016028649 | A1 * | 2/2016 | ........... A61K 31/713 |
| WO | 2016057893 | A1 | 4/2016 | |
| WO | 2016077321 | A1 | 5/2016 | |
| WO | 2016077349 | A1 | 5/2016 | |
| WO | 2016081444 | A1 | 5/2016 | |
| WO | 2016085852 | A1 | 6/2016 | |
| WO | 2016168286 | A1 | 10/2016 | |
| WO | 2017023660 | A1 | 2/2017 | |
| WO | 2017035340 | A1 | 3/2017 | |
| WO | 2018062510 | A1 | 4/2018 | |
| WO | 2018098117 | A1 | 5/2018 | |
| WO | 2018098328 | A1 | 5/2018 | |
| WO | 2018112320 | A1 | 6/2018 | |
| WO | 2018195165 | A1 | 10/2018 | |
| WO | 2019014530 | A1 | 1/2019 | |
| WO | 2019183164 | A1 | 9/2019 | |
| WO | 2020036862 | A1 | 2/2020 | |

OTHER PUBLICATIONS

Chiu et al., "siRNA function in RNAi: a chemical modification analysis." Rna 9.9: 1034-1048 (2003).
Elbashir et al., "Functional anatomy of siRNAs for mediating efficient RNAi in *Drosophila melanogaster* embryo lysate." The EMBO journal 20.23: 6877-6888 (2001).
UI-Tei et al., "Functional dissection of siRNA sequence by systematic DNA substitution: modifies siRNA with DNA seed arm is a powerful tool for mammalian gene silencing with significantly reduced off-target effect." Nucleic acids research 36.7 (2008): 2136-2151.

* cited by examiner

*Primary Examiner* — J. E. Angell
(74) *Attorney, Agent, or Firm* — Nixon Peabody LLP; David S. Resnick; Ravinderjit S. Braich

(57) ABSTRACT

One aspect of the present invention relates to double-stranded RNA (dsRNA) agent capable of inhibiting the expression of a target gene. Other aspects of the invention relate to pharmaceutical compositions comprising these dsRNA molecules suitable for therapeutic use, and methods of inhibiting the expression of a target gene by administering these dsRNA molecules, e.g., for the treatment of various disease conditions.

38 Claims, 6 Drawing Sheets

Specification includes a Sequence Listing.

MODIFIED DOUBLE STRANDED OLIGONUCLEOTIDE

CROSS-REFERENCE TO RELATED APPLICATION

This application is a 35 U.S.C. § 371 National Phase Entry Application of International Patent Application No. PCT/US2019/059818 filed on Nov. 5, 2019 which claims benefit under 35 U.S.C. § 119(e) of U.S. Provisional Application No. 62/758,094 filed Nov. 9, 2018, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 8, 2019, is named 051058-093750WOPT_SL.txt and is 315,843 bytes in size.

FIELD OF THE INVENTION

The invention relates to dsRNA molecules having particular motifs that are advantageous for inhibition of target gene expression, as well dsRNA agent compositions, suitable for therapeutic use. Additionally, the invention provides methods of inhibiting the expression of a target gene by administering these dsRNA agents, e.g., for the treatment of various diseases.

BACKGROUND

RNA interference or "RNAi" is a term initially coined by Fire and co-workers to describe the observation that double-stranded RNAi (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

There remains a need in the art for effective nucleotide or chemical motifs for dsRNA molecules, which are advantageous for inhibition of target gene expression. This invention is directed to that effort.

SUMMARY

This invention provides effective nucleotide or chemical motifs for dsRNA molecules, which are advantageous for inhibition of target gene expression, as well as RNAi compositions suitable for therapeutic use.

In one aspect the invention provides a double stranded RNA (dsRNA) molecule comprising a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 19 to 25 base pairs; wherein the dsRNA molecule comprises a ligand; and wherein the sense strand does not comprise a glycol nucleic acid (GNA).

It is understood that the antisense strand has sufficient complementarity to a target sequence to mediate RNA interference. In other words, the dsRNA molecules of the invention are capable of inhibiting the expression of a target gene.

In some embodiments, the dsRNA comprises at least three 2'-deoxy modifications, wherein the 2'-deoxy modifications are at positions 2 and 14 of the antisense strand, counting from 5'-end of the antisense strand, and at position 11 of the sense strand, counting from 5'-end of the sense strand.

In some embodiments, the dsRNA comprises at least five 2'-deoxy modifications, wherein the 2'-deoxy modifications are at positions 2, 12 and 14 of the antisense strand, counting from 5'-end of the antisense strand, and at positions 9 and 11 of the sense strand, counting from 5'-end of the sense strand.

In some embodiments, the dsRNA comprises at least seven 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand.

In some embodiments, the antisense strand comprises at least five 2'-deoxy modifications at positions 2, 5, 7, 12 and 14, counting from 5'-end of the antisense strand. In some further embodiments of this, the antisense strand has a length of 18-25 nucleotides, preferably, a length of 18-23 nucleotides.

In some embodiments, the dsRNA agent can comprise one or more non-natural nucleotides. For example, the dsRNA agent can comprise less than 20%, e.g., less than 15%, less than 10%, or less than 5% non-natural nucleotides, or the dsRNA comprises no non-natural nucleotides. For example, the dsRNA agent comprises all natural nucleotides. Some exemplary non-natural nucleotides include, but are not limited to, acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

Accordingly, in some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; wherein the sense strand does not comprise a glycol nucleic acid (GNA); and wherein the dsRNA comprises less than 20%, e.g., less than 15%, less than 10%, or less than 5% non-natural nucleotides or the dsRNA agent comprises all natural nucleotides.

In some embodiments, at least one the sense strand and the antisence comprises at least one, e.g., at least two, at least three, at least four, at least five, at least six, at least seven or more, 2'-deoxy modifications in a central region of the sense strand or the antisense strand. Accordingly, in some embodiments, the invention provides a dsRNA agent comprising a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; and wherein the sense strand and/or the antisense strand comprises at least one, e.g., at least two, at least three, at least four, at least five, at least six, at least seven or more, 2'-deoxy modifications in a central region of the sense strand and/or the antisense strand strand.

In some embodiment, the sense strand has length of 18 to 30 nucleotides and comprises at least two 2'-deoxy modifications in the central region of the sense strand. For example, the sense strand has length of 18 to 30 nucleotides and comprises at least two 2'-deoxy modifications within positions 7, 8, 9, 10, 11, 12, and 13, counting from 5'-end of the sense strand.

In some embodiments, the antisense strand has a length of 18 to 30 nucleotides and comprises at least two 2'-deoxy modifications in the central region of the antisense strand. For example, the antisense strand has length of 18 to 30 nucleotides and comprises at least two 2'-deoxy modifications within positions 10, 11, 12, 13, 14, 15 and 16, counting from 5'-end of the antisense strand.

In some embodiments, the invention provides a dsRNA agent comprising a sense strand and an antisense strand; wherein the sense strand has a length of 17-30 nucleotide and comprises at least one 2'-deoxy modification in the central region of the sense strand; wherein the antisense strand independently has a length of 17-30 nucleotides and comprises at least two 2'-deoxy modifications in the central region of the antisense strand.

In some embodiments, the invention provides a dsRNA agent comprising a sense strand and an antisense strand; wherein the sense strand has a length of 17-30 nucleotide and comprises at least two 2'-deoxy modifications in the central region of the sense strand; wherein the antisense strand independently has a length of 17-30 nucleotides and comprises at least one 2'-deoxy modification in the central region of the antisense strand.

In some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; and wherein the sense strand comprises at least one, e.g., at least two, at least three, at least four, at least five, at least six, at least seven or more, 2'-deoxy modifications in a central region of the sense strand strand.

In some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; and wherein the antisense strand comprises at least one, e.g., at least two, at least three, at least four, at least five, at least six, at least seven or more, 2'-deoxy modifications in a central region of the antisense strand strand.

In some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; wherein the dsRNA comprises less than 20%, e.g., less than 15%, less than 10%, or less than 5% non-natural nucleotides or the dsRNA agent comprises all natural nucleotides; and wherein the sense strand and/or the antisense strand comprises at least one, e.g., at least two, at least three, at least four, at least five, at least six, at least seven or more, 2'-deoxy modifications in a central region of the sense strand and/or the antisense strand strand.

In some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; wherein the dsRNA comprises less than 20%, e.g., less than 15%, less than 10%, or less than 5% non-natural nucleotides or the dsRNA agent comprises all natural nucleotides; and wherein the sense strand comprises at least one, e.g., at least two, at least three, at least four, at least five, at least six, at least seven or more, 2'-deoxy modifications in a central region of the sense strand.

In some embodiments, the dsRNA agent comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy nucleotides on the sense and/or antisense strands; and wherein the dsRNA molecule has a double stranded (duplex) region of between 19 to 25 base pairs; wherein the dsRNA molecule comprises a ligand; wherein the dsRNA comprises less than 20%, e.g., less than 15%, less than 10%, or less than 5% non-natural nucleotides or the dsRNA agent comprises all natural nucleotides; and wherein the antisense strand comprises at least one, e.g., at least two, at least three, at least four, at least five, at least six, at least seven or more, 2'-deoxy modifications in a central region of the antisense strand.

In some embodiments, when the dsRNA comprises less than 8 non-2'OMe nucleotides, the antisense stand comprises at least one DNA. For example, in any one of the embodiments of the invention when the dsRNA comprises less than 8 non-2'OMe nucleotides, the antisense stand comprises at least one DNA.

In some embodiments, when the antisense comprises two deoxy nucleotides and said nucleotides are at positions 2 and 14, counting from the 5'-end of the antisense strand, the dsRNA comprises 8 or less (e.g., 8, 7, 6, 5, 4, 3, 2, 1 or 0) non-2'OMe nucleotides. For example, in any one of the embodiments of the invention when the antisense comprises two deoxy nucleotides and said nucleotides are at positions 2 and 14, counting from the 5'-end of the antisense strand, the dsRNA comprises 0, 1, 2, 3, 4, 5, 6, 7 or 8 non 2'-OMe nucleotides.

In another aspect, the invention further provides a method for delivering the dsRNA molecule of the invention to a specific target in a subject by subcutaneous or intravenous administration. The invention further provides the dsRNA molecules of the invention for use in a method for delivering said agents to a specific target in a subject by subcutaneous or intravenous administration.

DETAILED DESCRIPTION

Figure 1:
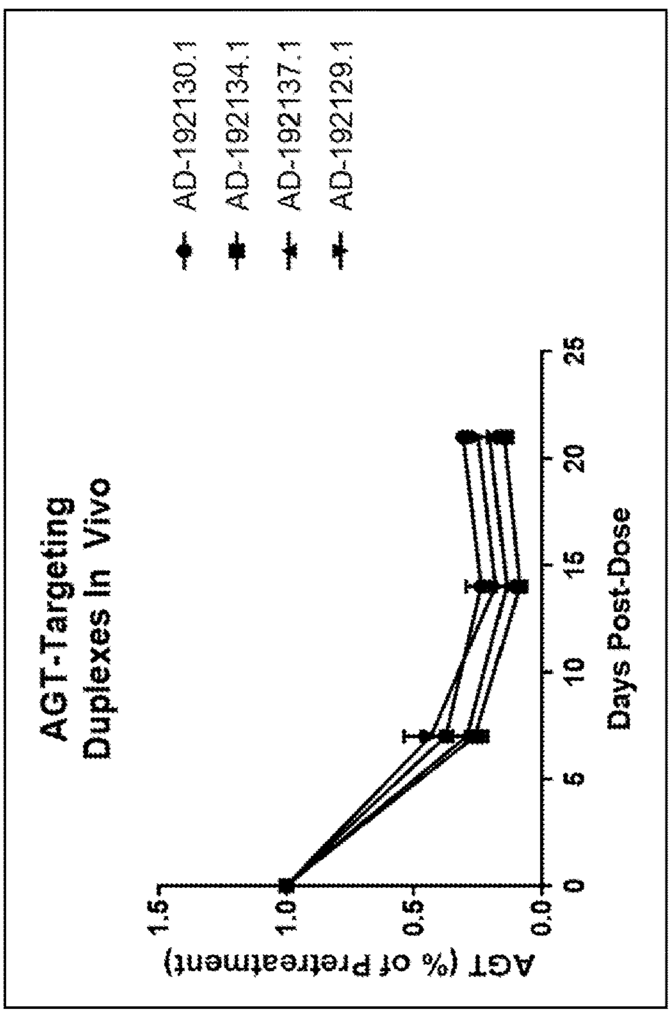
FIGS. 1-4 show in vivo efficacy of some exemplary dsRNAs of the invention in mice.

In one aspect, the invention provides a double-stranded RNA (dsRNA) agent capable of inhibiting expression of a target gene. Without limitations, the dsRNA agents of the invention can be substituted for the dsRNA molecules and can be used in RNA interference based gene silencing techniques, including, but not limited to, in vitro or in vivo applications.

Generally, the dsRNA molecule comprises a sense strand (also referred to as passenger strand) and an antisense strand (also referred to as guide strand). Each strand of the dsRNA molecule can range from 15-35 nucleotides in length. For example, each strand can be between, 17-35 nucleotides in length, 17-30 nucleotides in length, 25-35 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. Without limitations, the sense and antisense strands can be equal length or unequal length. For example, the sense strand and the antisense strand independently have a length of 18, 19, 20, 21, 22, 23, 24 or 25 nucleotides.

In some embodiments, the antisense strand is of length 15-35 nucleotides. In some embodiments, the antisense strand is 15-35, 17-35, 17-30, 25-35, 27-30, 17-23, 17-21, 17-19, 19-25, 19-23, 19-21, 21-25, 21-25, or 21-23 nucleotides in length. For example, the antisense strand can be 15, 16, 17, 18, 19, 20, 21, 22, 23, 24, 25, 26, 27, 28, 29, 30, 31, 32, 33, 34 or 35 nucleotides in length. In some embodiments, the antisense strand is 19, 20, 21, 22, 23, 24 or 25 nucleotides in length. In some particular embodiments, the antisense strand is 23 nucleotides in length.

Similar to the antisense strand, the sense strand can be, in some embodiments, 15-35 nucleotides in length. In some embodiments, the sense strand is 15-35, 17-35, 17-30, 25-35, 27-30, 17-23, 17-21, 17-19, 19-25, 19-23, 19-21, 21-25, 21-25, or 21-23 nucleotides in length. For example, the sense strand can be 15, 16, 17, 18, 19, 20, 21, 22, 23, 24, 25, 26, 27, 28, 29, 30, 31, 32, 33, 34 or 35 nucleotides in length. In some embodiments, the sense strand is 17, 18, 19, 20, 21, 22, 23, 24 or 25 nucleotides in length. In some particular embodiments, the sense strand is 21 nucleotides in length.

In some embodiments, the sense strand can be 15-35 nucleotides in length, and the antisense strand can be independent from the sense strand, 15-35 nucleotides in length. In some embodiments, the sense strand is 15-35, 17-35, 17-30, 25-35, 27-30, 17-23, 17-21, 17-19, 19-25, 19-23, 19-21, 21-25, 21-25, or 21-23 nucleotides in length, and the antisense strand is independently 15-35, 17-35, 17-30, 25-35, 27-30, 17-23, 17-21, 17-19, 19-25, 19-23, 19-21, 21-25, 21-25, or 21-23 nucleotides in length. For example, the sense and the antisense strand can be independently 15, 16, 17, 18, 19, 20, 21, 22, 23, 24, 25, 26, 27, 28, 29, 30, 31, 32, 33, 34 or 35 nucleotides in length. In some embodiments, the sense strand and the antisense strand are independently 17, 18, 19, 20, 21, 22, 23, 24 or 25 nucleotides in length. In some particular embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; and wherein the sense strand does not comprise a glycol nucleic acid. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length.

The sense strand and antisense strand typically form a double-stranded or duplex region. Without limitations, the duplex region of a dsRNA agent described herein can be 12-35 nucleotide pairs in length. For example, the duplex region can be between 14-35 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length. In some preferred embodiments, the duplex region is 18, 19, 20, 21, 22, 23, 24 or 25 nucleotide pairs in length.

Thus, in some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; and wherein the sense strand does not comprise a glycol nucleic acid. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length.

As described herein, the dsRNA agent can comprise one or more non-natural nucleotides. For example, the dsRNA agent comprises no non-natural nucleotides or comprises less than 20%, e.g., less than 15%, less than 10%, or less than 5% non-natural nucleotides. For clarification, by a "natural nucleotide" is meant a 2'-deoxy, 2'-OH, or 2'-OMe nucleotide with a nucleobase selected from adenine, guanine, cytosine, uracil, and thymine. In other words, a natural nucleotide has nucleobase selected from adenine, guanine, cytosine, uracil, and thymine, and a sugar selected from a 2'-deoxy, 2'-OH, or 2'-OMe ribose. By a "non-natural nucleotide" is meant a nucleotide having a nucleobase other than adenine, guanine, cytosine, uracil, or thymine, and/or a sugar other than a 2'-deoxy, 2'-OH, or 2'-OMe ribose. For clarity, when a non-natural nucleotide has a 2'-deoxy, 2'-OH, or 2'-OMe ribose sugar, then the nucleobase is not adenine, guanine, cytosine, uracil, or thymine.

Exemplary nucleobases for the non-natural nucleotide include, but are not limited to, inosine, xanthine, hypoxanthine, nubularine, isoguanisine, tubercidine, and substituted or modified analogs of adenine, guanine, cytosine and uracil, such as 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyl adenine, N-methylguanines, or O-alkylated bases. Further purines and pyrimidines include those disclosed in U.S. Pat. No. 3,687,808, those disclosed in the Concise Encyclopedia of Polymer Science And Engineering, pages 858-859, Kroschwitz, J. I., ed. John Wiley & Sons, 1990, and those disclosed by Englisch et al., Angewandte Chemie, International Edition, 1991, 30, 613.

In some embodiments, nucleobase for the non-natural nucleotide is selected from the group consisting of inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl) adenine, 2-(methylthio)-$N^6$-(isopentenyl)adenine, 6-(alkyl) adenine, 6-(methyl)adenine, 7-(deaza)adenine, 8-(alkenyl) adenine, 8-(alkyl)adenine, 8-(alkynyl)adenine, 8-(amino) adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine,2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl) uracil, 5-(guanidiniumalkyl)uracil, 5-(1,3-diazole-1-alkyl) uracil, 5-(cyanoalkyl)uracil, 5-(dialkylaminoalkyl)uracil, 5-(dimethylaminoalkyl)uracil, 5-(halo)uracil, 5-(methoxy) uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil,4-(thio)pseudouracil,2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)i socarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, and any O-alkylated or N-alkylated derivatives thereof.

Some exemplary non-natural nucleotides include, but are not limited to, acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

Thus, in some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

Central Region

As described herein, the dsRNA can comprise at least one, e.g., at least two, at least three, at least four, at least five, at least six, at least seven or more, 2'-deoxy modifications in a central region of the sense strand and/or the antisense strand. As used herein, a "central region" of a strand refers to positions 5-17, e.g., positions 6-16, positions 6-15, positions 6-14, positions 6-13, positions 6-12, positions 7-15, positions 7-14, positions 7-13, positions, 7-12, positions 8-16, positions 8-15, positions 8-14, positions 8-13, positions 8-12, positions 9-16, positions 9-15, positions 9-14, positions 9-13, positions 9-12, positions 10-16, positions 10-15, positions 10-14, positions 10-13 or positions 10-12, counting from the 5'-end of the strand. For example, the central region of a strand means positions 5, 6, 7, 8, 9, 10, 11, 12, 13, 14, 15, 16 or 17 of the strand. A preferred central region for the sense strand is positions 6, 7, 8, 9, 10, 11, 12, 13, and 14, counting from the 5'-end of the sense strand. A more preferred central region for the sense strand is positions 7, 8, 9, 10, 11, 12 and 13, counting from the 5'-end of the sense strand. A preferred central region for the antisense strand is positions 9, 10, 11, 12, 13, 14, 15 16 and 17, counting from 5'-end of the antisense strand. A more preferred central region for the antisense strand is positions 10, 11, 12, 13, 14, 15 and 16, counting from 5'-end of the antisense strand.

Accordingly, at least one of the sense stand and the antisense can comprise at least one, e.g., at least two, at least three, at least four, at least five, at least six, at least seven or more, 2'-deoxy modification in positions 5-17, e.g., positions 6-16, positions 6-15, positions 6-14, positions 6-13, positions 6-12, positions 7-15, positions 7-14, positions 7-13, positions, 7-12, positions 8-16, positions 8-15, positions 8-14, positions 8-13, positions 8-12, positions 9-16, positions 9-15, positions 9-14, positions 9-13, positions 9-12, positions 10-16, positions 10-15, positions 10-14, positions 10-13 or positions 10-12, counting from the 5'-end of the sense strand or the antisense strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein the sense strand comprises at least two, e.g., at least three, at least four, at least five, at least six, at least seven or more, 2'-deoxy modifications in a central region of the sense strand. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the sense strand comprises at least one, e.g., at least two, at least three, at least four, at least five, at least six, at least seven or more, 2'-deoxy modifications in a central region of the sense strand. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the sense comprises at least one, e.g., at least two, at least three, at least four, at least five, at least six, at least seven or more, 2'-deoxy modifications in a central region of the sense strand. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein the antisense strand comprises at least two, e.g., at least three, at least four, at least five, at least six, at least seven or more, 2'-deoxy modifications in a central region of the antisense strand. In some embodiments, the sense strand is 18-30 nucleotides in length and comprises at least two 2'-deoxy modifications in a central region, e.g., positions 10, 11, 12, 13, 14, 15, and 16 of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand. In some embodiments, the antisense strand is 18-30 nucleotides in length and comprises at least two 2'-deoxy modifications in a central region, e.g., positions 10, 11, 12, 13, 14, 15, and 16 of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense comprises at least one, e.g., at least two, at least three, at least four, at least five, at least six, at least seven or more, 2'-deoxy modifications in a central region of the antisense strand. In some embodiments, the antisense strand is 18-30 nucleotides in length and comprises at least two 2'-deoxy modifications in a central region, e.g., positions 10, 11, 12, 13, 14, 15 and 16 of the antisense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

The antisense strand comprises one at least one, e.g., at least two, at least three, at least four, at least five, at least six, at least seven or more, 2'-deoxy modifications in a central region of the antisense strand, and at least one, e.g., at least two, at least three, at least four, at least five, at least six, at least seven or more, 2'-deoxy modifications in a central region of the antisense strand As used herein, a "non-central region" means a region of a strand that is not a central region. For example, the non-central region can be a terminal region, e.g., 1, 2, 3, 4, 5 or 6 nucleotides from either end of the strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand, and at least one, e.g., at least two, at least three, at least four, at least five, at least six, at least seven or more, 2'-deoxy modifications in a central region of the antisense strand. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense comprises at least one, e.g., at least two, at least three, at least four, at least five, at least six, at least seven or more, 2'-deoxy modifications in a central region of the antisense strand. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the antisense strand comprises at least five 2'-deoxy modifications. For example, the antisense strand comprises at least five 2'-deoxy modifications and wherein the 2'-deoxy modifications are at positions 2, 5, 7, 12 and 14, counting from 5'-end of the antisense strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein the antisense strand comprises at least five, at least six, at least seven or more, 2'-deoxy modifications, e.g., at positions 2, 5, 7, 12 and 14, counting from 5-'end of the antisense strand. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein the antisense strand comprises at least five, at least six, at least seven or more, 2'-deoxy modifications, e.g., at positions 2, 5, 7, 12 and 14, counting from 5-'end of the antisense strand. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense strand comprises at least five, at least six, at least seven or more, 2'-deoxy modifications, e.g., at positions 2, 5, 7, 12 and 14, counting from 5-'end of the antisense strand. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises at least three 2'-deoxy modifications, wherein at least two of the 2'-deoxy modifications are in the antisense strand and at least one of the 2'-deoxy modification is in the sense strand. For example, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein at least two of the 2'-deoxy modifications are in the antisense strand, and at least one of the 2'-deoxy modification is in the sense strand. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein at least two of the 2'-deoxy modifications are in the antisense strand, and at least one of the 2'-deoxy modification is in the sense strand. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least two of the 2'-deoxy modifications are in the antisense strand, and at least one of the 2'-deoxy modification is in the sense strand. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises at least five 2'-deoxy modifications, wherein at least three of the 2'-deoxy modifications are in the antisense strand and at least two of the 2'-deoxy modifications are in the sense strand. For example, the antisense strand comprises at least three 2'-deoxy modifications and the sense strand comprises at least two 2'-deoxy modification, wherein the 2'-deoxy modifications are at positions 2, 12 and 14 of the antisense strand, counting from 5'-end of the antisense strand, and at positions 9 and 11 of the sense strand, counting from 5'-end of the sense strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein at least three of the 2'-deoxy modifications are in the antisense strand, and at least two of the 2'-deoxy modifications are in the sense strand. In some embodiments, the antisense strand comprises at least three 2'-deoxy modifications and the sense strand comprises at least two 2'-deoxy modification, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein at least three of the 2'-deoxy modifications are in the antisense strand, and at least two of the 2'-deoxy modifications are in the sense strand. In some embodiments, the antisense strand comprises at least three 2'-deoxy modifications and the sense strand comprises at least two 2'-deoxy modifications, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least three of the 2'-deoxy modifications are in the antisense strand, and at least two of the 2'-deoxy modifications are in the sense strand. In some embodiments, the antisense strand comprises at least three 2'-deoxy modifications and the sense strand comprises at least two 2'-deoxy modifications, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N- methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises at least seven 2'-deoxy modifications, wherein at least five of the 2'-deoxy modifications are in the antisense strand and at least two of the 2'-deoxy modification are in the sense strand. For example, the antisense strand comprises at least five 2'-deoxy modifications and the sense strand comprises at least two 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least seven 2'-deoxy modifications on the sense and/or antisense strands; wherein the dsRNA molecule has a double stranded (duplex) region of between 18 to 25 base pairs; wherein the dsRNA molecule comprises a ligand; wherein the sense strand does not comprise a glycol nucleic acid; and wherein at least five of the 2'-deoxy modifications are in the antisense strand, and at least two of the 2'-deoxy modification is in the sense strand. In some embodiments, the antisense strand comprises at least five 2'-deoxy modifications and the sense strand comprises at least two 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least seven 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; and wherein at least five of the 2'-deoxy modifications are in the antisense strand, and at least two of the 2'-deoxy modifications are in the sense strand. In some embodiments, the antisense strand comprises at least five 2'-deoxy modifications and the sense strand comprises at least two 2'-deoxy modification, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least five of the 2'-deoxy modifications are in the antisense strand, and at least two of the 2'-deoxy modifications are in the sense strand. In some embodiments, the antisense strand comprises at least five 2'-deoxy modifications and the sense strand comprises at least two 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

A wide variety of entities can be coupled to the dsRNA agents described herein. Preferred moieties are ligands, which are coupled, preferably covalently, either directly or indirectly via an intervening tether. Generally, a ligand alters the distribution, targeting or lifetime of the molecule, e.g., a dsRNA described herein, into which it is incorporated. In some embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands herein.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972, which is incorporated by reference in its entirety), the EALA peptide (Vogel et al., J. Am. Chem. Soc., 1996, 118: 1581-1586, which is incorporated by reference in its entirety), and their derivatives (Turk et al., Biochem. Biophys. Acta, 2002, 1559: 56-68, which is incorporated by reference in its entirety). In some embodiments, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and can also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases or a chelating agent (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptide species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, j aplakinolide, latrunculin A, phalloidin, swinholide A, indanocine, or myoservin.

The ligand can increase the uptake of the dsRNA into the cell by activating an inflammatory response, for example. Exemplary ligands that would have such an effect include tumor necrosis factor alpha (TNF-alpha), interleukin-1 beta, or gamma interferon.

In some embodiments, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In some embodiments, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or cross-linked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 1). An RFGF analogue (e.g., amino acid sequence AALLPVLLAAP (SEQ ID NO: 2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 3)) and the *Drosophila* Antennapedia protein (RQIKIWFQNRRMKWKK (SEQ ID NO: 4) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-94, 1991, which is incorporated by reference in its entirety). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002, which is incorporated by reference in its entirety). An RGD peptide can facilitate targeting of an iRNA agent to tumors of a variety of other tissues, including the lung, kidney, spleen, or liver (Aoki et al., Cancer Gene Therapy 8:783-787, 2001, which is incorporated by reference in its entirety). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha v\beta_3$ (Haubner et al., Jour. Nucl. Med., 42:326-336, 2001, which is incorporated by reference in its entirety). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003, which is incorporated by reference in its entirety).

In some embodiments, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number of helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; a, (3, or y peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the dsRNA at various places, for example, 3'-end, 5'-end, and/or at an internal position of the sense and/or antisense strand. In preferred embodiments, the ligand is attached to the sense and/or antisense strand of the dsRNA via a linker or tether. The ligand or tethered ligand can be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_nNH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

The ligands can be attached to one or both strands. In some embodiments, a dsRNA described herein comprises a ligand conjugated to the sense strand. In some embodiments, a dsRNA described herein comprises a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

In some embodiments, the ligand is conjugated to the sense strand. As described herein, the ligand can be conjugated at the 3'-end, 5'-end or at an internal position of the sense strand. In some embodiments, the ligand is conjugated to the 3'-end of the sense strand. Further, the ligand can be conjugated to a nucleobase, sugar moiety or internucleotide linkage of the sense strand.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more carbohydrates, e.g., GalNAc (N-acetylgalactosamine) derivatives attached through a monovalent, bivalent or trivalent branched linker.

In some embodiments, the dsRNA of the invention is conjugated to a bivalent and trivalent branched linkers include the structures shown in any of Formula (IV)-(VII):

Formula (IV)

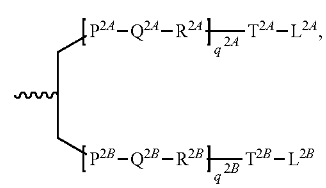

Formula (V)

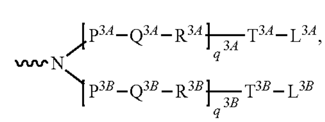

Formula (VI)

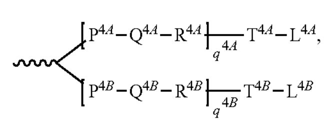

or

-continued

Formula (VII)

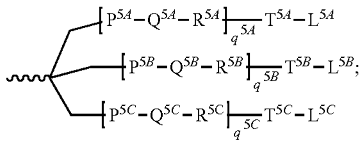

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')═C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH═N—O,

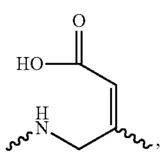,
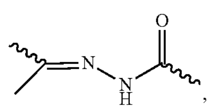,

-continued

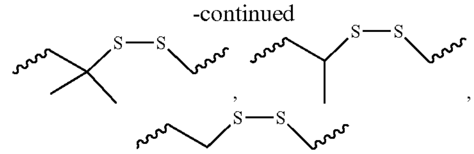

or heterocyclyl;

$L^{2A}$, $L^{2B}$, $L^{3A}$, $L^{3B}$, $L^{4A}$, $L^{4B}$, $L^{5A}$, $L^{5B}$, $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with dsRNA agents described herein for inhibiting the expression of a target gene, such as those of Formula (VII):

Formula (VII)

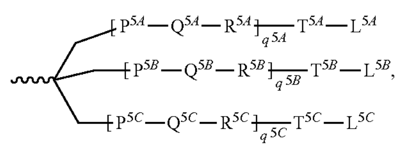

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

Ligand 1

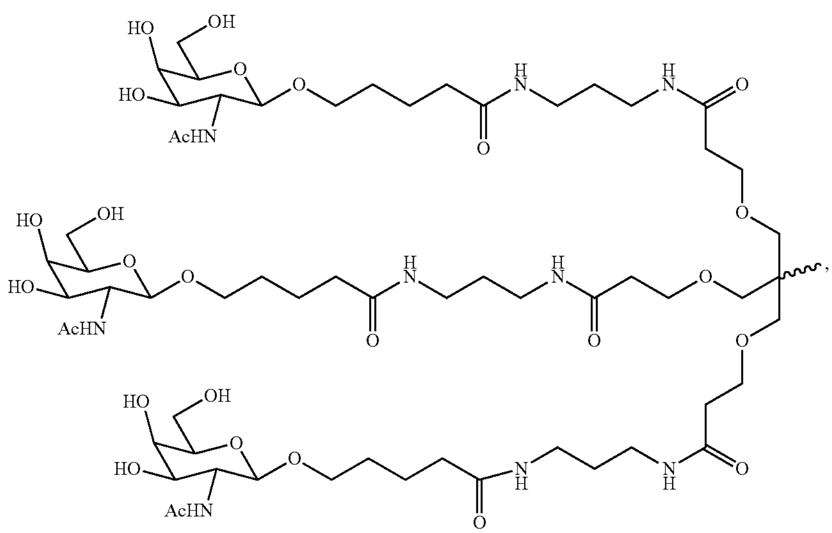,

-continued
Ligand 2
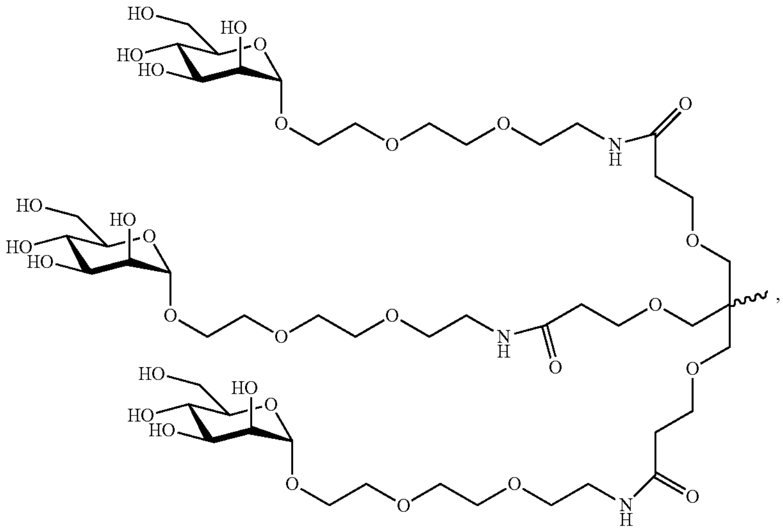
,
Ligand 3
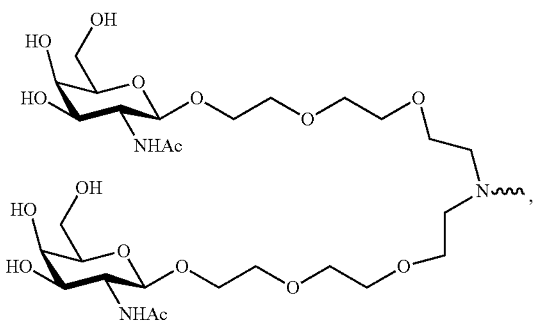
,
Ligand 4
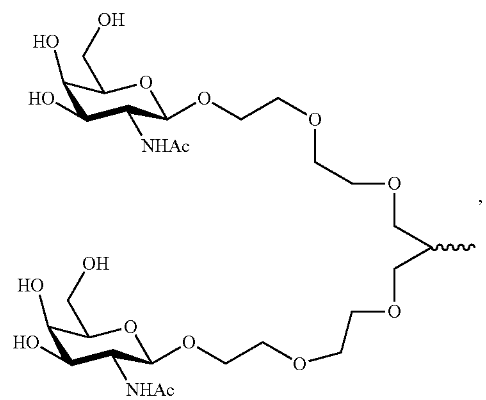
,
Ligand 5
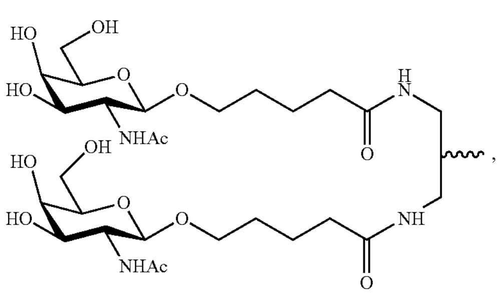
,
Ligand 6
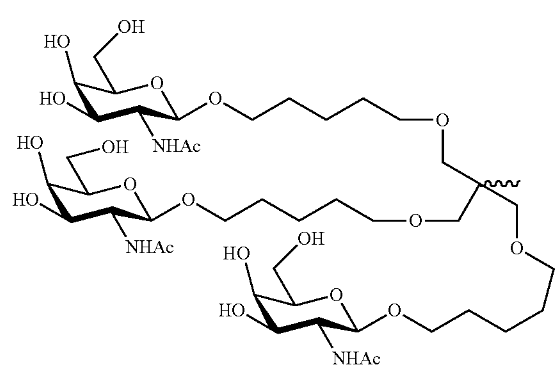
, -continued
Ligand 7
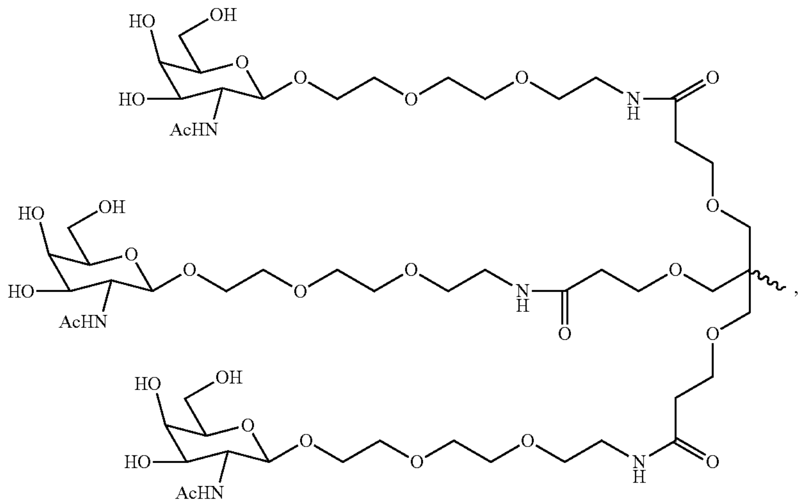
, or
Ligand 8
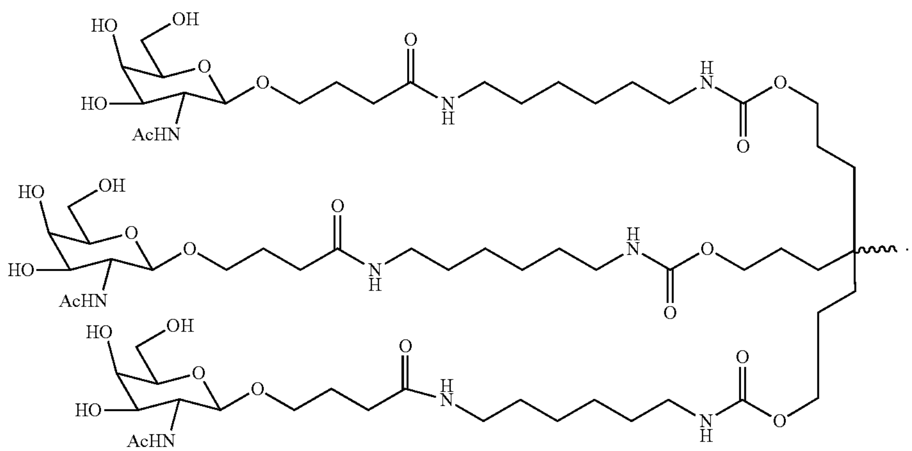
In some embodiments, a dsRNA described herein comprises Ligand 1, i.e., a ligand having the following structure:
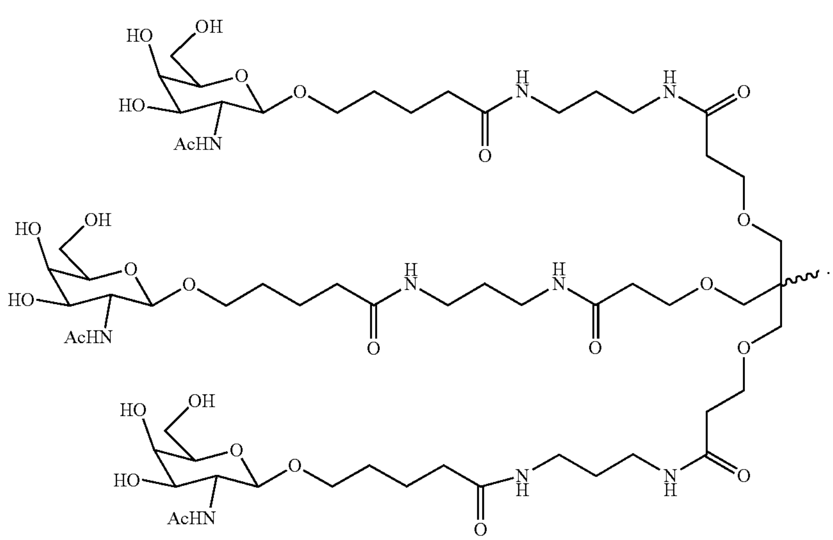 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, a dsRNA described herein comprises a ligand described in U.S. Pat. No. 5,994,517 or 6,906,182, content of each of which is incorporated herein by reference in its entirety.

Figure 3:
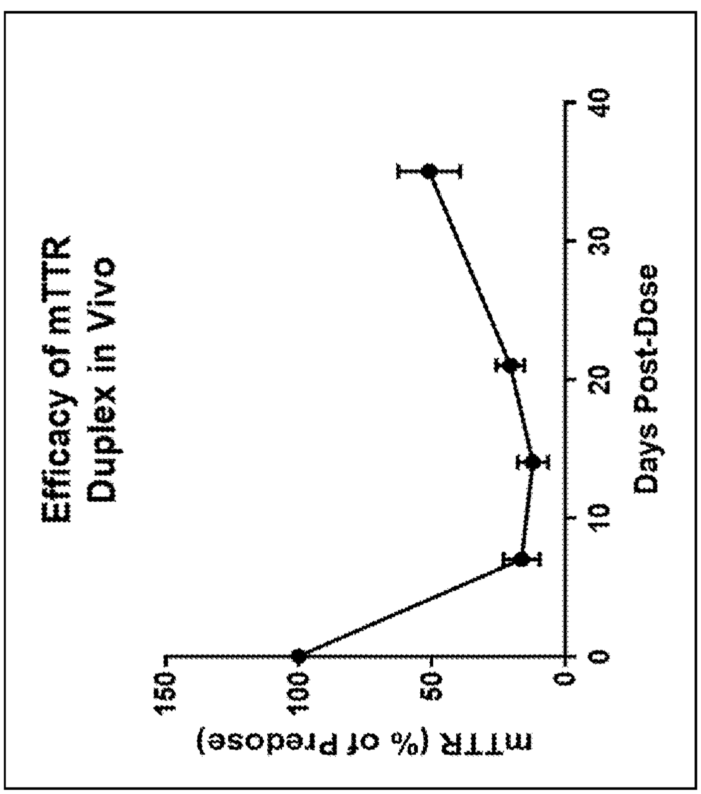

In some embodiments, the ligand can be a tri-antennary ligand described in FIG. 3 of U.S. Pat. No. 6,906,182. For example, a dsRNA described herein can comprise a ligand selected from the following tri-antennary ligands:

Tri-antennary

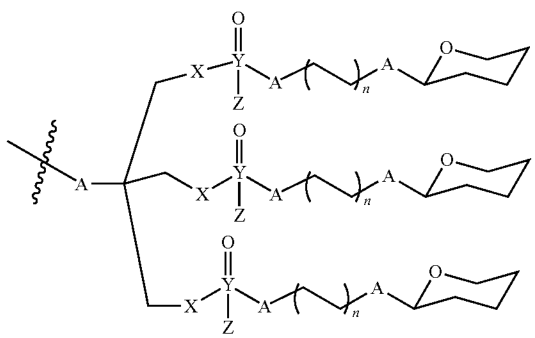

tris((heteroatom)methyl) + [heteroatom]methane

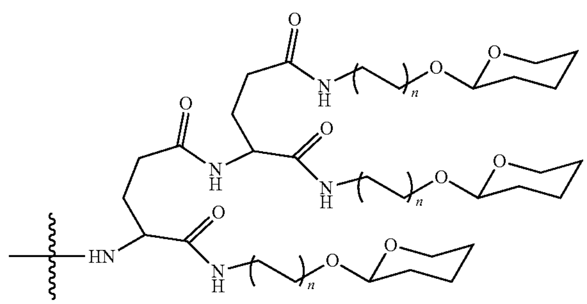

diglutamyl

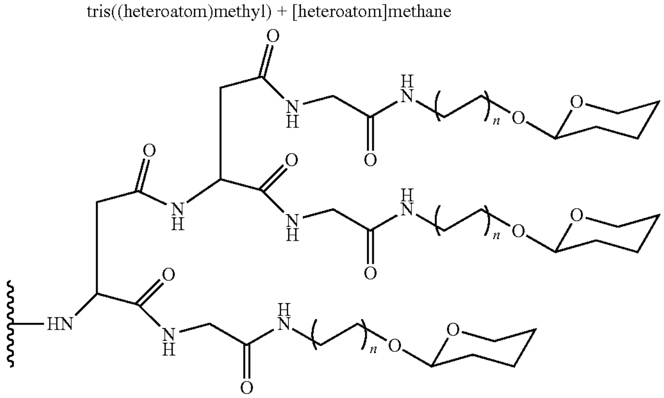

diasparatyl

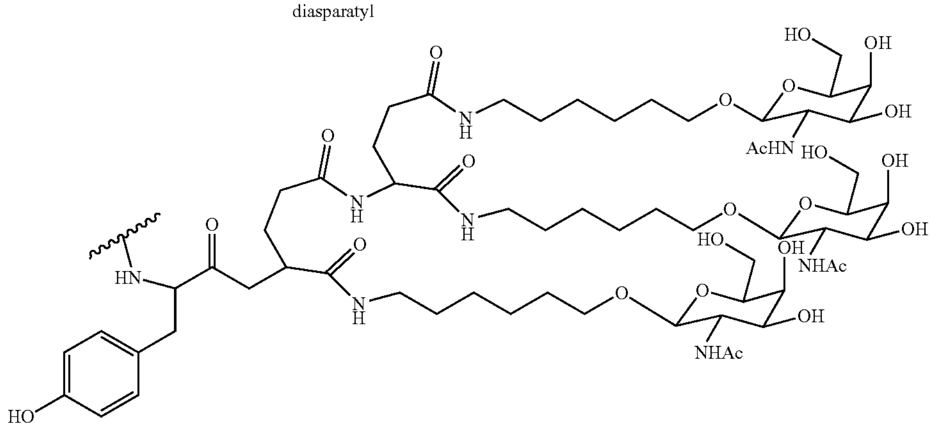

X = NH, O, S
Y = P or S
Z = NH-alkyl, $NH_2$, $O^-$, $S^+$
A = NH, $CH_2$, O, S
n = 2 to 17 2-carbon uits
Carbohydrate =

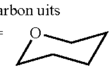

The ligand may be attached to the polynucleotide via a carrier. The carriers include (i) at least one “backbone attachment point,” preferably two “backbone attachment points” and (ii) at least one “tethering attachment point.” A “backbone attachment point” as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A “tethering attachment point” (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA molecule of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The ligand can be attached to the sense strand, antisense strand or both strands, at the 3'-end, 5'-end or both ends. For instance, the ligand can be conjugated to the sense strand, in particular, the 3'-end of the sense strand.

In some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); and wherein the sense strand does not comprise a glycol nucleic acid. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); and wherein the sense strand does not comprise a glycol nucleic acid (GNA). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length.

In some embodiments, the dsRNA comprises a sense strand and an antisense strand, each strand independently having a length of 15 to 35 nucleotides; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense and antisense strand the sense and the antisense strand can be independently 15, 16, 17, 18, 19, 20, 21, 22, 23, 24, or 25 nucleotides in length, preferably the sense strand and the antisense strand are independently 19, 20, 21, 22, 23, 24 or 25 nucleotides in length, more preferably, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA comprises at least one, e.g., at least two, at least three, at least four, at least five, at least six, at least seven or more, 2'-deoxy modifications at positions 6, 7, 8, 9, 10, 11, 12, 13, and 14 (preferably positions 7, 8, 9, 10, 11, 12 and 13) of the sense strand, counting from the 5'-end of the sense strand, and/or at positions 9, 10, 11, 12, 13, 14, 15 16 and 17 (preferably positions 10, 11, 12, 13, 14, 15 and 16) of the antisense strand counting from 5'-end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein the sense strand comprises at least two, e.g., at least three, at least four, at least five, at least six, at least seven or more, 2'-deoxy modifications in a central region of the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the sense strand comprises at least one, e.g., at least two, at least three, at least four, at least five, at least six, at least seven or more, 2'-deoxy modifications in a central region of the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the sense comprises at least one, e.g., at least two, at least three, at least four, at least five, at least six, at least seven or more, 2'-deoxy modifications in a central region of the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 18-30 nucleotides in length and comprises at least two 2'-deoxy modifications in a central region, e.g., positions 7, 8, 9, 10, 11, 12 and 13 of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least two, e.g., at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 18-30 nucleotides in length and comprises at least two 2'-deoxy modifications in a central region, e.g., positions 10, 11, 12, 13, 14, 15, and 16 of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-30 nucleotides in length and comprises at least two 2'-deoxy modifications in a central region, e.g., positions 10, 11, 12, 13, 14, 15, and 16 of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense comprises at least one, e.g., at least two, at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-30 nucleotides in length and comprises at least two 2'-deoxy modifications in a central region, e.g., positions 10, 11, 12, 13, 14, 15 and 16 of the antisense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand, and at least one, e.g., at least two, at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least one, e.g., at least two, at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense comprises at least one, e.g., at least two, at least three, at least four, at least five, at least six, at least seven or more, 2'-deoxy modifications in a central region of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-30 nucleotides in length and comprises at least one 2'-deoxy modifications in a central region, e.g., positions 10, 11, 12, 13, 14, 15, and 16 of the antisense strand, and at least one 2'-deoxy in positions 1, 2, 3, 4, 5 or 6 from either one of the 5'-end or the 3'-end. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least five, at least six, at least seven or more, 2'-deoxy modifications, e.g., at positions 2, 5, 7, 12 and 14, counting from 5-'end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein the antisense strand comprises at least five, at least six, at least seven or more, 2'-deoxy modifications, e.g., at positions 2, 5, 7, 12 and 14, counting from 5-'end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the antisense strand comprises at least five, at least six, at least seven or more, 2'-deoxy modifications, e.g., at positions 2, 5, 7, 12 and 14, counting from 5-'end of the antisense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand is 18-23 nucleotides in length and comprises at least five 2'-deoxy modifications, e.g., at positions 2, 5, 7, 12 and 14, counting from 5'-end of the antisense strand. In some embodiments, the sense strand is 21 nucleotides in length and the antisense strand is 23 nucleotides in length. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein at least two of the 2'-deoxy modifications are in the antisense strand, and at least one of the 2'-deoxy modification is in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein at least two of the 2'-deoxy modifications are in the antisense strand, and at least one of the 2'-deoxy modification is in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least two of the 2'-deoxy modifications are in the antisense strand, and at least one of the 2'-deoxy modification is in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least two 2'-deoxy modifications and the sense strand comprises at least one 2'-deoxy modification, wherein the 2'-deoxy modifications are at positions 2 and 14 of the antisense strand, counting from 5'-end of the antisense strand, and at position 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein at least three of the 2'-deoxy modifications are in the antisense strand, and at least two of the 2'-deoxy modifications are in the sense strand. In some embodiments, the antisense strand comprises at least three 2'-deoxy modifications and the sense strand comprises at least two 2'-deoxy modification, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein at least three of the 2'-deoxy modifications are in the antisense strand, and at least two of the 2'-deoxy modifications are in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least three 2'-deoxy modifications and the sense strand comprises at least two 2'-deoxy modifications, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least three of the 2'-deoxy modifications are in the antisense strand, and at least two of the 2'-deoxy modifications are in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least three 2'-deoxy modifications and the sense strand comprises at least two 2'-deoxy modifications, wherein the 2'-deoxy modifications are at positions 2, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least seven 2'-deoxy modifications on the sense and/or antisense strands; wherein the dsRNA molecule has a double stranded (duplex) region of between 18 to 25 base pairs; wherein the dsRNA molecule comprises a ligand, e.g., a ligand of any one of Formula (IV)-(VII); wherein the sense strand does not comprise a glycol nucleic acid; and wherein at least five of the 2'-deoxy modifications are in the antisense strand, and at least two of the 2'-deoxy modification is in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least five 2'-deoxy modifications and the sense strand comprises at least two 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least seven 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand, e.g., a ligand of any one of Formula (IV)-(VII); wherein the sense strand does not comprise a glycol nucleic acid; and wherein at least five of the 2'-deoxy modifications are in the antisense strand, and at least two of the 2'-deoxy modifications are in the sense strand. In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein. In some embodiments, the antisense strand comprises at least five 2'-deoxy modifications and the sense strand comprises at least two 2'-deoxy modification, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length.

In some embodiments, the dsRNA comprises a sense strand and an antisense strand, each strand independently having a length of 15 to 35 nucleotides, e.g., independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides counting from the 5' end of the antisense strand; at least three, four, five or six 2'-deoxy modifications on the sense and/or antisense strands; wherein the dsRNA molecule has a double stranded (duplex) region of 18, 19, 21, 22, 23, 24 or 25 base pairs; wherein the dsRNA molecule comprises a ligand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein at least five of the 2'-deoxy modifications are in the antisense strand, and at least two of the 2'-deoxy modifications are in the sense strand. In some embodiments, the antisense strand comprises at least five 2'-deoxy modifications and the sense strand comprises at least two 2'-deoxy modifications, wherein the 2'-deoxy modifications are at positions 2, 5, 7, 12 and 14 of the antisense strand, counting from 5'-end of the antisense strand, and at positions 9 and 11 of the sense strand, counting from 5'-end of the sense strand. In some embodiments, the sense strand is 21 nucleotides in length and the antisense strand is 23 nucleotides in length. In some embodiments, the non-natural nucleotides are selected from the group consisting of acyclic nucleotides, locked nucleic acid (LNA), HNA, CeNA, 2'-methoxyethyl, 2'-O-allyl, 2'-C-allyl, 2'-fluoro, 2'-O—N-methylacetamido (2'-O-NMA), a 2'-O-dimethylaminoethoxyethyl (2'-O-DMAEOE), 2'-O-aminopropyl (2'-O-AP), and 2'-ara-F.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15

16 and 17, preferably positions 10, 11, 12, 13, 14, 15 and 16, counting from 5'-end of the antisense strand). In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand). In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least one, e.g., at least two, at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least two, e.g., at least three, at least four, at least five, at least six, at least seven or more, 2'-deoxy modifications in the central region of the antisense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand). In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand). In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15

16 and 17, preferably positions 10, 11, 12, 13, 14, 15 and 16, counting from 5'-end of the antisense strand); and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand); wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5' end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the dsRNA comprises at least two, e.g., at least three, at least four, at least five, at least six, at least seven or more, 2'-deoxy modifications in the central region of the sense strand (e.g., at positions 6, 7, 8, 9, 10, 11, 12, 13, and 14, preferably positions 7, 8, 9, 10, 11, 12 and 13, counting from the 5'-end of the sense strand), and at least one, e.g., at least two, at least three, at least four, at least five, at least six, at least seven or more, 2'-deoxy modifications in the central region of the sense strand (e.g., at positions 9, 10, 11, 12, 13, 14, 15 16 and 17, preferably positions 10, 11, 12, 13, 14, 15 and 16, counting from 5'-end of the antisense strand), and at least one 2'-deoxy modification in a non-central region, e.g., within 1, 2, 3, 4, 5 or 6 nucleotides from either 5'-end and/or 3'-end of the antisense strand; wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand;

wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; wherein the antisense strand comprises at least five 2'-deoxy modifications at positions 2, 5, 7, 12 and 14 of the antisense strand, counting from 5'-end of the antisense strand; wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least two 2'-deoxy modifications at positions 2 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least two 2'-deoxy modifications at positions 2 and 14 of the antisense strand, counting from wherein the sense strand comprises at least one 2'-deoxy modification at position 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least three 2'-deoxy modifications at positions 2, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least three 2'-deoxy modifications at positions 2, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from 5'-end of the antisense strand. In some preferred embodiments, the sense strand is 21 nucleotides in length and the antisense strand is 23 nucleotides in length.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the sense strand does not comprise a glycol nucleic acid.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and the dsRNA comprises less than 20%, e.g., less than 15%, less than 10%, or less than 5% non-natural nucleotides or the dsRNA agent comprises all natural nucleotides.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; wherein the antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5' end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; and wherein the dsRNA molecule has a double stranded (duplex) region of 18, 19, 21, 22, 23, 24 or 25 base pairs; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phosphorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the sense strand does not comprise a glycol nucleic acid; wherein the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

In some embodiments, the invention provides a dsRNA comprising a sense strand and an antisense strand, each strand independently having a length of 15 to 35 nucleotides, e.g., independently 17-30 nucleotides in length, independently 15, 16, 17, 18, 19, 20, 21, 22, 23, 24, or 25 nucleotides in length, preferably independently 17, 18, 19, 20, 21, 22, 23, 24 or 25 nucleotides in length; at least two phsophorothioate internucleotide linkages between the first five nucleotides, counting from the 5'end of the antisense strand; antisense strand comprises at least five 2'-deoxy modifications at positions 2, 5, 7, 12 and 14 of the antisense strand, counting from wherein the sense strand comprises at least two 2'-deoxy modifications at positions 9 and 11, counting from 5'-end of the sense strand; wherein the dsRNA molecule has a double stranded (duplex) region of 18, 19, 21, 22, 23, 24 or 25 base pairs; wherein the sense strand does not comprise a glycol nucleic acid; the dsRNA comprises less than 20%, e.g., less than 15%, less than 10%, or less than 5% non-natural nucleotides or the dsRNA agent comprises all natural nucleotides; and wherein the dsRNA molecule comprises a ligand, e.g., a ligand of any one of Formula (IV)-(VII). In some embodiments, the ligand binds with or targets a liver cell or receptor, e.g., the ligand binds with or target the asialoglycoprotein receptor (ASGPR). In some embodiments, the ligand is a multivalent ligand, e.g., a ligand of Formula (VII). In some further embodiments, the ligand is a GalNAc derivative, e.g., a ligand selected from the Ligands 1-8 disclosed herein.

Overhangs and Blunt Ends

In some embodiments, the dsRNA molecule of the invention comprises one or more overhang regions and/or capping groups of dsRNA molecule at the 3'-end, or 5'-end or both ends of a strand. The overhang can be 1-10 nucleotides in length. For example, the overhang can be 1, 2, 3, 4, 5, 6, 7, 8, 9 or 10 nucleotides in length. In some embodiments, the overhang is 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target sequence or it can be complementary to the gene sequences being targeted or it can be the other sequence. The first and second strands can also be joined, e.g., by additional bases to form a hairpin, or by other non-base linkers.

In some embodiments, the nucleotides in the overhang region of the dsRNA molecule of the invention can each independently be a modified or unmodified nucleotide including, but not limited to 2'-sugar modified, such as, 2'-Fluoro 2'-O-methyl, thymidine (T), 2'-O-methoxyethyl-5-methyluridine, 2'-O-methoxyethyladenosine, 2'-O-methoxyethyl-5-methylcytidine, GNA, SNA, hGNA, hhGNA, mGNA, TNA, h' GNA, and any combinations thereof. For example, dTdT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA molecule of the invention may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

The dsRNA molecule of the invention may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA can also have a blunt end, located at the 5'-end of the antisense strand (or the 3'-end of the sense strand) or vice versa.

Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example, the single overhang is at least one, two, three, four, five, six, seven, eight, nine, or ten nucleotides in length. In some embodiments, the dsRNA has a 2 nucleotide overhang on the 3'-end of the antisense strand and a blunt end at the 5'-end of the antisense strand.

Modified Nucleotides

The dsRNA of the invention can comprise one or more modified nucleotides. For example, every nucleotide in the sense strand and antisense strand of the dsRNA molecule can be modified. Each nucleotide can be modified with the same or different modification which can include one or more alteration of one or both of the non-linking phosphate oxygens and/or of one or more of the linking phosphate oxygens; alteration of a constituent of the ribose sugar; replacement of the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a central region, may only occur at a non-terminal t region, or may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide.

In some embodiments, the dsRNA molecule of the invention comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA molecule of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the invention comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the invention comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the invention comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the invention comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

Various publications describe multimeric siRNA which can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

5'-Modifications

In some embodiments dsRNA molecules of the invention are 5' phosphorylated or include a phosphoryl analog at the 5' prime terminus. 5'-phosphate modifications include those which are compatible with RISC mediated gene silencing. Suitable modifications include: 5'-monophosphate ($(HO)_2(O)P—O-5'$); 5'-diphosphate ($(HO)_2(O)P—O—P(HO)(O)—O-5'$); 5'-triphosphate ($(HO)_2(O)P—O—(HO)(O)P—O—P(HO)(O)—O-5'$); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P—O-5'$); 5'-monodithiophosphate (phosphorodithioate; (HO)(HS)(S)P—O-5'), 5'-phosphorothiolate ($(HO)_2(O)P—S-5'$); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ($(HO)_2(O)P—NH-5'$, $(HO)(NH_2)(O)P—O-5'$), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), $(OH)_2(O)P$-5'-CH2-), 5'-alkyletherphosphonates (R=alkylether=methoxymethyl (MeOCH2-), ethoxymethyl, etc., e.g. RP(OH)(O)—O-5'-). In one example, the modification can in placed in the antisense strand of a dsRNA molecule.

Thermally Destabilizing Modifications.

The dsRNA agents of the invention can comprise thermally destabilizing modifications in the seed region of the antisense strand (i.e., at positions 2-9 of the 5'-end of the antisense strand) to reduce or inhibit off-target gene silencing. Without wishing to be bound by a theory, dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, thermally destabilizing modification of the duplex is located in positions 2-9, or preferably positions 4-8, from the 5'-end of the antisense strand. In some further embodiments, the thermally destabilizing modification of the duplex is located at position 5, 6, 7 or 8 from the 5'-end of the antisense strand.

In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5, 6, 7, 8 or 9 from the 5'-end of the antisense strand.

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA). For example, the thermally destabilizing modifications can include, but are not limited to, mUNA and GNA building blocks as follows:

Mod 1

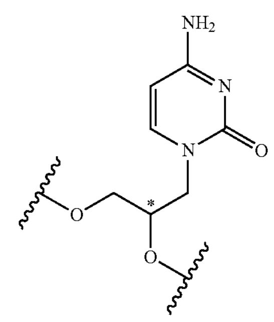

(GNA-C)

Mod 2

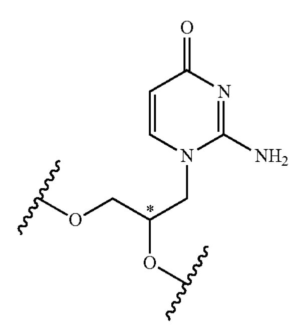

(GNA-isoC)

-continued
Mod 3
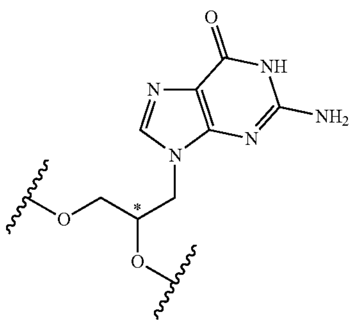
(GNA-G)
Mod 4
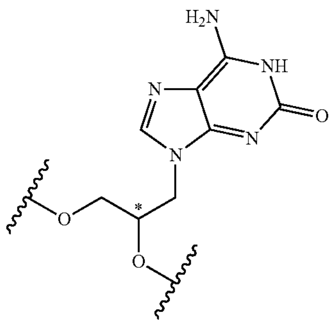
(GNA-isoG)
Mod 5
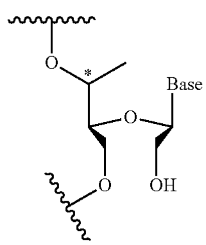
(5′-mUNA)
Mod 6
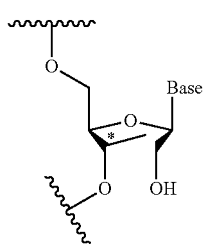
(3′-mUNA)
Mod 7
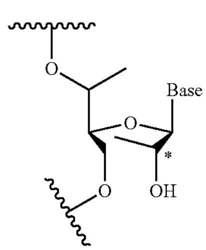
(3′-mUNA)
-continued
Mod 8
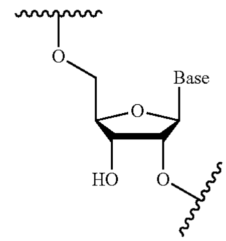
(2′-5′-RNA)
*both stereoisomers tested
Mod1
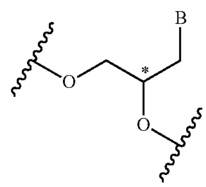
(GNA)
Mod2
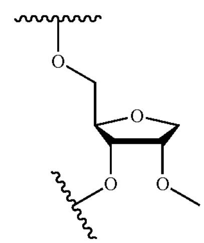
(2′-OMe Abasic Spacer)
Mod3
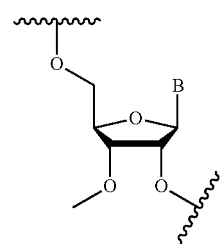
(2′-OMe Abasic Spacer)
Mod4
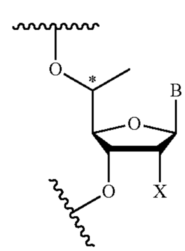
(5′-Me)
X = OMe, F -continued
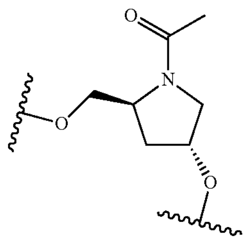
(Hyp-spacer)
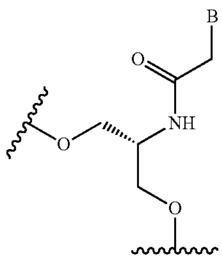
(SNA)
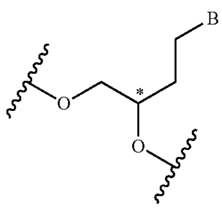
(hGNA)
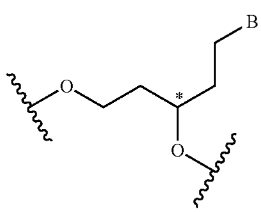
(hhGNA)
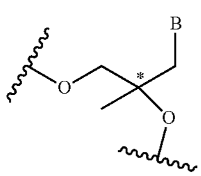
(mGNA)
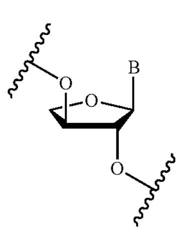
(TNA)
-continued
Mod5
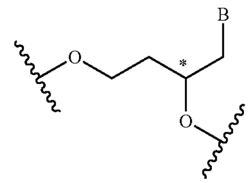
h'GNA
*Both stereoisomers tested
Mod6
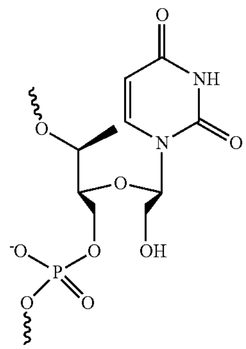
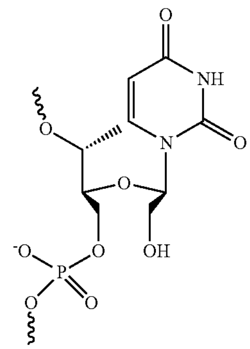
Mod7
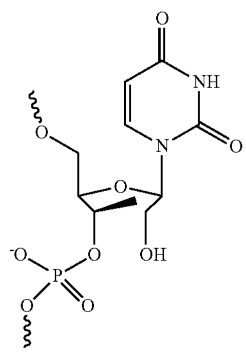
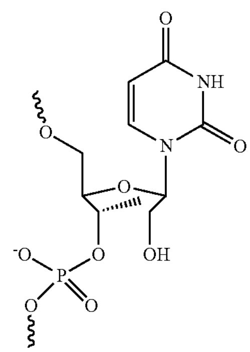
Mod8
Mod9
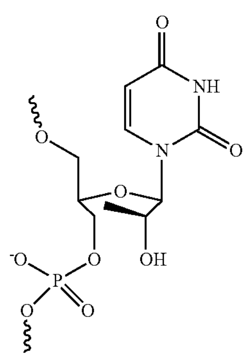
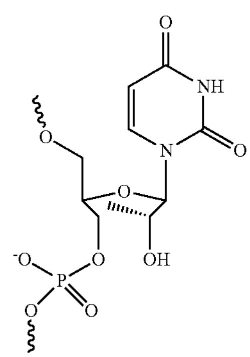
Mod10
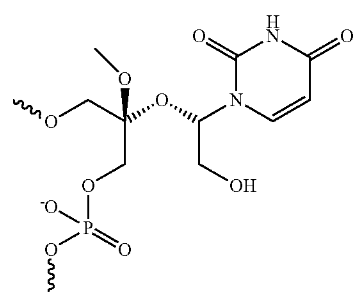

-continued
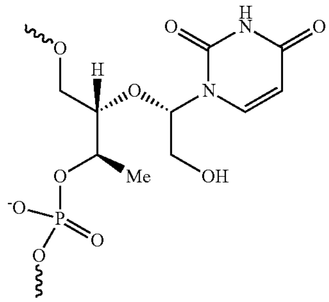
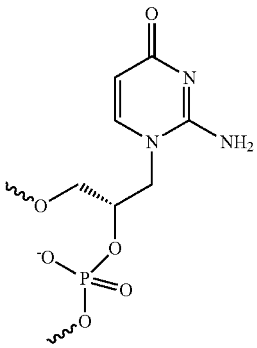
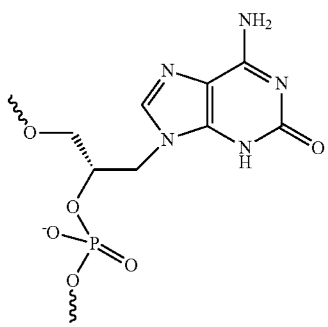
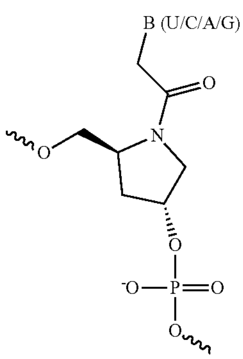
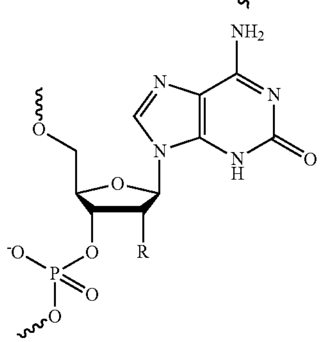
isoG
-continued
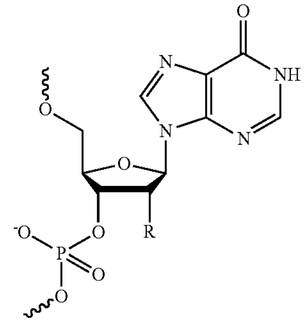
inosine
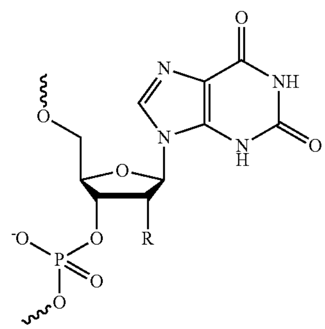
xanthosine
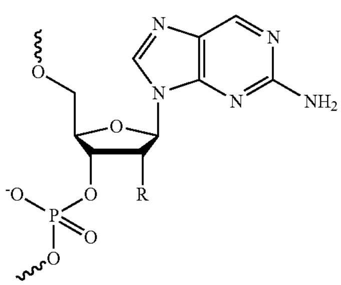
2-aminopurine
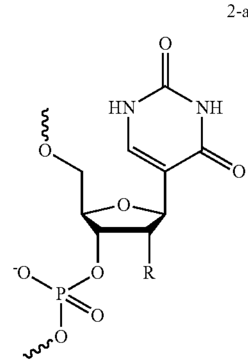
pseudouracil
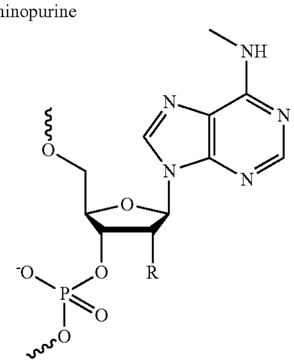
N6-methyladenine
(R = H, F, OMe etc)
In some embodiments, the destabilizing modification is selected from the group consisting of GNA-isoC, GNA-isoG, 5'-mUNA, 4'-mUNA, 3'-mUNA, and 2'-mUNA.
In some embodiments, the destabilizing modification mUNA is selected from the group consisting of

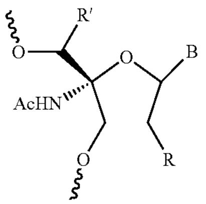 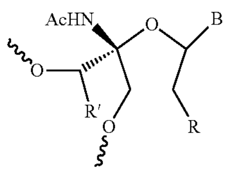

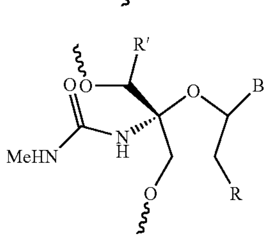 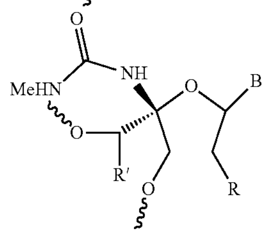

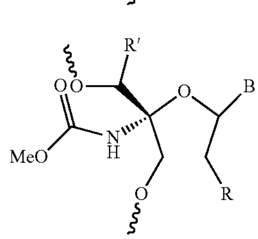 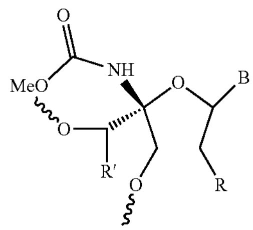

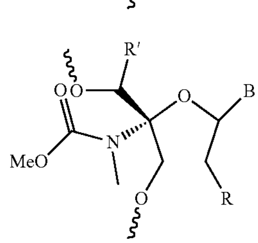 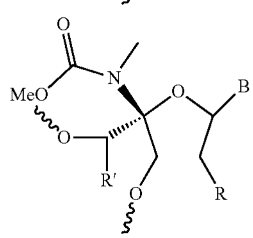

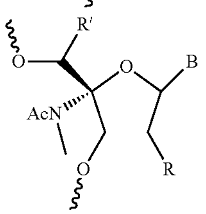 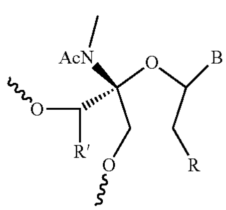

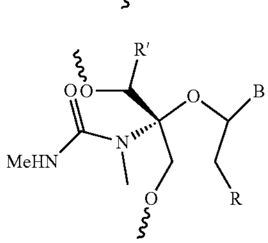 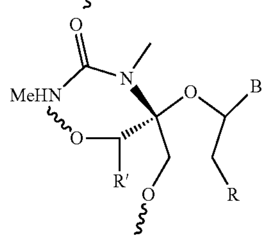

R=H, OH; OMe; Cl, F; OH; O—$(CH_2)_2$OMe; SMe, $NMe_2$; $NH_2$; Me; CCH (alkyne), O-nPr;

O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modiifed purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 2-thiouridine; 4-thiouridine; C5-modified pyrimidines; C2-modified purines; N8-modiifed purines; 7-deazapurines, phenoxazine; G-clamp; non-canonical mono, bi and tricyclic heterocycles; and Stereochemistry is R or S and combination of R and S for the unspecified chiral centers.

In some embodiments, the destabilizing modification mUNA is selected from the group consisting of

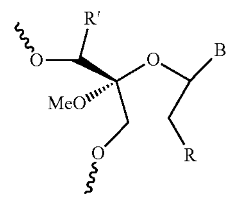 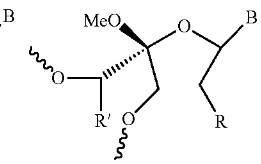

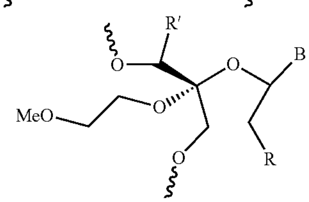

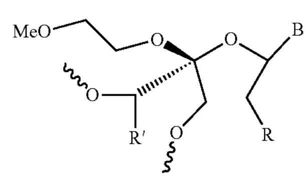 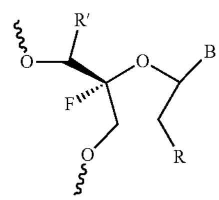

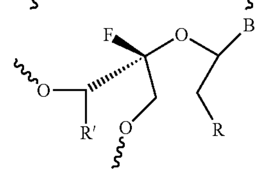

R=H, OH; OMe; Cl, F; OH; O—$(CH_2)_2$OMe; SMe, $NMe_2$; $NH_2$; Me; CCH (alkyne), O-nPr;

O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modiifed purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 2-thiouridine; 4-thiouridine; C5-modified pyrimidines; C2-modified purines; N8-modiifed purines; 7-deazapurines, phenoxazine; G-clamp; non-canonical mono, bi and tricyclic heterocycles; and Stereochemistry is R or S and combination of R and S for the unspecified chiral centers.

In some embodiments, the destabilizing modification mUNA is selected from the group consisting of

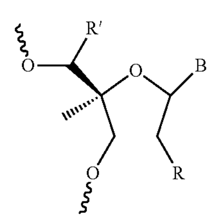 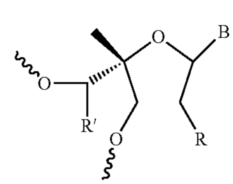

-continued

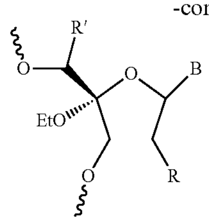
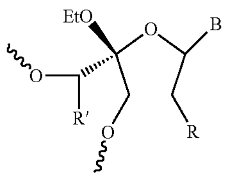
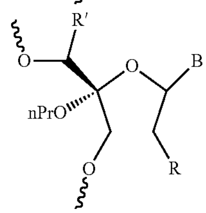
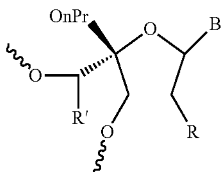
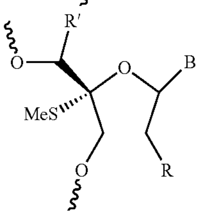
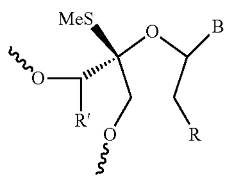
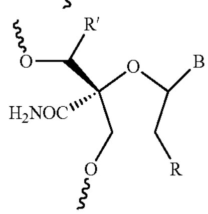
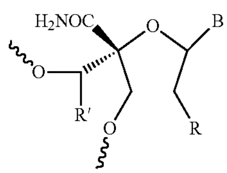
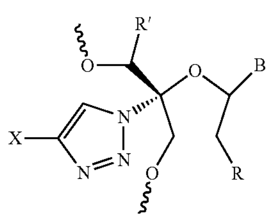
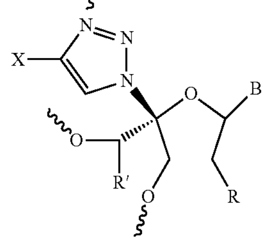

R=H, OMe; F; OH; O—$(CH_2)_2$OMe; SMe, $NMe_2$; $NH_2$; Me; O-nPr; O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modiifed purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 7-deazapurines; and Stereochemistry is R or S and combination of R and S for the unspecified chiral centers.

In some embodiments, the destabilizing modification mUNA is selected from the group consisting of

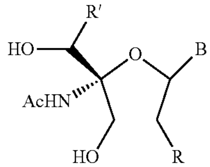
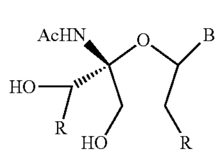

-continued

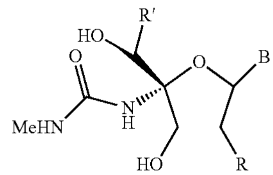
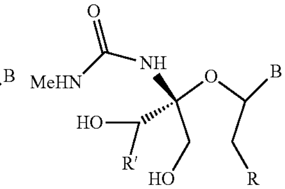
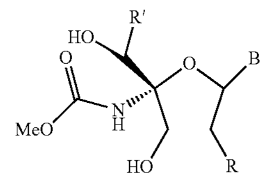
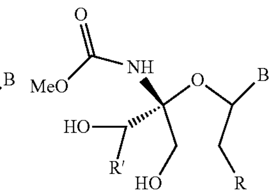
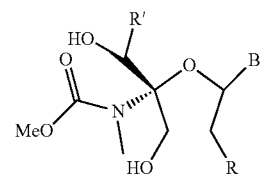
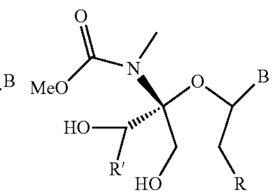
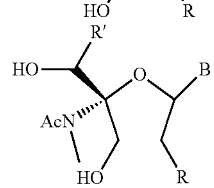
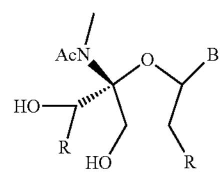
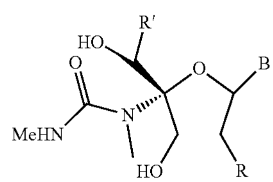
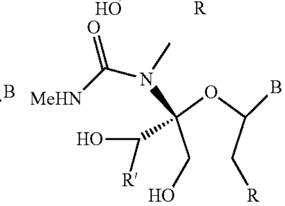

R=H, OH; OMe; Cl, F; OH; O—$(CH_2)_2$OMe; SMe, $NMe_2$; $NH_2$; Me; CCH (alkyne), O-nPr;

O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modiifed purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 2-thiouridine; 4-thiouridine; C5-modified pyrimidines; C2-modified purines; N8-modiifed purines; 7-deazapurines, phenoxazine; G-clamp; non-canonical mono, bi and tricyclic heterocycles; and Stereochemistry is R or S and combination of R and S for the unspecified chiral centers In some embodiments, the destabilizing modification mUNA is selected from the group consisting of

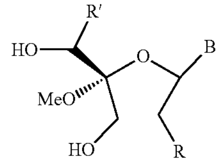
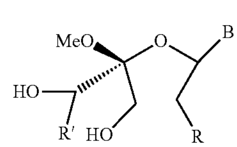

-continued

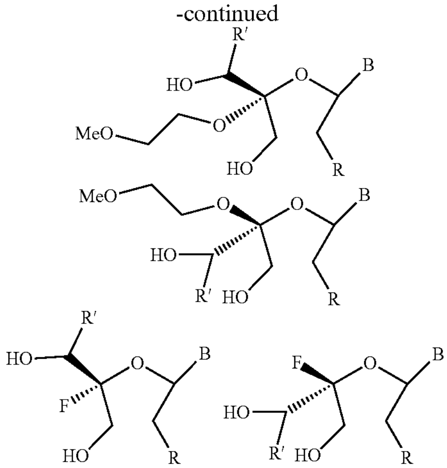

R=H, OH; OMe; Cl, F; OH; O—$(CH_2)_2$OMe; SMe, $NMe_2$; $NH_2$; Me; CCH (alkyne), O-nPr;

O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 2-thiouridine; 4-thiouridine; C5-modified pyrimidines; C2-modified purines; N8-modified purines; 7-deazapurines, phenoxazine; G-clamp; non-canonical mono, bi and tricyclic heterocycles; and Stereochemistry is R or S and combination of R and S for the unspecified chiral centers In some embodiments, the modification mUNA is selected from the group consisting of

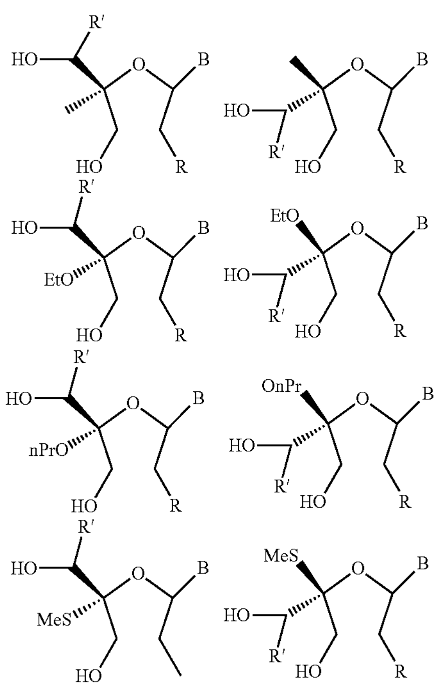

-continued

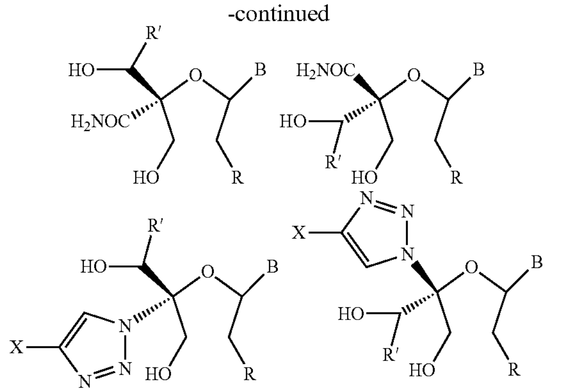

R=H, OMe; F; OH; O—$(CH_2)_2$OMe; SMe, $NMe_2$; $NH_2$; Me; O-nPr; O-alkyl; O-alkylamino;

R'=H, Me;

B=A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil; isoC; isoG; 2,6-diamninopurine; pseudocytosine; 2-aminopurine; xanthosine; N6-alkyl-A; 06-alkyl-G; 7-deazapurines; and Stereochemistry is R or S and combination of R and S for the unspecified chiral centers In some embodiments, the modification mUNA is selected from the group consisting of

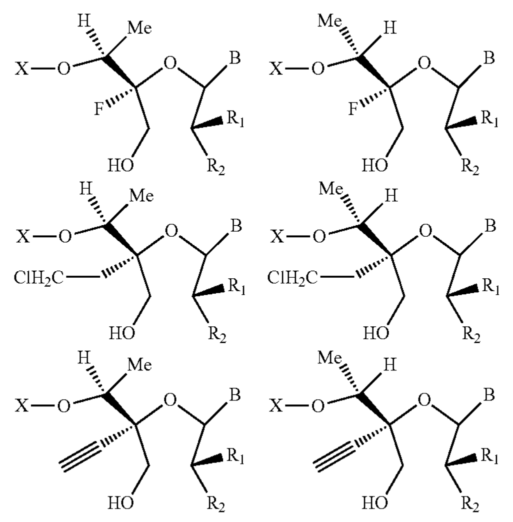

$R_1$, $R_2$ = OTBS; F, H, Me, Cl

B = $A^{Bz}$; $C^{Bz}$; 5-Me-$C^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines X = DMTr,

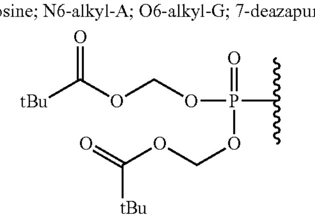

-continued
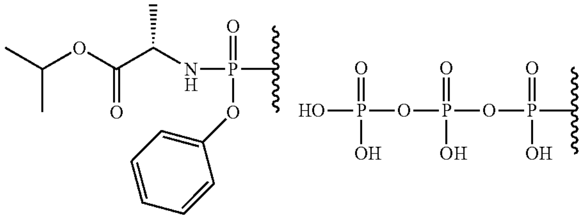
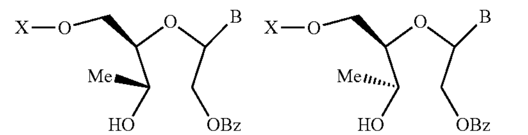
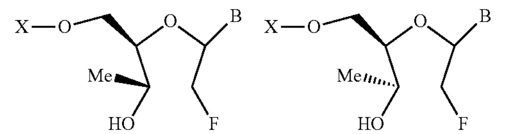
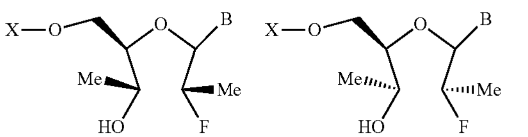
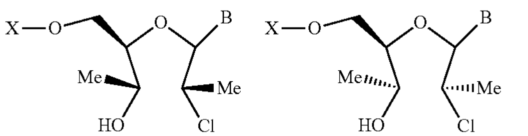
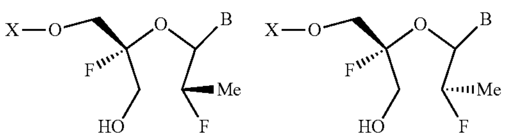
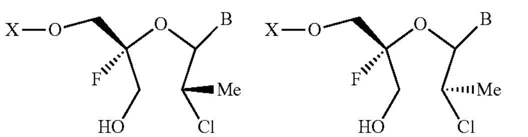
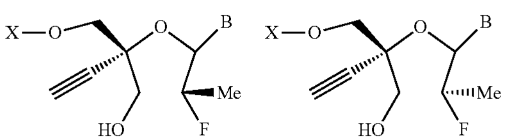
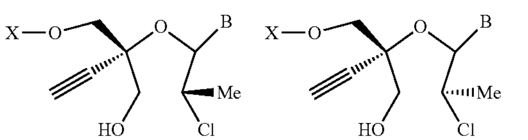
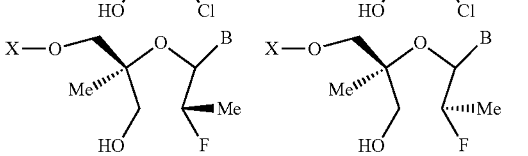
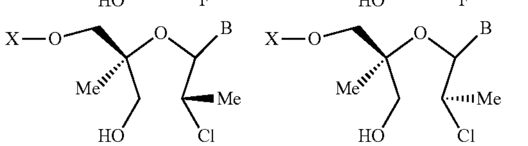
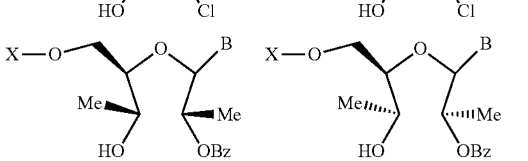
-continued
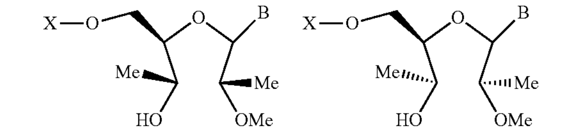
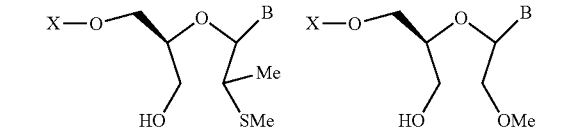
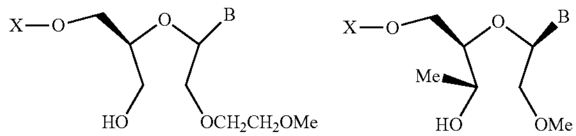
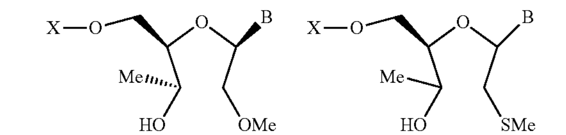
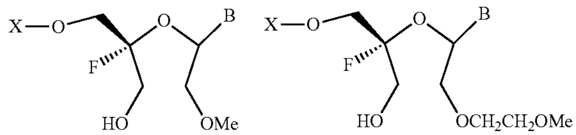
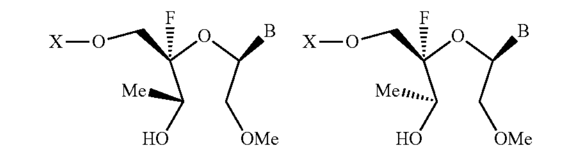
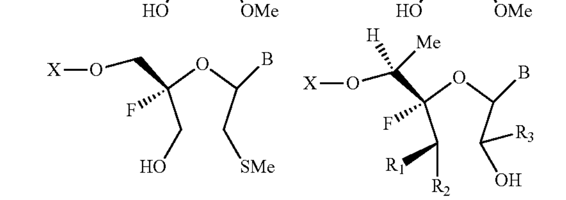
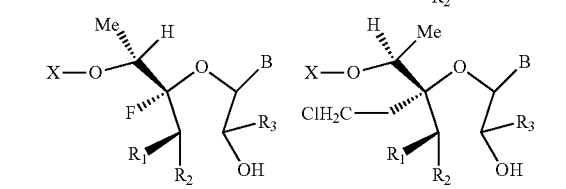
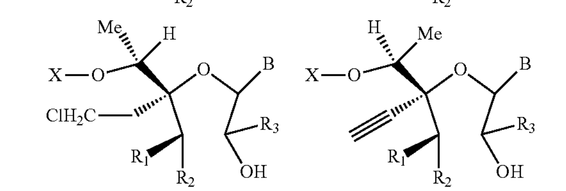
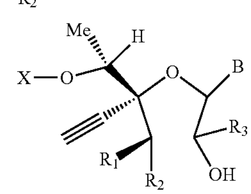
$R_1$, $R_2$ = OTBS; F, H, Me, Cl
$R_3$ = H, Me
B = $A^{Bz}$; $C^{Bz}$; 5-Me-$C^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles; pseudouracil isoC; isoG; 2,6-diamninopurine; pseudocytosine; 2-aminopurine; xanthosine; N6-alkyl-A; O6-alkyl-G; 7-deazapurines -continued
X = DMTr, 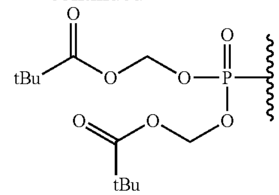
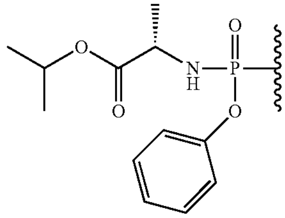
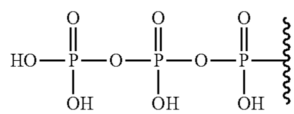
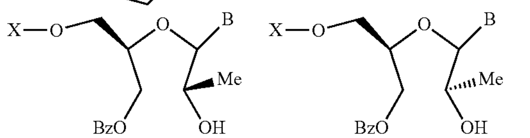
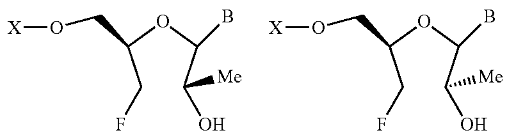
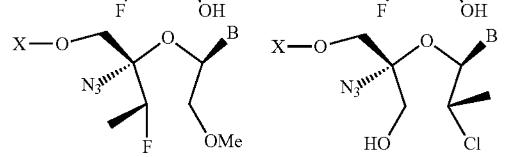
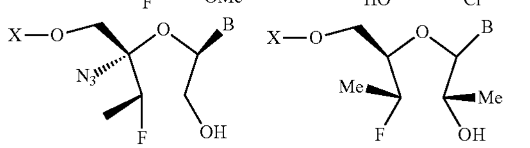
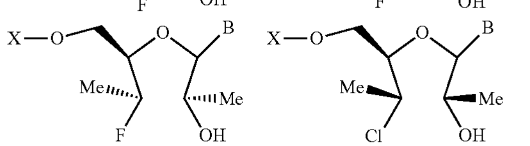
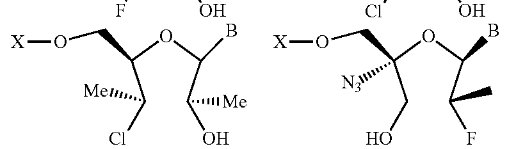
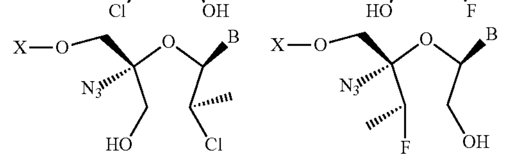
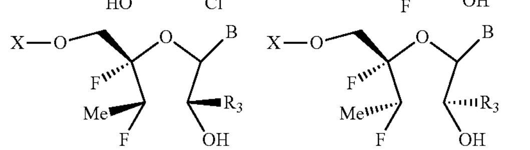
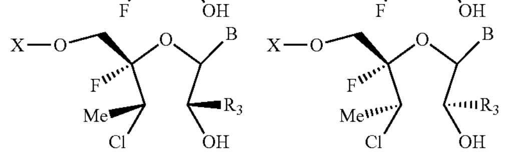
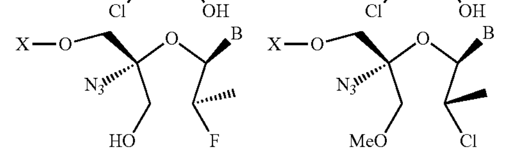
-continued
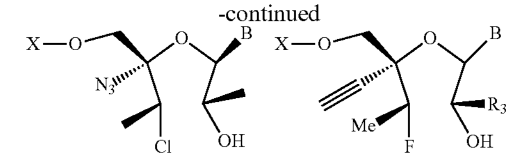
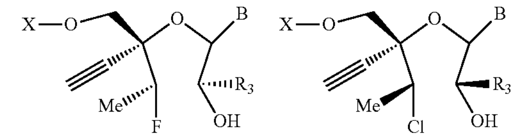
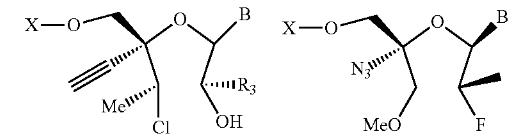
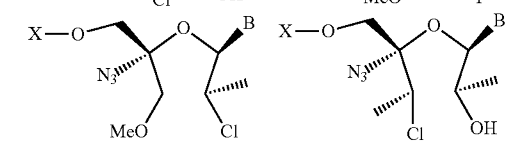
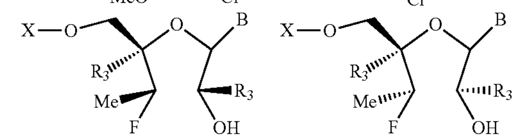
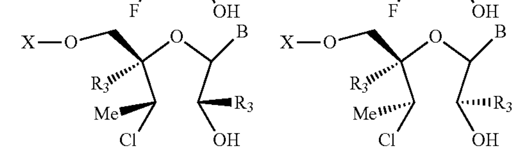
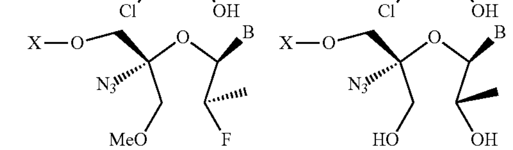
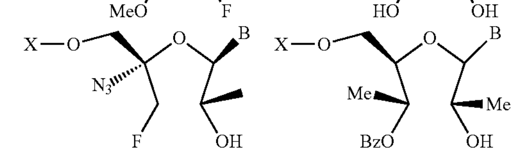
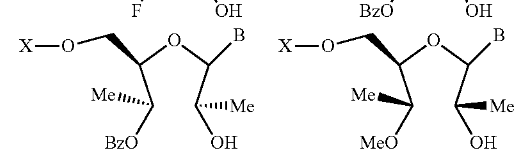
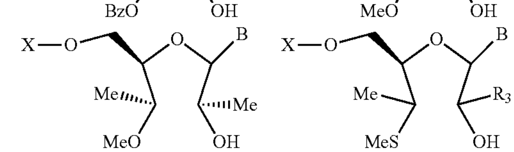
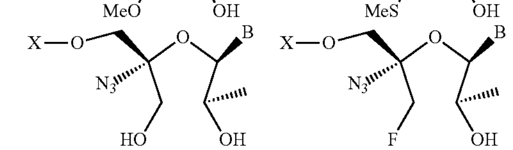
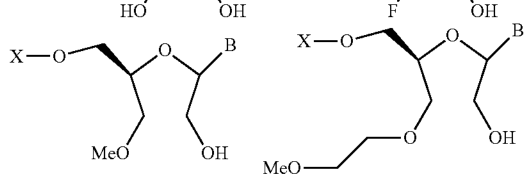
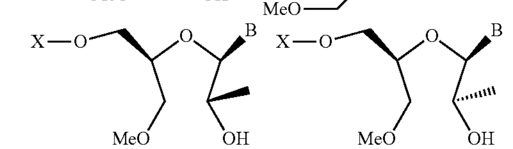

-continued

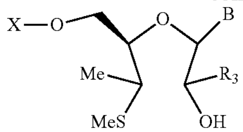

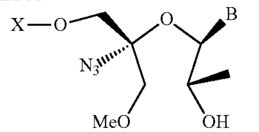

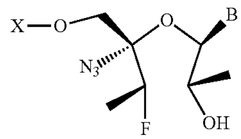

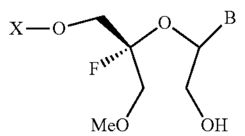

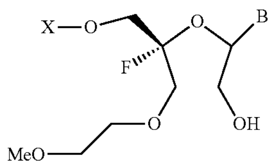

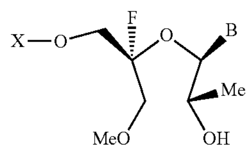

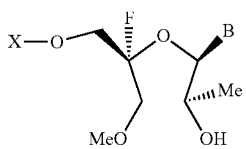

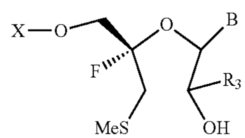

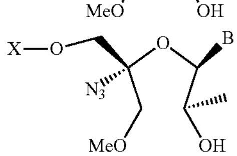

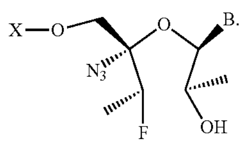

Exemplified abasic modifications include, but are not limited to the following:

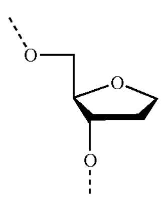

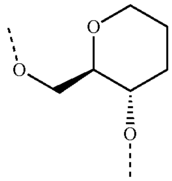

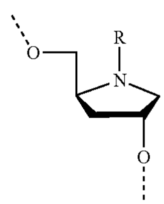

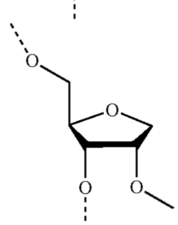

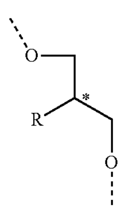

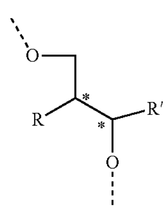

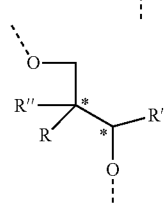

Wherein R=H, Me, Et or OMe; R'=H, Me, Et or OMe; R"=H, Me, Et or OMe

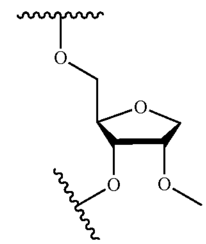

Mod2
(2'-OMe Abasic Spacer)

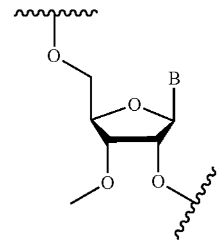

Mod3
(3'-OMe)

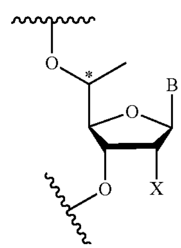

Mod4
(5'-Me)
X = OMe, F

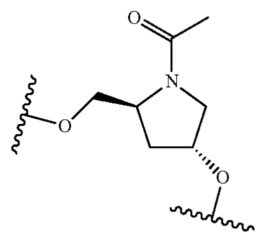

Mod5
(Hyp-spacer)

wherein B is a modified or unmodified nucleobase and the asterisk on each structure represents either R, S or racemic.

Exemplified sugar modifications include, but are not limited to the following:

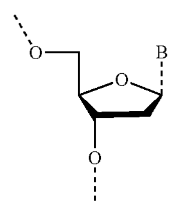

2'-deoxy

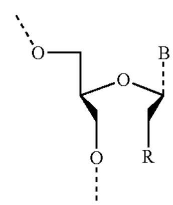

unlocked nucleic acid
R = H, OH, O-alkyl

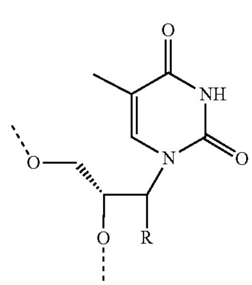

glycol nucleic acid
R = H, OH, O-alkyl

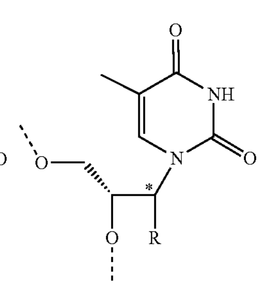

glycol nucleic acid
R = H, OH, O-alkyl

-continued

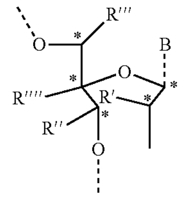

unlocked nucleic acid

R = H, OH, $CH_3$, $CH_2CH_3$, O-alkyl, $NH_2$, NHMe, $NMe_2$

R′ = H, OH, $CH_3$, $CH_2CH_3$, O-alkyl, $NH_2$, NHMe, $NMe_2$

R″ = H, OH, $CH_3$, $CH_2CH_3$, O-alkyl, $NH_2$, NHMe, $NMe_2$

R‴ = H, OH, $CH_3$, $CH_2CH_3$, O-alkyl, $NH_2$, NHMe, $NMe_2$

R⁗ = H, OH, $CH_3$, $CH_2CH_3$, O-alkyl, $NH_2$, NHMe, $NMe_2$

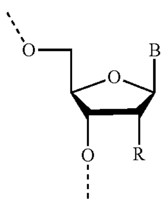

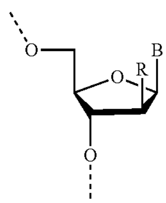

R = H, methyl, ethyl wherein B is a modified or unmodified nucleobase and the asterisk on each structure represents either R, S or racemic.

In some embodiments the thermally destabilizing modification of the duplex is selected from the mUNA and GNA building blocks described in Examples 1-3 herein. In some embodiments, the destabilizing modification is selected from the group consisting of GNA-isoC, GNA-isoG, 5'-mUNA, 4'-mUNA, 3'-mUNA, and 2'-mUNA. In some further embodiments of this, the dsRNA molecule further comprises at least one thermally destabilizing modification selected from the group consisting of GNA, 2'-OMe, 3'-OMe, 5'-Me, Hy p-spacer, SNA, hGNA, hhGNA, mGNA, TNA and h'GNA (Mod A-Mod K).

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent and/or at least one of ribose carbons or oxygen (e.g., C1', C2', C3', C4' or O4') are independently or in combination absent from the nucleotide. In some embodiments, acyclic nucleotide is

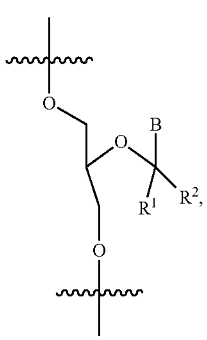

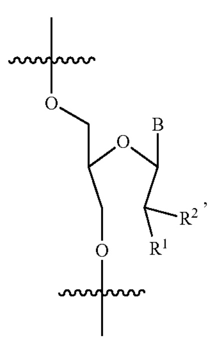

-continued

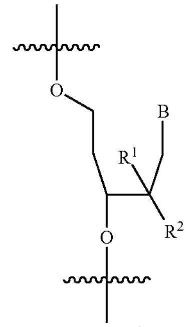

,

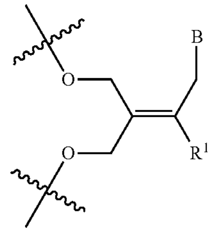

or

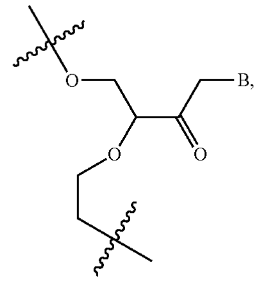

wherein B is a modified or unmodified nucleobase, R1 and R2 independently are H, halogen, OR3, or alkyl; and R3 is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

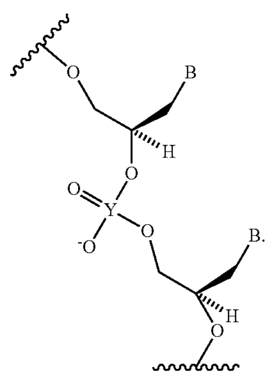

(R)-GNA

The thermally destabilizing modification of the duplex can be mismatches (i.e., noncomplementary base pairs)

between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W—C H-bonding to complementary base on the target mRNA, such as:

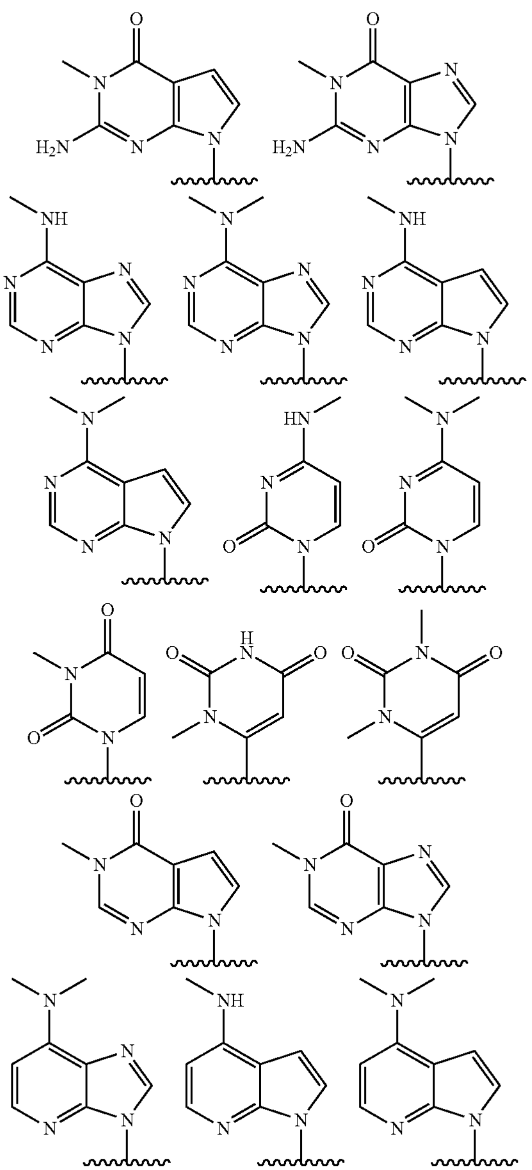

-continued

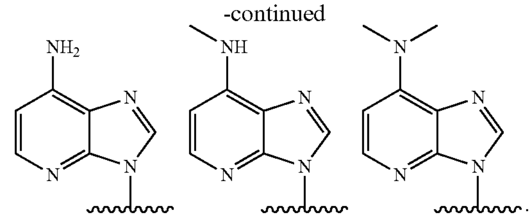

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

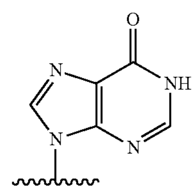

inosine

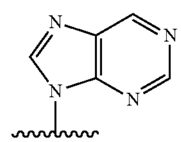

nebularine

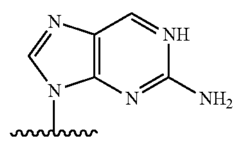

2-aminopurine

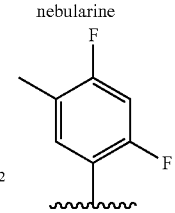

2,4-difluorotoluene

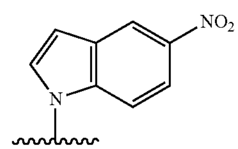

5-nitroindole

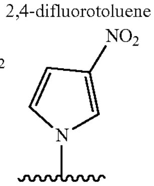

3-nitropyrrole

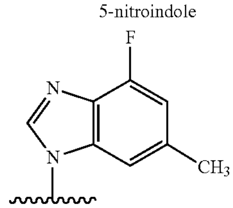

4-Fluoro-6-methylbenzimidazole

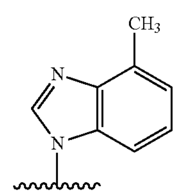

4-Methylbenzimidazole

In some embodiments, the thermally destabilizing modification of the duplex in the seed region of the antisense strand includes one or more a-nucleotide complementary to the base on the target mRNA, such as:

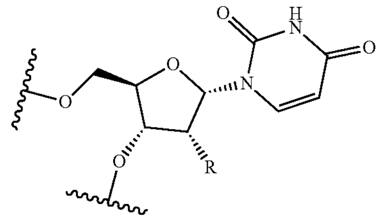

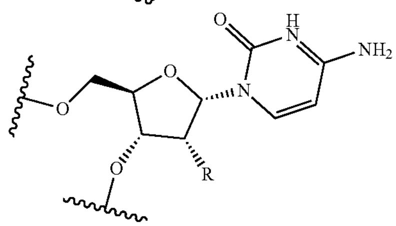

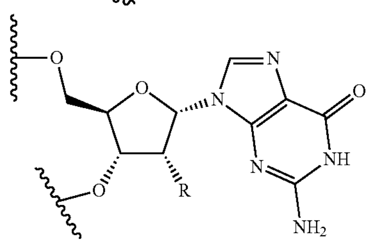

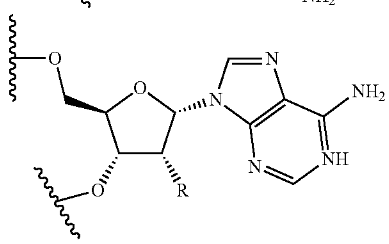

Wherein R is H, OH, $OCH_3$, F, $NH_2$, NHMe, $NMe_2$ or O-alkyl

Exemplary phosphate modifications known to decrease the thermal stability of dsRNA duplexes compared to natural phosphodiester linkages are:

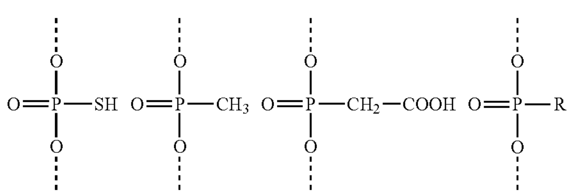

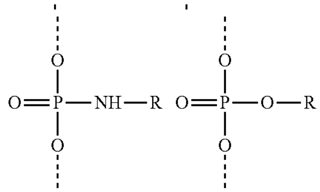

R = alkyl

The alkyl for the R group can be a $C_1$-$C_6$alkyl. Specific alkyls for the R group include, but are not limited to methyl, ethyl, propyl, isopropyl, butyl, pentyl and hexyl.

In some embodiments, exemplary destabilizing modifications shown in FIG. 1.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand and/or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14 and 16 from the 5'-end. In some other embodiments, the antisense comprises stabilizing modifications at positions 2, 6, 14 and 16 from the 5'-end. In still some other embodiments, the antisense comprises stabilizing modifications at positions 2, 14 and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification. In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10 and 11 from the 5'-end. In some other embodiments, the sense strand comprises stabilizing modifications at positions 7, 9, 10 and 11 from the 5'-end. In some embodiments, the sense strand comprises stabilizing modifications at positions opposite or complimentary to positions 11, 12 and 15 of the antisense strand, counting from the 5'-end of the antisense strand. In some other embodiments, the sense strand comprises stabilizing modifications at positions opposite or complimentary to positions 11, 12, 13 and 15 of the antisense strand, counting from the 5'-end of the antisense strand. In some embodiments, the sense strand comprises a block of two, three or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to 2'-fluoro modifications. Other thermally stabilizing modifications include, but are not limited to LNA.

In some embodiments, the dsRNA of the invention comprises at least four (e.g., four, five, six, seven, eight, nine, ten or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand and/or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14 and 16 from the 5'-end. In some other embodiments, the antisense comprises 2'-fluoro nucleotides at positions 2, 6, 14 and 16 from the 5'-end. In still some other embodiments, the antisense comprises 2'-fluoro nucleotides at positions 2, 14 and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10 and 11 from the 5'-end. In some other embodiments, the sense strand comprises 2'-fluoro nucleotides at positions 7, 9, 10 and 11 from the 5'-end. In some embodiments, the sense strand comprises 2'-fluoro nucleotides at positions opposite or complimentary to positions 11, 12 and 15 of the antisense strand, counting from the 5'-end of the antisense strand. In some other embodiments, the sense strand comprises 2'-fluoro nucleotides at positions opposite or complimentary to positions 11, 12, 13 and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

Some Selected Definitions

As used herein, the terms “dsRNA”, “siRNA”, and “iRNA agent” are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase “mediates RNAi” refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, “specifically hybridizable” and “complementary” are terms which are used to indicate a sufficient degree of complementarity such that stable and specific binding occurs between a compound of the invention and a target RNA molecule. Specific binding requires a sufficient degree of complementarity to αvoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In some embodiments, a dsRNA molecule of the invention is “sufficiently complementary” to a target RNA, e.g., a target mRNA, such that the dsRNA molecule silences production of protein encoded by the target mRNA. In another embodiment, the dsRNA molecule of the invention is “exactly complementary” to a target RNA, e.g., the target RNA and the dsRNA duplex agent anneal, for example to form a hybrid made exclusively of Watson-Crick base pairs in the region of exact complementarity. A “sufficiently complementary” target RNA can include an internal region (e.g., of at least 10 nucleotides) that is exactly complementary to a target RNA. Moreover, in some embodiments, the dsRNA molecule of the invention specifically discriminates a single-nucleotide difference. In this case, the dsRNA molecule only mediates RNAi if exact complementary is found in the region (e.g., within 7 nucleotides of) the single-nucleotide difference.

The term ‘BNA’ refers to bridged nucleic acid, and is often referred as constrained or inaccessible RNA. BNA can contain a 5-, 6-membered, or even a 7-membered bridged structure with a “fixed” C3'-endo sugar puckering. The bridge is typically incorporated at the 2'-, 4'-position of the ribose to afford a 2', 4'-BNA nucleotide (e.g., LNA, or ENA). Examples of BNA nucleotides include the following nucleosides:

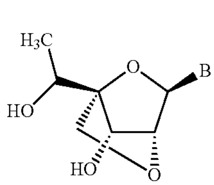
5′ Me BNA

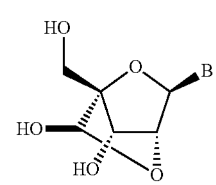
cEt BNA

-continued

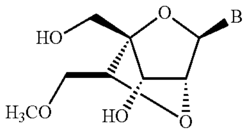

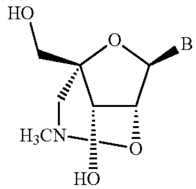

cMOE BNA oxyamino-BNA

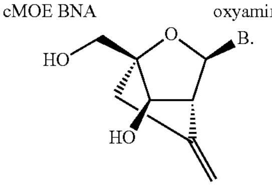

vinyl-carbo-BNA

The term INA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

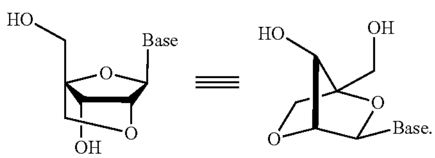

The term 'ENA' refers to ethylene-bridged nucleic acid, and is often referred as constrained or inaccessible RNA.

The "cleavage site" herein means the backbone linkage in the target gene or the sense strand that is cleaved by the RISC mechanism by utilizing the iRNA agent. And the target cleavage site region comprises at least one or at least two nucleotides on both side of the cleavage site. For the sense strand, the cleavage site is the backbone linkage in the sense strand that would get cleaved if the sense strand itself was the target to be cleaved by the RNAi mechanism. The cleavage site can be determined using methods known in the art, for example the 5'-RACE assay as detailed in Soutschek et al., *Nature* (2004) 432, 173-178, which is incorporated by reference in its entirety. As is well understood in the art, the cleavage site region for a conical double stranded RNAi agent comprising two 21-nucleotides long strands (wherein the strands form a double stranded region of 19 consecutive base pairs having 2-nucleotide single stranded overhangs at the 3'-ends), the cleavage site region corresponds to positions 9-12 from the 5'-end of the sense strand.

Cleavable Linking Groups

A cleavable linking group is one which is sufficiently stable outside the cell, but which upon entry into a target cell is cleaved to release the two parts the linker is holding together. In a preferred embodiment of the dsRNA molecule according to the present invention, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups is redox cleavable linking groups, which may be used in the dsRNA molecule according to the present invention that are cleaved upon reduction or oxidation. An example of reductively cleavable linking group is a disulfide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups, which may be used in the dsRNA molecule according to the present invention, are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)-O—, —O—P(S)(OH)-O—, —O—P(S)(SH)-O—, —S—P(O)(OH)-O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups, which may be used in the dsRNA molecule according to the present invention, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups, which may be used in the dsRNA molecule according to the present invention, are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups, which may be used in the dsRNA molecule according to the present invention, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCH$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

In Vivo Stability

For the dsRNA molecules to be more effective in vivo, the antisense strand must have some metabolic stability. In other words, for the dsRNA molecules to be more effective in vivo, some amount of the antisense stand may need to be present in vivo after a period time after administration. Accordingly, in some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 5 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 6 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 7 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 8 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 9 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 10 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 11 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 12 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 13 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 14 after in vivo administration. In some embodiments, at least 40%, for example at least 45%, at least 50%, at least 55%, at least 60%., at least 65%, at least 70%, at least 75%, or at least 80% of the antisense strand of the dsRNA is present in vivo, for example in mouse liver, at day 15 after in vivo administration.

Uses of dsRNA

The present invention further relates to a use of a dsRNA molecule as defined herein for inhibiting expression of a target gene. In some embodiments, the present invention further relates to a use of a dsRNA molecule for inhibiting expression of a target gene in vitro.

The present invention further relates to a dsRNA molecule as defined herein for use in inhibiting expression of a target gene in a subject. The subject may be any animal, such as a mammal, e.g., a mouse, a rat, a sheep, a cattle, a dog, a cat, or a human In some embodiments, the dsRNA molecule of the invention is administered in buffer.

In some embodiments, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A dsRNA preparation can be formulated in combination with another agent, e.g., another therapeutic agent or an agent that stabilizes a dsRNA, e.g., a protein that complexes with dsRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

In some embodiments, the dsRNA preparation includes another dsRNA compound, e.g., a second dsRNA that can mediate RNAi with respect to a second gene, or with respect to the same gene. Still other preparation can include at least 3, 5, ten, twenty, fifty, or a hundred or more different siRNA species. Such dsRNAs can mediate RNAi with respect to a similar number of different genes.

In some embodiments, the dsRNA preparation includes at least a second therapeutic agent (e.g., an agent other than a RNA or a DNA). For example, a dsRNA composition for the treatment of a viral disease, e.g., HIV, might include a known antiviral agent (e.g., a protease inhibitor or reverse transcriptase inhibitor). In another example, a dsRNA composition for the treatment of a cancer might further comprise a chemotherapeutic agent.

Exemplary formulations which can be used for administering the dsRNA molecule according to the present invention are discussed below.

Liposomes. A dsRNA preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the dsRNA are delivered into the cell where the dsRNA can specifically bind to a target RNA and can mediate RNAi. In some cases the liposomes are also specifically targeted, e.g., to direct the dsRNA to particular cell types.

A liposome containing a dsRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The dsRNA preparation is then added to the micelles that include the lipid component. The cationic groups on the lipid interact with the siRNA and condense around the dsRNA to form a liposome. After condensation, the detergent is removed, e.g., by dialysis, to yield a liposomal preparation of dsRNA.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984, which are incorporated by reference in their entirety. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986, which is incorporated by reference in its entirety). Microfluidization can be used when consistently small (50 to 200 nm) and relatively uniform aggregates are desired (Mayhew, et al. *Biochim. Biophys. Acta* 775:169, 1984, which is incorporated by reference in its entirety). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 19, (1992) 269-274, which is incorporated by reference in its entirety).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171,678; WO 94/00569; WO 93/24640; WO 91/16024; Felgner, J. Biol. Chem. 269:2550, 1994; Nabel, Proc. Natl. Acad. Sci. 90:11307, 1993; Nabel, Human Gene Ther. 3:649, 1992; Gershon, Biochem. 32:7143, 1993; and Strauss EMBO J. 11:417, 1992.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Felgner, P. L. et al., Proc. Natl. Acad. Sci., USA 8:7413-7417, 1987 and U.S. Pat. No. 4,897,355 for a description of DOTMA and its use with DNA, which are incorporated by reference in their entirety).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wisconsin) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991, which is incorporated by reference in its entirety). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration. Liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2, 405-410 and du Plessis et al.,

*Antiviral Research,* 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987, which are incorporated by reference in their entirety).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with dsRNA described herein are useful for treating a dermatological disorder.

Liposomes that include dsRNA described herein can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include dsRNA described herein can be delivered, for example, subcutaneously by infection in order to deliver dsRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. The dsRNA compositions can include a surfactant. In some embodiments, the dsRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, NY, 1988, p. 285).

If the surfactant molecule is not ionized, it is classified as a nonionic surfactant. Nonionic surfactants find wide application in pharmaceutical products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, NY, 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the dsRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method, a first micellar composition is prepared which contains the dsRNA composition and at least the alkali metal alkyl sulphate. The first micellar composition is then mixed with at least three micelle forming compounds to form a mixed micellar composition. In another method, the micellar composition is prepared by mixing the dsRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. In some embodiments, dsRNA preparations can be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The dsRNA agents of the invention can be formulated for pharmaceutical use. The present invention further relates to a pharmaceutical composition comprising the dsRNA molecule as defined herein. Pharmaceutically acceptable compositions comprise a therapeutically-effective amount of one or more of the dsRNA molecules in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

The dsRNA agent preparation can be formulated in combination with another agent, e.g., another therapeutic agent or an agent that stabilizes a dsRNA, e.g., a protein that complexes with the dsRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass therapy and cure. The patient receiving this treatment is any animal in need, including primates, in particular humans, and other mammals such as equines, cattle, swine and sheep; and poultry and pets in general.

Double-stranded RNA agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470, which is incorporated by reference in its entirety), or by stereotactic injection (see, e.g., Chen et al. (1994) Proc. Natl. Acad. Sci. USA 91:3054-3057, which is incorporated by reference in its entirety). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA molecule and one that produces a transcript that includes the bottom strand of a dsRNA molecule. When the templates are transcribed, the dsRNA molecule is produced, and processed into siRNA agent fragments that mediate gene silencing.

Routes of Delivery

The dsRNA molecule as defined herein or a pharmaceutical composition comprising a dsRNA molecule as defined herein can be administered to a subject using different routes of delivery. A composition that includes a dsRNA described herein can be delivered to a subject by a variety of routes. Exemplary routes include: intravenous, subcutaneous, topical, rectal, anal, vaginal, nasal, pulmonary, ocular.

The dsRNA molecule of the invention can be incorporated into pharmaceutical compositions suitable for administration. Such compositions typically include one or more species of dsRNAs and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the dsRNA in aerosol form. The vascular endothelial cells could be targeted by coating a balloon catheter with the dsRNA and mechanically introducing the dsRNA.

Dosage

In one aspect, the invention features a method of administering a dsRNA molecule, e.g., a dsRNA agent described herein, to a subject (e.g., a human subject). In another aspect, the present invention relates to a dsRNA molecule as defined herein for use in inhibiting expression of a target gene in a subject. The method or the medical use includes administering a unit dose of the dsRNA molecule, e.g., a dsRNA agent described herein. In some embodiments, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4\times10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target gene. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In some embodiments, the effective dose is administered with other traditional therapeutic modalities. In some embodiments, the subject has a viral infection and the modality is an antiviral agent other than a dsRNA molecule, e.g., other than a siRNA agent. In another embodiment, the subject has atherosclerosis and the effective dose of a dsRNA molecule, e.g., a siRNA agent, is administered in combination with, e.g., after surgical intervention, e.g., angioplasty.

In some embodiments, a subject is administered an initial dose and one or more maintenance doses of a dsRNA molecule, e.g., a siRNA agent, (e.g., a precursor, e.g., a larger dsRNA molecule which can be processed into a siRNA agent, or a DNA which encodes a dsRNA molecule, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 µg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the composition includes a plurality of dsRNA molecule species. In another embodiment, the dsRNA molecule species has sequences that are non-overlapping and non-adjacent to another species with respect to a naturally occurring target sequence. In another embodiment, the plurality of dsRNA molecule species is specific for different naturally occurring target genes. In another embodiment, the dsRNA molecule is allele specific.

The dsRNA molecules of the invention described herein can be administered to mammals, particularly large mammals such as nonhuman primates or humans in a number of ways.

In some embodiments, the administration of the dsRNA molecule, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA molecules described herein In particular embodiments, the present invention relates to the dsRNA molecules of the present invention for use in the methods described above.

Methods of Inhibiting Expression of the Target Gene

Embodiments of the invention also relate to methods for inhibiting the expression of a target gene. The method comprises the step of administering the dsRNA molecules in any of the preceding embodiments, in an amount sufficient to inhibit expression of the target gene. The present invention further relates to a use of a dsRNA molecule as defined herein for inhibiting expression of a target gene in a target cell. In a preferred embodiment, the present invention further relates to a use of a dsRNA molecule for inhibiting expression of a target gene in a target cell in vitro.

Another aspect the invention relates to a method of modulating the expression of a target gene in a cell, comprising providing to said cell a dsRNA molecule of this invention. In some embodiments, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In particular embodiments, the present invention relates to the dsRNA molecules of the present invention for use in the methods described above.

The invention is further illustrated by the following examples, which should not be construed as further limiting. The contents of all references, pending patent applications and published patents, cited throughout this application are hereby expressly incorporated by reference.

EXAMPLES

Example 1: In Vitro Study

Cell Culture and 384-Well Transfections

Hep3b cells (ATCC, Manassas, VA) were grown to near confluence at 37° C. in an atmosphere of 5% CO2 in Eagle's Minimum Essential Medium (Gibco) supplemented with 10% FBS (ATCC) before being released from the plate by trypsinization.

Transfection was performed by adding 4.9 µl of Opti-MEM plus 0.1 µl of Lipofectamine RNAiMax per well (Invitrogen, Carlsbad Calif. cat #13778-150) to 5 µl of each siRNA duplex to an individual well in a 384-well plate. The mixture was then incubated at room temperature for 20 minutes. Firty µl of complete growth media containing 5,000 Hep3b cells were then added to the siRNA mixture. Cells were incubated for 24 hours prior to RNA purification. Single dose experiments were performed at 10 nM and 0.1 nM final duplex concentration, and dose response experiments were performed using an eight-point six-fold serial dilution over a range of 10 nM to 37.5 fM.

Sequences of dsRNA agents are listed in Table 1. Additional dsRNA agents targeting an AGT mRNA are described in PCT Publication No. WO 2015/179724, the entire contents of which are incorporated herein by reference.

Total RNA Isolation Using DYNABEADS mRNA Isolation Kit (Invitrogen™, Part #: 610-12)

Cells were lysed in 75 µl of Lysis/Binding Buffer containing 3 uL of beads per well and mixed for 10 minutes on an electrostatic shaker. The washing steps were automated on a Biotek EL406, using a magnetic plate support. Beads were washed (in 90 µL) once in Buffer A, once in Buffer B, and twice in Buffer E, with aspiration steps in between. Following a final aspiration, complete 10 µL RT mixture was added to each well, as described below.

cDNA Synthesis Using ABI High Capacity cDNA Reverse Transcription Kit (Applied Biosystems, Foster City, CA, Cat #4368813)

A master mix of 1 ul 10× Buffer, 0.4 μl 25× dNTPs, 1 μl Random primers, 0.5 μl Reverse Transcriptase, 0.5 μl RNase inhibitor and 6.6 μl of $H_2O$ per reaction were added per well. Plates were sealed, agitated for 10 minutes on an electrostatic shaker, and then incubated at 37 degrees C. for 2 hours. Following this, the plates were agitated at 80 degrees C. for 8 minutes Real Time PCR Two μl of cDNA were added to a master mix containing 0.5 μl of human GAPDH TaqMan Probe (4326317E), 0.5 μl human AGT (Hs00174854m1), 2 μl nuclease-free water and 5 μl Lightcycler 480 probe master mix (Roche Cat #04887301001) per well in a 384 well plates (Roche cat #04887301001). Real time PCR was done in a LightCycler480 Real Time PCR system (Roche).

To calculate relative fold change, data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 or mock-transfected. The sense and antisense sequences of AD-1955 are: sense: cuuAcGcuGAGuAcuucGAdTsdT (SEQ ID NO: 5) and antisense UCGAAGuACUcAGCGuAAGdTsdT (SEQ ID NO: 6).

Results are Summarized in Table 2.

TABLE 1

Exemplary dsRNA agents

| Duplex Number | Target | SEQ ID NO | sOligoName | sOligoSeq |
|---|---|---|---|---|
| AD-157529.3 | hAGT | 7 | A-250551.18 | gsuscauccadCadAugagaguacaL96 |
| AD-191860.3 | hAGT | 9 | A-250551.19 | gsuscauccadCadAugagaguacaL96 |
| AD-192113.1 | hAGT | 11 | A-380001.1 | gsuscauccadCadAugagadGuacaL96 |
| AD-192114.1 | hAGT | 13 | A-250551.20 | gsuscauccadCadAugagaguacaL96 |
| AD-192115.1 | hAGT | 15 | A-250551.21 | gsuscauccadCadAugagaguacaL96 |
| AD-192116.1 | hAGT | 17 | A-250551.22 | gsuscauccadCadAugagaguacaL96 |
| AD-192117.1 | hAGT | 19 | A-250551.23 | gsuscauccadCadAugagaguacaL96 |
| AD-192118.1 | hAGT | 21 | A-250551.24 | gsuscauccadCadAugagaguacaL96 |
| AD-192119.1 | hAGT | 23 | A-380007.1 | gsuscaucdCadCadAugagaguacaL96 |
| AD-192120.1 | hAGT | 25 | A-380008.1 | gsuscadTcdCadCadAugagaguacaL96 |
| AD-157541.2 | hAGT | 27 | A-250524.11 | uscsucccacdCudTuucuucuaauL96 |
| AD-192121.1 | hAGT | 29 | A-380009.1 | uscsucccacdCudTuucuudCuaauL96 |
| AD-192122.1 | hAGT | 31 | A-250524.12 | uscsucccacdCudTuucuucuaauL96 |
| AD-192123.1 | hAGT | 33 | A-250524.13 | uscsucccacdCudTuucuucuaauL96 |
| AD-192124.1 | hAGT | 35 | A-250524.14 | uscsucccacdCudTuucuucuaauL96 |
| AD-192125.1 | hAGT | 37 | A-250524.15 | uscsucccacdCudTuucuucuaauL96 |
| AD-192126.1 | hAGT | 39 | A-250524.16 | uscsucccacdCudTuucuucuaauL96 |
| AD-192127.1 | hAGT | 41 | A-380015.1 | uscsucccdAcdCudTuucuucuaauL96 |
| AD-192128.1 | hAGT | 43 | A-380016.1 | uscsucdCcdAcdCudTuucuucuaauL96 |
| AD-157552.3 | hAGT | 45 | A-250578.52 | csascaaugadGadGuaccugugaaL96 |
| AD-192129.1 | hAGT | 47 | A-250578.53 | csascaaugadGadGuaccugugaaL96 |
| AD-192130.1 | hAGT | 49 | A-380018.1 | csascaaugadGadGuaccudGugaaL96 |
| AD-192131.1 | hAGT | 51 | A-250578.54 | csascaaugadGadGuaccugugaaL96 |
| AD-192132.1 | hAGT | 53 | A-250578.55 | csascaaugadGadGuaccugugaaL96 |
| AD-192133.1 | hAGT | 55 | A-250578.56 | csascaaugadGadGuaccugugaaL96 |
| AD-192134.1 | hAGT | 57 | A-250578.57 | csascaaugadGadGuaccugugaaL96 |
| AD-192135.1 | hAGT | 59 | A-250578.58 | csascaaugadGadGuaccugugaaL96 |
| AD-192136.1 | hAGT | 61 | A-380024.1 | csascaaudGadGadGuaccugugaaL96 |

TABLE 1-continued

| Exemplary dsRNA agents | | | | |
|---|---|---|---|---|
| AD-192137.1 | hAGT | 63 | A-380025.1 | csascadAudGadGadGuaccugugaaL96 |
| AD-157563.2 | hAGT | 65 | A-250605.12 | cscsucaacudGgdAugaagaaacuL96 |
| AD-192138.1 | hAGT | 67 | A-250605.13 | cscsucaacudGgdAugaagaaacuL96 |
| AD-192139.1 | hAGT | 69 | A-380027.1 | cscsucaacudGgdAugaagdAaacuL96 |
| AD-192140.1 | hAGT | 71 | A-250605.14 | cscsucaacudGgdAugaagaaacuL96 |
| AD-192141.1 | hAGT | 73 | A-250605.15 | cscsucaacudGgdAugaagaaacuL96 |
| AD-192142.1 | hAGT | 75 | A-250605.16 | cscsucaacudGgdAugaagaaacuL96 |
| AD-192143.1 | hAGT | 77 | A-250605.17 | cscsucaacudGgdAugaagaaacuL96 |
| AD-192144.1 | hAGT | 79 | A-250605.18 | cscsucaacudGgdAugaagaaacuL96 |
| AD-192145.1 | hAGT | 81 | A-380033.1 | cscsucaadCudGgdAugaagaaacuL96 |
| AD-192146.1 | hAGT | 83 | A-380034.1 | cscsucdAadCudGgdAugaagaaacuL96 |
| AD-157574.2 | hAGT | 85 | A-250632.18 | gscsugagaadGadTugacagguuaL96 |
| AD-192147.1 | hAGT | 87 | A-250632.19 | gscsugagaadGadTugacagguuaL96 |
| AD-192148.1 | hAGT | 89 | A-380036.1 | gscsugagaadGadTugacadGguuaL96 |
| AD-192149.1 | hAGT | 91 | A-250632.20 | gscsugagaadGadTugacagguuaL96 |
| AD-192150.1 | hAGT | 93 | A-250632.21 | gscsugagaadGadTugacagguuaL96 |
| AD-192151.1 | hAGT | 95 | A-250632.22 | gscsugagaadGadTugacagguuaL96 |
| AD-192152.1 | hAGT | 97 | A-250632.23 | gscsugagaadGadTugacagguuaL96 |
| AD-192153.1 | hAGT | 99 | A-250632.24 | gscsugagaadGadTugacagguuaL96 |
| AD-192154.1 | hAGT | 101 | A-380042.1 | gscsugagdAadGadTugacagguuaL96 |
| AD-192155.1 | hAGT | 103 | A-380043.1 | gscsugdAgdAadGadTugacagguuaL96 |
| AD-157584.2 | hAGT | 105 | A-250659.12 | uscsucacuudTcdCagcaaaacuaL96 |
| AD-192156.1 | hAGT | 107 | A-250659.13 | uscsucacuudTcdCagcaaaacuaL96 |
| AD-192157.1 | hAGT | 109 | A-380045.1 | uscsucacuudTcdCagcaadAacuaL96 |
| AD-192158.1 | hAGT | 111 | A-250659.14 | uscsucacuudTcdCagcaaaacuaL96 |
| AD-192159.1 | hAGT | 113 | A-250659.15 | uscsucacuudTcdCagcaaaacuaL96 |
| AD-192160.1 | hAGT | 115 | A-250659.16 | uscsucacuudTcdCagcaaaacuaL96 |
| AD-192161.1 | hAGT | 117 | A-250659.17 | uscsucacuudTcdCagcaaaacuaL96 |
| AD-192162.1 | hAGT | 119 | A-250659.18 | uscsucacuudTcdCagcaaaacuaL96 |
| AD-192163.1 | hAGT | 121 | A-380051.1 | uscsucacdTudTcdCagcaaaacuaL96 |
| AD-192164.1 | hAGT | 123 | A-380052.1 | uscsucdAcdTudTcdCagcaaaacuaL96 |
| AD-264555.1 | F12 | 125 | A-311744.4 | ascsucaauadAadGugcuuugaaaL96 |
| AD-264556.1 | F12 | 127 | A-492558.3 | usgscuuugadGcdCucagcuucuaL96 |
| AD-264557.1 | F12 | 129 | A-492560.2 | cscscaagaadAgdTgaaagaccaaL96 |
| AD-264558.1 | F12 | 131 | A-492562.2 | gsgsaacucadAudAaagugcuuuaL96 |
| AD-264559.1 | F12 | 133 | A-492564.2 | gscsccaagadAadGugaaagaccaL96 |
| AD-264560.1 | F12 | 135 | A-492566.2 | asgsugcuuudGadGccucagcuuaL96 |
| AD-264561.1 | F12 | 137 | A-492568.2 | uscsaauaaadGudGcuuugaaaauL96 |
| AD-264562.1 | F12 | 139 | A-492570.2 | gsasgcccaadGadAagugaaagaaL96 |

TABLE 1-continued

| Exemplary dsRNA agents | | | |
|---|---|---|---|
| AD-264563.1 F12 | 141 | A-492572.2 | usgsgagcccdAadGaaagugaaaaL96 |
| AD-264564.1 F12 | 143 | A-492574.2 | asascucaaudAadAgugcuuugaaL96 |
| AD-264565.1 F12 | 145 | A-492576.2 | gsusgcuuugdAgdCcucagcuucuL96 |
| AD-264566.1 F12 | 147 | A-492578.2 | usgsuggagcdCcdAagaaagugaaL96 |
| AD-264567.1 F12 | 149 | A-492580.2 | csuscaauaadAgdTgcuuugaaaaL96 |
| AD-264568.1 F12 | 151 | A-492582.2 | gscsuuugagdCcdTcagcuucucaL96 |
| AD-264569.1 F12 | 153 | A-492584.2 | gsusggagccdCadAgaaagugaaaL96 |
| AD-264570.1 F12 | 155 | A-492586.2 | gsgsagcccadAgdAaagugaaagaL96 |
| AD-264571.1 F12 | 157 | A-492588.2 | gsasacucaadTadAagugcuuugaL96 |
| AD-264572.1 F12 | 159 | A-492590.2 | gsgscuguggdTgdAccgcaacaaaL96 |
| AD-264573.1 F12 | 161 | A-492592.2 | asgscccaagdAadAgugaaagacaL96 |
| AD-264574.1 F12 | 163 | A-492594.2 | csasucagacdTudCucuguccaaaL96 |
| AD-264575.1 F12 | 165 | A-492596.2 | gsusgaaagadCcdAuugcagcaaaL96 |
| AD-264576.1 F12 | 167 | A-492598.2 | gsgsaaagacdTcdCaagaaauuuaL96 |
| AD-264577.1 F12 | 169 | A-492600.2 | cscsagaagcdAudAuugcuucauaL96 |
| AD-264578.1 F12 | 171 | A-492602.2 | csasuaacuadAcdCaggcuuuauaL96 |
| AD-264579.1 F12 | 173 | A-492604.2 | ascsauugccdAgdAaagagaaauaL96 |
| AD-264580.1 F12 | 175 | A-492606.2 | gsasaacucadAudAaagugcuuuaL96 |
| AD-264581.1 F12 | 177 | A-492608.2 | csascuggaudAudTuuugcgacuuL96 |
| AD-264582.1 F12 | 179 | A-492610.2 | ascsuggauadTudTuugcgacuuaL96 |
| AD-264583.1 F12 | 181 | A-492612.2 | ascsuaaccadGgdCuuuauccuuaL96 |
| AD-264584.1 F12 | 183 | A-492614.2 | asusuuugcdGadCuuggaccuuuL96 |
| AD-264585.1 F12 | 185 | A-492616.2 | csasgaagcadTadTugcuucauaaL96 |
| AD-264586.1 F12 | 187 | A-492618.2 | usgsgaaagadCudCcaagaaauuuL96 |
| AD-264587.1 F12 | 189 | A-492620.2 | usascacuggdAudAuuuuugcgaaL96 |
| AD-264588.1 F12 | 191 | A-492622.2 | gsasaagacudCcdAagaaauuuaaL96 |
| AD-264589.1 F12 | 193 | A-492624.2 | ususuuugcgdAcdTuggaccuuuaL96 |
| AD-264590.1 F12 | 195 | A-492626.2 | uscsaauaaadGudGcuuugaaaacL96 |
| AD-264591.1 F12 | 197 | A-492628.2 | csasggcuacdAcdTggauauuuuL96 |
| AD-264592.1 F12 | 199 | A-492630.2 | csasuggaaadGadCuccaagaaauL96 |
| AD-264593.1 F12 | 201 | A-492632.2 | gsascugagadAgdCaagcgcuaaaL96 |
| AD-264594.1 F12 | 203 | A-492634.2 | gsascuccaadGadAauuuaaggaaL96 |
| AD-264595.1 F12 | 205 | A-492636.2 | csasagaaagdTgdAaagaccauuaL96 |
| AD-264596.1 F12 | 207 | A-311744.5 | ascsucaauadAadGugcuuugaaaL96 |
| AD-264597.1 F12 | 209 | A-492639.2 | csusuccacgdAgdAaugagcuauaL96 |
| AD-264598.1 F12 | 211 | A-492641.2 | asascuaaccdAgdGcuuuauccuuL96 |
| AD-264599.1 F12 | 213 | A-492643.2 | gsasgucuggdAudCugacacuuuaL96 |
| AD-264600.1 F12 | 215 | A-492645.2 | gscscagaaadGadGaaaugcuuuaL96 |
| AD-264601.1 F12 | 217 | A-492558.4 | usgscuuugadGcdCucagcuucuaL96 |

TABLE 1-continued

| Exemplary dsRNA agents | | | | |
|---|---|---|---|---|
| AD-237788.1 | TTR | 219 | A-432275.2 | csusugcucudAudAaaccguguuaL96 |
| AD-237789.1 | TTR | 221 | A-432277.2 | csasguguucdTudGcucuauaaaaL96 |
| AD-237790.1 | TTR | 223 | A-432279.2 | uscsuugcucdTadTaaaccguguuL96 |
| AD-237791.1 | TTR | 225 | A-432281.2 | gsusucuugcdTcdTauaaaccguaL96 |
| AD-237792.1 | TTR | 227 | A-432283.2 | ususgcucuadTadAaccguguuaaL96 |
| AD-237793.1 | TTR | 229 | A-432285.2 | asgsuguucudTgdCucuauaaacaL96 |
| AD-237794.1 | TTR | 231 | A-432287.2 | cscsucugaudGgdTcaaaguccuaL96 |
| AD-237795.1 | TTR | 233 | A-432289.2 | asgsaacuggdAcdAccaaaucguaL96 |
| AD-237796.1 | TTR | 235 | A-432291.2 | ascsaguguudCudTgcucuauaaaL96 |
| AD-237797.1 | TTR | 237 | A-432293.2 | gsasacuggadCadCcaaaucguaaL96 |
| AD-237798.1 | TTR | 239 | A-432295.2 | csuscuauaadAcdCguguuagcaaL96 |
| AD-237799.1 | TTR | 241 | A-432297.2 | ascsuggacadCcdAaaucguacuaL96 |
| AD-237800.1 | TTR | 243 | A-432299.2 | csasggaucudTgdCcaaagcaguaL96 |
| AD-237801.1 | TTR | 245 | A-432301.2 | usgsuucuugdCudCuauaaaccguL96 |
| AD-237802.1 | TTR | 247 | A-432303.2 | csuscaccacdAgdAugagaaguuuL96 |
| AD-237803.1 | TTR | 249 | A-432305.2 | uscscucugadTgdGucaaaguccuL96 |
| AD-237804.1 | TTR | 251 | A-432307.2 | ususcuugcudCudAuaaaccguguL96 |
| AD-237805.1 | TTR | 253 | A-432309.2 | asgsgaucuudGcdCaaagcaguaaL96 |
| AD-237806.1 | TTR | 255 | A-432311.2 | gscsucuauadAadCcguguuagcaL96 |
| AD-237807.1 | TTR | 257 | A-432313.2 | csascuacacdCadTcgcagcccuaL96 |
| AD-237808.1 | TTR | 259 | A-432315.2 | usgscucuaudAadAccguguuagaL96 |
| AD-237809.1 | TTR | 261 | A-432317.2 | gsgsacaccadAadTcguacuggaaL96 |
| AD-237810.1 | TTR | 263 | A-432319.2 | cscsaggaucdTudGccaaagcaguL96 |
| AD-237811.1 | TTR | 265 | A-432321.2 | uscsgccacudAcdAccaucgcagaL96 |
| AD-237812.1 | TTR | 267 | A-432323.2 | cscscaggagdGadCcaggaucuuaL96 |
| AD-237813.1 | TTR | 269 | A-432325.2 | gsuscaaagudCcdTggaugcuguaL96 |
| AD-237814.1 | TTR | 271 | A-432327.2 | usascaccaudCgdCagcccugcuaL96 |
| AD-237815.1 | TTR | 273 | A-432329.2 | usgsgucaaadGudCcuggaugcuaL96 |
| AD-237816.1 | TTR | 275 | A-432331.2 | asasaguccudGgdAugcuguccgaL96 |
| AD-237817.1 | TTR | 277 | A-432333.2 | csusguccgadGgdCagcccugcuaL96 |
| AD-237818.1 | TTR | 279 | A-432335.2 | gsusguucuudGcdTcuauaaaccaL96 |
| AD-237819.1 | TTR | 281 | A-432337.2 | usgsauggucdAadAguccuggauaL96 |
| AD-237820.1 | TTR | 283 | A-432339.2 | cscsacuacadCcdAucgcagcccuL96 |
| AD-237821.1 | TTR | 285 | A-432341.2 | gsgsgcucacdCadCagaugagaaaL96 |
| AD-237822.1 | TTR | 287 | A-432343.2 | ascscaggaudCudTgccaaagcaaL96 |
| AD-237823.1 | TTR | 289 | A-432345.2 | cscsuggaugdCudGuccgaggcaaL96 |
| AD-237824.1 | TTR | 291 | A-432347.2 | gsgsucaaagdTcdCuggaugcuguL96 |
| AD-237825.1 | TTR | 293 | A-432349.2 | csascgggcudCadCcacagaugaaL96 |
| AD-237826.1 | TTR | 295 | A-432351.2 | gsgsaucuugdCcdAaagcaguagaL96 |

TABLE 1-continued

| Exemplary dsRNA agents | | | | |
|---|---|---|---|---|
| AD-237827.1 | TTR | 297 | A-432353.2 | gscsucaccadCadGaugagaaguuL96 |
| AD-237828.1 | TTR | 299 | A-432355.2 | csuscugaugdGudCaaaguccugaL96 |
| AD-237829.1 | TTR | 301 | A-432357.2 | csusggacacdCadAaucguacugaL96 |
| AD-237830.1 | TTR | 303 | A-432359.2 | csgsggcucadCcdAcagaugagaaL96 |
| AD-237831.1 | TTR | 305 | A-432361.2 | usgsgacaccdAadAucguacuggaL96 |
| AD-237832.1 | TTR | 307 | A-432363.2 | usgsgagagcdTgdCacgggcucaaL96 |
| AD-237833.1 | TTR | 309 | A-432365.2 | gscsccaggadGgdAccaggaucuuL96 |
| AD-237834.1 | TTR | 311 | A-432367.2 | gsgsaccaggdAudCuugccaaagaL96 |
| AD-237835.1 | TTR | 313 | A-432369.2 | usgscacgggdCudCaccacagauaL96 |
| AD-237836.1 | TTR | 315 | A-432371.2 | gsascaggaudGgdCuucccuucgaL96 |
| AD-237837.1 | TTR | 317 | A-432373.2 | csgsccacuadCadCcaucgcagcaL96 |
| AD-237838.1 | TTR | 319 | A-432375.2 | asasguccugdGadTgcuguccgaaL96 |
| AD-237839.1 | TTR | 321 | A-432377.2 | asgsuccuggdAudGcuguccgagaL96 |
| AD-237840.1 | TTR | 323 | A-432379.2 | csusgcacggdGcdTcaccacagauL96 |
| AD-237841.1 | TTR | 325 | A-432381.2 | gsasccaggadTcdTugccaaagcaL96 |
| AD-237842.1 | TTR | 327 | A-432383.2 | asascuggacdAcdCaaaucguacuL96 |
| AD-237843.1 | TTR | 329 | A-432385.2 | gsasuggucadAadGuccuggaugaL96 |
| AD-237844.1 | TTR | 331 | A-432387.2 | asusggucaadAgdTccuggaugcuL96 |
| AD-237845.1 | TTR | 333 | A-432389.2 | gscscacuacdAcdCaucgcagccaL96 |
| AD-237846.1 | TTR | 335 | A-432391.2 | usgsacaggadTgdGcuucccuucaL96 |
| AD-237847.1 | TTR | 337 | A-432393.2 | asgsagcugcdAcdGggcucaccaaL96 |
| AD-237848.1 | TTR | 339 | A-432395.2 | gsusccuggadTgdCuguccgaggaL96 |
| AD-237849.1 | TTR | 341 | A-432397.2 | asusgcugucdCgdAggcagcccuaL96 |
| AD-237850.1 | TTR | 343 | A-432399.2 | gsgsagagcudGcdAcgggcucacaL96 |
| AD-237851.1 | TTR | 345 | A-432401.2 | csusggaugcdTgdTccgaggcagaL96 |
| AD-237852.1 | TTR | 347 | A-432403.2 | ascsaccaucdGcdAgcccugcucaL96 |
| AD-237853.1 | TTR | 349 | A-432405.2 | cscsaggaggdAcdCaggaucuugaL96 |
| AD-237854.1 | TTR | 351 | A-432407.2 | ascsgggcucdAcdCacagaugagaL96 |
| AD-237855.1 | TTR | 353 | A-432409.2 | gsasucuugcdCadAagcaguagcaL96 |
| AD-237856.1 | TTR | 355 | A-432411.2 | uscsuggagadGcdTgcacgggcuaL96 |
| AD-237857.1 | TTR | 357 | A-432413.2 | gscsacgggcdTcdAccacagaugaL96 |
| AD-237858.1 | TTR | 359 | A-432415.2 | usgsgaugcudGudCcgaggcagcaL96 |
| AD-237859.1 | TTR | 361 | A-432417.2 | gsasugcugudCcdGaggcagcccuL96 |
| AD-237860.1 | TTR | 363 | A-432419.2 | gsuscuggagdAgdCugcacgggcuL96 |
| AD-237861.1 | TTR | 365 | A-432421.2 | csusggagagdCudGcacgggcucaL96 |
| AD-237862.1 | TTR | 367 | A-432423.2 | gsgscucaccdAcdAgaugagaaguL96 |
| AD-237863.1 | TTR | 369 | A-432425.2 | uscscuggaudGcdTguccgaggcaL96 |
| AD-237864.1 | TTR | 371 | A-432427.2 | gsgsaugcugdTcdCgaggcagccaL96 |
| AD-237865.1 | TTR | 373 | A-432429.2 | csasggaggadCcdAggaucuugcaL96 |

TABLE 1-continued

| Exemplary dsRNA agents | | | | |
|---|---|---|---|---|
| AD-237866.1 | TTR | 375 | A-432431.2 | gsasgagcugdCadCgggcucaccaL96 |
| AD-218795.6 | TTR | 377 | A-128292.13 | asascagugudTcdTugcucuauaaL96 |
| AD-238829.1 | TTR | 379 | A-128292.14 | asascagugudTcdTugcucuauaaL96 |
| AD-238830.1 | TTR | 381 | A-128292.15 | asascagugudTcdTugcucuauaaL96 |
| AD-238831.1 | TTR | 383 | A-128292.16 | asascagugudTcdTugcucuauaaL96 |
| AD-238832.1 | TTR | 385 | A-128292.17 | asascagugudTcdTugcucuauaaL96 |
| AD-238833.1 | TTR | 387 | A-128292.18 | asascagugudTcdTugcucuauaaL96 |
| AD-238834.1 | TTR | 389 | A-128292.19 | asascagugudTcdTugcucuauaaL96 |
| AD-238835.1 | TTR | 391 | A-128292.20 | asascagugudTcdTugcucuauaaL96 |
| AD-238836.1 | TTR | 393 | A-128292.21 | asascagugudTcdTugcucuauaaL96 |
| AD-238837.1 | TTR | 395 | A-128292.22 | asascagugudTcdTugcucuauaaL96 |
| AD-238838.1 | TTR | 397 | A-128292.23 | asascagugudTcdTugcucuauaaL96 |
| AD-238839.1 | TTR | 399 | A-128292.24 | asascagugudTcdTugcucuauaaL96 |
| AD-238840.1 | TTR | 401 | A-128292.25 | asascagugudTcdTugcucuauaaL96 |
| AD-238841.1 | TTR | 403 | A-128292.26 | asascagugudTcdTugcucuauaaL96 |
| AD-238842.1 | TTR | 405 | A-128292.27 | asascagugudTcdTugcucuauaaL96 |
| AD-238843.1 | TTR | 407 | A-128292.28 | asascagugudTcdTugcucuauaaL96 |
| AD-238844.1 | TTR | 409 | A-128292.29 | asascagugudTcdTugcucuauaaL96 |
| AD-238845.1 | TTR | 411 | A-128292.30 | asascagugudTcdTugcucuauaaL96 |
| AD-238846.1 | TTR | 413 | A-128292.31 | asascagugudTcdTugcucuauaaL96 |
| AD-238847.1 | TTR | 415 | A-128292.32 | asascagugudTcdTugcucuauaaL96 |
| AD-238848.1 | TTR | 417 | A-128292.33 | asascagugudTcdTugcucuauaaL96 |
| AD-238849.1 | TTR | 419 | A-128292.34 | asascagugudTcdTugcucuauaaL96 |
| AD-238850.1 | TTR | 421 | A-128292.35 | asascagugudTcdTugcucuauaaL96 |
| AD-238851.1 | TTR | 423 | A-128292.36 | asascagugudTcdTugcucuauaaL96 |
| AD-238852.1 | TTR | 425 | A-128292.37 | asascagugudTcdTugcucuauaaL96 |
| AD-238853.1 | TTR | 427 | A-128292.38 | asascagugudTcdTugcucuauaaL96 |
| AD-238854.1 | TTR | 429 | A-128292.39 | asascagugudTcdTugcucuauaaL96 |
| AD-238855.1 | TTR | 431 | A-128292.40 | asascagugudTcdTugcucuauaaL96 |
| AD-238856.1 | TTR | 433 | A-128292.41 | asascagugudTcdTugcucuauaaL96 |
| AD-238857.1 | TTR | 435 | A-128292.42 | asascagugudTcdTugcucuauaaL96 |
| AD-238858.1 | TTR | 437 | A-128292.43 | asascagugudTcdTugcucuauaaL96 |
| AD-238859.1 | TTR | 439 | A-128292.44 | asascagugudTcdTugcucuauaaL96 |
| AD-238860.1 | TTR | 441 | A-128292.45 | asascagugudTcdTugcucuauaaL96 |
| AD-238861.1 | TTR | 443 | A-463210.1 | asascadGudGudTcdTugcucuauaaL96 |
| AD-238862.1 | TTR | 445 | A-463211.1 | asascagdTdGudTcdTugcucuauaaL96 |
| AD-238863.1 | TTR | 447 | A-463212.1 | (idTs)asascagugudTcdTugcucuauaaL96 |
| AD-192134.4 | AGT | 449 | A-250578.65 | csascaaugadGadGuaccugugaaL96 |
| AD-157553.2 | AGT | 451 | A-250578.66 | csascaaugadGadGuaccugugaaL96 |

TABLE 1-continued

| Exemplary dsRNA agents | | | | |
|---|---|---|---|---|
| AD-238872.1 | AGT | 453 | A-250578.67 | csascaaugadGadGuaccugugaaL96 |
| AD-238873.1 | AGT | 455 | A-250578.68 | csascaaugadGadGuaccugugaaL96 |
| AD-238874.1 | AGT | 457 | A-250578.69 | csascaaugadGadGuaccugugaaL96 |
| AD-238875.1 | AGT | 459 | A-250578.70 | csascaaugadGadGuaccugugaaL96 |
| AD-238876.1 | AGT | 461 | A-250578.71 | csascaaugadGadGuaccugugaaL96 |
| AD-192129.4 | AGT | 463 | A-250578.72 | csascaaugadGadGuaccugugaaL96 |
| AD-238877.1 | AGT | 465 | A-250578.73 | csascaaugadGadGuaccugugaaL96 |
| AD-157552.4 | AGT | 467 | A-250578.74 | csascaaugadGadGuaccugugaaL96 |
| AD-238878.1 | AGT | 469 | A-250578.75 | csascaaugadGadGuaccugugaaL96 |
| AD-238879.1 | AGT | 471 | A-250578.76 | csascaaugadGadGuaccugugaaL96 |
| AD-238880.1 | AGT | 473 | A-250578.77 | csascaaugadGadGuaccugugaaL96 |
| AD-192135.2 | AGT | 475 | A-250578.78 | csascaaugadGadGuaccugugaaL96 |
| AD-238881.1 | AGT | 477 | A-250578.79 | csascaaugadGadGuaccugugaaL96 |
| AD-238882.1 | AGT | 479 | A-250578.80 | csascaaugadGadGuaccugugaaL96 |
| AD-238883.1 | AGT | 481 | A-250578.81 | csascaaugadGadGuaccugugaaL96 |
| AD-238884.1 | AGT | 483 | A-250578.82 | csascaaugadGadGuaccugugaaL96 |
| AD-238885.1 | AGT | 485 | A-250578.83 | csascaaugadGadGuaccugugaaL96 |
| AD-238886.1 | AGT | 487 | A-250578.84 | csascaaugadGadGuaccugugaaL96 |
| AD-238887.1 | AGT | 489 | A-250578.85 | csascaaugadGadGuaccugugaaL96 |
| AD-238888.1 | AGT | 491 | A-250578.86 | csascaaugadGadGuaccugugaaL96 |
| AD-238889.1 | AGT | 493 | A-250578.87 | csascaaugadGadGuaccugugaaL96 |
| AD-238890.1 | AGT | 495 | A-250578.88 | csascaaugadGadGuaccugugaaL96 |
| AD-238891.1 | AGT | 497 | A-250578.89 | csascaaugadGadGuaccugugaaL96 |
| AD-238892.1 | AGT | 499 | A-250578.90 | csascaaugadGadGuaccugugaaL96 |
| AD-238893.1 | AGT | 501 | A-250578.91 | csascaaugadGadGuaccugugaaL96 |
| AD-238894.1 | AGT | 503 | A-250578.92 | csascaaugadGadGuaccugugaaL96 |
| AD-238895.1 | AGT | 505 | A-250578.93 | csascaaugadGadGuaccugugaaL96 |
| AD-238896.1 | AGT | 507 | A-250578.94 | csascaaugadGadGuaccugugaaL96 |
| AD-238897.1 | AGT | 509 | A-250578.95 | csascaaugadGadGuaccugugaaL96 |
| AD-238898.1 | AGT | 511 | A-250578.96 | csascaaugadGadGuaccugugaaL96 |
| AD-238899.1 | AGT | 513 | A-250578.97 | csascaaugadGadGuaccugugaaL96 |
| AD-238900.1 | AGT | 515 | A-380025.2 | csascadAudGadGadGuaccugugaaL96 |
| AD-238901.1 | AGT | 517 | A-463249.1 | csascaadTdGadGadGuaccugugaaL96 |
| AD-238902.1 | AGT | 519 | A-463250.1 | (idTs)csascaaugadGadGuaccugugaaL96 |
| AD-264561.2 | F12 | 521 | A-492568.3 | uscsaauaaadGudGcuuugaaaauL96 |
| AD-273421.1 | F12 | 523 | A-529077.1 | uscsdAauaaadGudGcuuugaaaauL96 |
| AD-273422.1 | F12 | 525 | A-529078.1 | uscsadAuaaadGudGcuuugaaaauL96 |
| AD-273423.1 | F12 | 527 | A-529079.1 | uscsaadTaaadGudGcuuugaaaauL96 |
| AD-273424.1 | F12 | 529 | A-529080.1 | uscsaaudAaadGudGcuuugaaaauL96 |

TABLE 1-continued

| Exemplary dsRNA agents | | | | |
|---|---|---|---|---|
| AD-273425.1 | F12 | 531 | A-529081.1 | uscsaauadAadGudGcuuugaaaauL96 |
| AD-273426.1 | F12 | 533 | A-529082.1 | uscsaauaadAdGudGcuuugaaaauL96 |
| AD-273427.1 | F12 | 535 | A-172952.2 | uscsaauaaagudGcuuugaaaauL96 |
| AD-273428.1 | F1.2 | 537 | A-529083.1 | uscsaauaaadGdTdGcuuugaaaauL96 |
| AD-273429.1 | F1.2 | 539 | A-529084.1 | uscsaauaaadGugcuuugaaaauL96 |
| AD-273430.1 | F1.2 | 541 | A-529085.1 | uscsaauaaadGudGdCuuugaaaauL96 |
| AD-273431.1 | E12 | 543 | A-529086.1 | uscsaauaaadGudGcdTuugaaaauL96 |
| AD-273432.1 | E12 | 545 | A-529087.1 | uscsaauaaadGudGcudTugaaaauL96 |
| AD-273433.1 | E12 | 547 | A-529088.1 | uscsaauaaadGudGcuudTgaaaauL96 |
| AD-273434.1 | E12 | 549 | A-529089.1 | uscsaauaaadGudGcuuudGaaaauL96 |
| AD-273435.1 | E12 | 551 | A-529090.1 | uscsaauaaadGudGcuuugdAaaauL96 |
| AD-273436.1 | E12 | 553 | A-529091.1 | uscsaauaaadGudGcuuugadAaauL96 |
| AD-273437.1 | E12 | 555 | A-529092.1 | uscsaauaaadGudGcuuugaadAauL96 |
| AD-273438.1 | E12 | 557 | A-529093.1 | uscsaauaaadGudGcuuugaaadAuL96 |
| AD-273439.1 | E12 | 559 | A-492568.4 | uscsaauaaadGudGcuuugaaaauL96 |
| AD-273440.1 | E12 | 561 | A-492568.5 | uscsaauaaadGudGcuuugaaaauL96 |
| AD-273441.1 | E12 | 563 | A-492568.6 | uscsaauaaadGudGcuuugaaaauL96 |
| AD-273442.1 | E12 | 565 | A-492568.7 | uscsaauaaadGudGcuuugaaaauL96 |
| AD-273443.1 | E12 | 567 | A-492568.8 | uscsaauaaadGudGcuuugaaaauL96 |
| AD-273444.1 | E12 | 569 | A-492568.9 | uscsaauaaadGudGcuuugaaaauL96 |
| AD-273445.1 | E12 | 571 | A-492568.10 | uscsaauaaadGudGcuuugaaaauL96 |
| AD-273446.1 | E12 | 573 | A-492568.11 | uscsaauaaadGudGcuuugaaaauL96 |
| AD-273447.1 | E12 | 575 | A-492568.12 | uscsaauaaadGudGcuuugaaaauL96 |
| AD-273448.1 | E12 | 577 | A-492568.13 | uscsaauaaadGudGcuuugaaaauL96 |
| AD-273449.1 | E12 | 579 | A-492568.14 | uscsaauaaadGudGcuuugaaaauL96 |
| AD-273450.1 | E12 | 581 | A-492568.15 | uscsaauaaadGudGcuuugaaaauL96 |
| AD-273451.1 | E12 | 583 | A-492568.16 | uscsaauaaadGudGcuuugaaaauL96 |
| AD-273452.1 | E12 | 585 | A-492568.17 | uscsaauaaadGudGcuuugaaaauL96 |
| AD-273453.1 | E12 | 587 | A-492568.18 | uscsaauaaadGudGcuuugaaaauL96 |
| AD-273454.1 | E12 | 589 | A-492568.19 | uscsaauaaadGudGcuuugaaaauL96 |
| AD-273455.1 | E12 | 591 | A-492568.20 | uscsaauaaadGudGcuuugaaaauL96 |
| AD-273456.1 | E12 | 593 | A-492568.21 | uscsaauaaadGudGcuuugaaaauL96 |
| AD-264567.2 | E12 | 595 | A-492580.3 | csuscaauaadAgdTgcuuugaaaaL96 |
| AD-273457.1 | F1.2 | 597 | A-529112.1 | csusdCaauaadAgdTgcuuugaaaaL96 |
| AD-273458.1 | F1.2 | 599 | A-529113.1 | csuscdAauaadAgdTgcuuugaaaaL96 |
| AD-273459.1 | F1.2 | 601 | A-529114.1 | csuscadAuaadAgdTgcuuugaaaaL96 |
| AD-273460.1 | E12 | 603 | A-529115.1 | csuscaadTaadAgdTgcuuugaaaaL96 |
| AD-273461.1 | E12 | 605 | A-529116.1 | csuscaaudAadAgdTgcuuugaaaaL96 |
| AD-273462.1 | E12 | 607 | A-529117.1 | csuscaauadAdAgdTgcuuugaaaaL96 |

TABLE 1-continued

| Exemplary dsRNA agents | | | | |
|---|---|---|---|---|
| AD-273463.1 | E12 | 609 | A-172964.2 | csuscaauaaagdTgcuuugaaaaL96 |
| AD-273464.1 | E12 | 611 | A-529118.1 | csuscaauaadAdGdTgcuuugaaaaL96 |
| AD-273465.1 | E12 | 613 | A-529119.1 | csuscaauaadAgugcuuugaaaaL96 |
| AD-273466.1 | E12 | 615 | A-529120.1 | csuscaauaadAgdTdGcuuugaaaaL96 |
| AD-273467.1 | E12 | 617 | A-529121.1 | csuscaauaadAgdTgdCuuugaaaaL96 |
| AD-273468.1 | E12 | 619 | A-529122.1 | csuscaauaadAgdTgcdTuugaaaaL96 |
| AD-273469.1 | E12 | 621 | A-529123.1 | csuscaauaadAgdTgcudTugaaaaL96 |
| AD-273470.1 | E12 | 623 | A-529124.1 | csuscaauaadAgdTgcuudTgaaaaL96 |
| AD-273471.1 | E12 | 625 | A-529125.1 | csuscaauaadAgdTgcuuudGaaaaL96 |
| AD-273472.1 | E12 | 627 | A-529126.1 | csuscaauaadAgdTgcuuugdAaaaL96 |
| AD-273473.1 | E12 | 629 | A-529127.1 | csuscaauaadAgdTgcuuugadAaaL96 |
| AD-273474.1 | E12 | 631 | A-529128.1 | csuscaauaadAgdTgcuuugaadAaL96 |
| AD-273475.1 | E12 | 633 | A-492580.4 | csuscaauaadAgdTgcuuugaaaaL96 |
| AD-273476.1 | E12 | 635 | A-492580.5 | csuscaauaadAgdTgcuuugaaaaL96 |
| AD-273477.1 | E12 | 637 | A-492580.6 | csuscaauaadAgdTgcuuugaaaaL96 |
| AD-273478.1 | E12 | 639 | A-492580.7 | csuscaauaadAgdTgcuuugaaaaL96 |
| AD-273479.1 | E12 | 641 | A-492580.8 | csuscaauaadAgdTgcuuugaaaaL96 |
| AD-273480.1 | E12 | 643 | A-492580.9 | csuscaauaadAgdTgcuuugaaaaL96 |
| AD-273481.1 | E12 | 645 | A-492580.10 | csuscaauaadAgdTgcuuugaaaaL96 |
| AD-273482.1 | E12 | 647 | A-492580.11 | csuscaauaadAgdTgcuuugaaaaL96 |
| AD-273483.1 | E12 | 649 | A-492580.12 | csuscaauaadAgdTgcuuugaaaaL96 |
| AD-273484.1 | E12 | 651 | A-492580.13 | csuscaauaadAgdTgcuuugaaaaL96 |
| AD-273485.1 | E12 | 653 | A-492580.14 | csuscaauaadAgdTgcuuugaaaaL96 |
| AD-273486.1 | E12 | 655 | A-492580.15 | csuscaauaadAgdTgcuuugaaaaL96 |
| AD-273487.1 | F1.2 | 657 | A-492580.16 | csuscaauaadAgdTgcuuugaaaaL96 |
| AD-273488.1 | F1.2 | 659 | A-492580.17 | csuscaauaadAgdTgcuuugaaaaL96 |
| AD-273489.1 | F1.2 | 661 | A-492580.18 | csuscaauaadAgdTgcuuugaaaaL96 |
| AD-273490.1 | E12 | 663 | A-492580.19 | csuscaauaadAgdTgcuuugaaaaL96 |
| AD-273491.1 | E12 | 665 | A-492580.20 | csuscaauaadAgdTgcuuugaaaaL96 |
| AD-273492.1 | E12 | 667 | A-492580.21 | csuscaauaadAgdTgcuuugaaaaL96 |
| AD-238841.2 | TTR | 669 | A-128292.48 | asascagugudTcdTugcucuauaaL96 |
| AD-273493.1 | TTR | 671 | A-529147.1 | asasdCagugudTcdTugcucuauaaL96 |
| AD-273494.1 | TTR | 673 | A-529148.1 | asascdAgugudTcdTugcucuauaaL96 |
| AD-273495.1 | TTR | 675 | A-529149.1 | asascadGugudTcdTugcucuauaaL96 |
| AD-273496.1 | TTR | 677 | A-529150.1 | asascagdTgudTcdTugcucuauaaL96 |
| AD-273497.1 | TTR | 679 | A-529151.1 | asascagudGudTcdTugcucuauaaL96 |
| AD-273498.1 | TTR | 681 | A-529152.1 | asascagugdTdTcdTugcucuauaaL96 |
| AD-273499.1 | TTR | 683 | A-123259.13 | asascaguguucdTugcucuauaaL96 |
| AD-273500.1 | TTR | 685 | A-529153.1 | asascagugudTdCdTugcucuauaaL96 |

TABLE 1-continued

| Exemplary dsRNA agents | | | | |
|---|---|---|---|---|
| AD-273501.1 | TTR | 687 | A-529154.1 | asascagugudTcuugcucuauaaL96 |
| AD-273502.1 | TTR | 689 | A-529155.1 | asascagugudTcdTdTgcucuauaaL96 |
| AD-273503.1 | TTR | 691 | A-529156.1 | asascagugudTcdTudGcucuauaaL96 |
| AD-273504.1 | TTR | 693 | A-529157.1 | asascagugudTcdTugdCucuauaaL96 |
| AD-273505.1 | TTR | 695 | A-529158.1 | asascagugudTcdTugcdTcuauaaL96 |
| AD-273506.1 | TTR | 697 | A-529159.1 | asascagugudTcdTugcudCuauaaL96 |
| AD-273507.1 | TTR | 699 | A-529160.1 | asascagugudTcdTugcucdTauaaL96 |
| AD-273508.1 | TTR | 701 | A-529161.1 | asascagugudTcdTugcucudAuaaL96 |
| AD-273509.1 | TTR | 703 | A-529162.1 | asascagugudTcdTugcucuadTaaL96 |
| AD-273510.1 | TTR | 705 | A-529163.1 | asascagugudTcdTugcucuaudAaL96 |
| AD-238857.2 | TTR | 707 | A-128292.49 | asascagugudTcdTugcucuauaaL96 |
| AD-238858.2 | TTR | 709 | A-128292.50 | asascagugudTcdTugcucuauaaL96 |
| AD-238837.2 | TTR | 711 | A-128292.51 | asascagugudTcdTugcucuauaaL96 |
| AD-238859.2 | TTR | 713 | A-128292.52 | asascagugudTcdTugcucuauaaL96 |
| AD-238835.2 | TTR | 715 | A-128292.53 | asascagugudTcdTugcucuauaaL96 |
| AD-238860.2 | TTR | 717 | A-128292.54 | asascagugudTcdTugcucuauaaL96 |
| AD-238834.2 | TTR | 719 | A-128292.55 | asascagugudTcdTugcucuauaaL96 |
| AD-273511.1 | TTR | 721 | A-128292.56 | asascagugudTcdTugcucuauaaL96 |
| AD-273512.1 | TTR | 723 | A-128292.57 | asascagugudTcdTugcucuauaaL96 |
| AD-273513.1 | TTR | 725 | A-128292.58 | asascagugudTcdTugcucuauaaL96 |
| AD-273514.1 | TTR | 727 | A-128292.59 | asascagugudTcdTugcucuauaaL96 |
| AD-273515.1 | TTR | 729 | A-128292.60 | asascagugudTcdTugcucuauaaL96 |
| AD-273516.1 | TTR | 731 | A-128292.61 | asascagugudTcdTugcucuauaaL96 |
| AD-238854.2 | TTR | 733 | A-128292.62 | asascagugudTcdTugcucuauaaL96 |
| AD-273517.1 | TTR | 735 | A-128292.63 | asascagugudTcdTugcucuauaaL96 |
| AD-273518.1 | TTR | 737 | A-128292.64 | asascagugudTcdTugcucuauaaL96 |
| AD-273519.1 | TTR | 739 | A-128292.65 | asascagugudTcdTugcucuauaaL96 |
| AD-273520.1 | TTR | 741 | A-128292.66 | asascagugudTcdTugcucuauaaL96 |
| AD-237793.2 | TTR | 743 | A-432285.3 | asgsuguucudTgdCucuauaaacaL96 |
| AD-273521.1 | TTR | 745 | A-529174.1 | asgsdTguucudTgdCucuauaaacaL96 |
| AD-273522.1 | TTR | 747 | A-529175.1 | asgsudGuucudTgdCucuauaaacaL96 |
| AD-273523.1 | TTR | 749 | A-529176.1 | asgsugdTucudTgdCucuauaaacaL96 |
| AD-273524.1 | TTR | 751 | A-529177.1 | asgsugudTcudTgdCucuauaaacaL96 |
| AD-273525.1 | TTR | 753 | A-529178.1 | asgsuguudCudTgdCucuauaaacaL96 |
| AD-273526.1 | TTR | 755 | A-529179.1 | asgsuguucdTdTgdCucuauaaacaL96 |
| AD-273527.1 | TTR | 757 | A-529180.1 | asgsuguucuugdCucuauaaacaL96 |
| AD-273528.1 | TTR | 759 | A-529181.1 | asgsuguucudTdGdCucuauaaacaL96 |
| AD-273529.1 | TTR | 761 | A-529182.1 | asgsuguucudTgcucuauaaacaL96 |
| AD-273530.1 | TTR | 763 | A-529183.1 | asgsuguucudTgdCdTcuauaaacaL96 |

TABLE 1-continued

| Exemplary dsRNA agents | | | | |
|---|---|---|---|---|
| AD-273531.1 | TTR | 765 | A-529184.1 | asgsuguucudTgdCudCuauaaacaL96 |
| AD-273532.1 | TTR | 767 | A-529185.1 | asgsuguucudTgdCucdTauaaacaL96 |
| AD-273533.1 | TTR | 769 | A-529186.1 | asgsuguucudTgdCucudAuaaacaL96 |
| AD-273534.1 | TTR | 771 | A-529187.1 | asgsuguucudTgdCucuadTaaacaL96 |
| AD-273535.1 | TTR | 773 | A-529188.1 | asgsuguucudTgdCucuaudAaacaL96 |
| AD-273536.1 | TTR | 775 | A-529189.1 | asgsuguucudTgdCucuauadAacaL96 |
| AD-273537.1 | TTR | 777 | A-529190.1 | asgsuguucudTgdCucuauaadAcaL96 |
| AD-273538.1 | TTR | 779 | A-529191.1 | asgsuguucudTgdCucuauaaadCaL96 |
| AD-273539.1 | TTR | 781 | A-432285.4 | asgsuguucudTgdCucuauaaacaL96 |
| AD-273540.1 | TTR | 783 | A-432285.5 | asgsuguucudTgdCucuauaaacaL96 |
| AD-273541.1 | TTR | 785 | A-432285.6 | asgsuguucudTgdCucuauaaacaL96 |
| AD-273542.1 | TTR | 787 | A-432285.7 | asgsuguucudTgdCucuauaaacaL96 |
| AD-273543.1 | TTR | 789 | A-432285.8 | asgsuguucudTgdCucuauaaacaL96 |
| AD-273544.1 | TTR | 791 | A-432285.9 | asgsuguucudTgdCucuauaaacaL96 |
| AD-273545.1 | TTR | 793 | A-432285.10 | asgsuguucudTgdCucuauaaacaL96 |
| AD-273546.1 | TTR | 795 | A-432285.11 | asgsuguucudTgdCucuauaaacaL96 |
| AD-273547.1 | TTR | 797 | A-432285.12 | asgsuguucudTgdCucuauaaacaL96 |
| AD-273548.1 | TTR | 799 | A-432285.13 | asgsuguucudTgdCucuauaaacaL96 |
| AD-273549.1 | TTR | 801 | A-432285.14 | asgsuguucudTgdCucuauaaacaL96 |
| AD-273550.1 | TTR | 803 | A-432285.15 | asgsuguucudTgdCucuauaaacaL96 |
| AD-273551.1 | TTR | 805 | A-432285.16 | asgsuguucudTgdCucuauaaacaL96 |
| AD-273552.1 | TTR | 807 | A-432285.17 | asgsuguucudTgdCucuauaaacaL96 |
| AD-273553.1 | TTR | 809 | A-432285.18 | asgsuguucudTgdCucuauaaacaL96 |
| AD-273554.1 | TTR | 811 | A-432285.19 | asgsuguucudTgdCucuauaaacaL96 |
| AD-273555.1 | TTR | 813 | A-432285.20 | asgsuguucudTgdCucuauaaacaL96 |
| AD-273556.1 | TTR | 815 | A-432285.21 | asgsuguucudTgdCucuauaaacaL96 |
| AD-273557.1 | C5 | 817 | A-529210.1 | usgsacaaaadTadAcucacuauaaL96 |
| AD-273558.1 | C5 | 819 | A-529212.1 | usgsdAcaaaadTadAcucacuauaaL96 |
| AD-273559.1 | C5 | 821 | A-529213.1 | usgsadCaaaadTadAcucacuauaaL96 |
| AD-273560.1 | C5 | 823 | A-529214.1 | usgsacdAaaadTadAcucacuauaaL96 |
| AD-273561.1 | C5 | 825 | A-529215.1 | usgsacadAaadTadAcucacuauaaL96 |
| AD-273562.1 | C5 | 827 | A-529216.1 | usgsacaadAadTadAcucacuauaaL96 |
| AD-273563.1 | C5 | 829 | A-529217.1 | usgsacaaadAdTadAcucacuauaaL96 |
| AD-273564.1 | C5 | 831 | A-529218.1 | usgsacaaaauadAcucacuauaaL96 |
| AD-273565.1 | C5 | 833 | A-529219.1 | usgsacaaaadTdAdAcucacuauaaL96 |
| AD-273566.1 | C5 | 835 | A-529220.1 | usgsacaaaadTaacucacuauaaL96 |
| AD-273567.1 | C5 | 837 | A-529221.1 | usgsacaaaadTadAdCucacuauaaL96 |
| AD-273568.1 | C5 | 839 | A-529222.1 | usgsacaaaadTadAcdTcacuauaaL96 |
| AD-273569.1 | C5 | 841 | A-529223.1 | usgsacaaaadTadAcudCacuauaaL96 |

TABLE 1-continued

| Exemplary dsRNA agents | | | | |
|---|---|---|---|---|
| AD-273570.1 | C5 | 843 | A-529224.1 | usgsacaaaadTadAcucdAcuauaaL96 |
| AD-273571.1 | C5 | 845 | A-529225.1 | usgsacaaaadTadAcucadCuauaaL96 |
| AD-273572.1 | C5 | 847 | A-529226.1 | usgsacaaaadTadAcucacdTauaaL96 |
| AD-273573.1 | C5 | 849 | A-529227.1 | usgsacaaaadTadAcucacudAuaaL96 |
| AD-273574.1 | C5 | 851 | A-529228.1 | usgsacaaaadTadAcucacuadTaaL96 |
| AD-273575.1 | C5 | 853 | A-529229.1 | usgsacaaaadTadAcucacuaudAaL96 |
| AD-273576.1 | C5 | 855 | A-529210.2 | usgsacaaaadTadAcucacuauaaL96 |
| AD-273577.1 | C5 | 857 | A-529210.3 | usgsacaaaadTadAcucacuauaaL96 |
| AD-273578.1 | C5 | 859 | A-529210.4 | usgsacaaaadTadAcucacuauaaL96 |
| AD-273579.1 | C5 | 861 | A-529210.5 | usgsacaaaadTadAcucacuauaaL96 |
| AD-273580.1 | C5 | 863 | A-529210.6 | usgsacaaaadTadAcucacuauaaL96 |
| AD-273581.1 | C5 | 865 | A-529210.7 | usgsacaaaadTadAcucacuauaaL96 |
| AD-273582.1 | C5 | 867 | A-529210.8 | usgsacaaaadTadAcucacuauaaL96 |
| AD-273583.1 | C5 | 869 | A-529210.9 | usgsacaaaadTadAcucacuauaaL96 |
| AD-273584.1 | C5 | 871 | A-529210.10 | usgsacaaaadTadAcucacuauaaL96 |
| AD-273585.1 | C5 | 873 | A-529210.11 | usgsacaaaadTadAcucacuauaaL96 |
| AD-273586.1 | C5 | 875 | A-529210.12 | usgsacaaaadTadAcucacuauaaL96 |
| AD-273587.1 | C5 | 877 | A-529210.13 | usgsacaaaadTadAcucacuauaaL96 |
| AD-273588.1 | C5 | 879 | A-529210.14 | usgsacaaaadTadAcucacuauaaL96 |
| AD-273589.1 | C5 | 881 | A-529210.15 | usgsacaaaadTadAcucacuauaaL96 |
| AD-273590.1 | C5 | 883 | A-529210.16 | usgsacaaaadTadAcucacuauaaL96 |
| AD-273591.1 | C5 | 885 | A-529210.17 | usgsacaaaadTadAcucacuauaaL96 |
| AD-273592.1 | C5 | 887 | A-529210.18 | usgsacaaaadTadAcucacuauaaL96 |
| AD-273593.1 | C5 | 889 | A-529210.19 | usgsacaaaadTadAcucacuauaaL96 |
| AD-273594.1 | C5 | 891 | A-529248.1 | asasgcaagadTadTuuuuauaaauaL96 |
| AD-273595.1 | C5 | 893 | A-529250.1 | asasdGcaagadTadTuuuuauaaauaL96 |
| AD-273596.1 | C5 | 895 | A-529251.1 | asasgdCaagadTadTuuuuauaaauaL96 |
| AD-273597.1 | C5 | 897 | A-529252.1 | asasgcdAagadTadTuuuuauaaauaL96 |
| AD-273598.1 | C5 | 899 | A-529253.1 | asasgcadAgadTadTuuuuauaaauaL96 |
| AD-273599.1 | C5 | 901 | A-529254.1 | asasgcaadGadTadTuuuuauaaauaL96 |
| AD-273600.1 | C5 | 903 | A-529255.1 | asasgcaagdAdTadTuuuuauaaauaL96 |
| AD-273601.1 | C5 | 905 | A-125131.2 | asasgcaagauadTuuuuauaaauaL96 |
| AD-273602.1 | C5 | 907 | A-529256.1 | asasgcaagadTdAdTuuuuauaaauaL96 |
| AD-273603.1 | C5 | 909 | A-529257.1 | asasgcaagadTauuuuuauaaauaL96 |
| AD-273604.1 | C5 | 911 | A-529258.1 | asasgcaagadTadTdTuuuauaaauaL96 |
| AD-273605.1 | C5 | 913 | A-529259.1 | asasgcaagadTadTudTuuauaaauaL96 |
| AD-273606.1 | C5 | 915 | A-529260.1 | asasgcaagadTadTuudTuauaaauaL96 |
| AD-273607.1 | C5 | 917 | A-529261.1 | asasgcaagadTadTuuudTauaaauaL96 |
| AD-273608.1 | C5 | 919 | A-529262.1 | asasgcaagadTadTuuuudAuaaauaL96 |

TABLE 1-continued

| Exemplary dsRNA agents | | | | |
|---|---|---|---|---|
| AD-273609.1 | C5 | 921 | A-529263.1 | asasgcaagadTadTuuuuadTaauaL96 |
| AD-273610.1 | C5 | 923 | A-529264.1 | asasgcaagadTadTuuuuaudAauaL96 |
| AD-273611.1 | C5 | 925 | A-529265.1 | asasgcaagadTadTuuuuauadAuaL96 |
| AD-273612.1 | C5 | 927 | A-529266.1 | asasgcaagadTadTuuuuauaadTaL96 |
| AD-273613.1 | C5 | 929 | A-529248.2 | asasgcaagadTadTuuuuauaauaL96 |
| AD-273614.1 | C5 | 931 | A-529248.3 | asasgcaagadTadTuuuuauaauaL96 |
| AD-273615.1 | C5 | 933 | A-529248.4 | asasgcaagadTadTuuuuauaauaL96 |
| AD-273616.1 | C5 | 935 | A-529248.5 | asasgcaagadTadTuuuuauaauaL96 |
| AD-273617.1 | C5 | 937 | A-529248.6 | asasgcaagadTadTuuuuauaauaL96 |
| AD-273618.1 | C5 | 939 | A-529248.7 | asasgcaagadTadTuuuuauaauaL96 |
| AD-273619.1 | C5 | 941 | A-529248.8 | asasgcaagadTadTuuuuauaauaL96 |
| AD-273620.1 | C5 | 943 | A-529248.9 | asasgcaagadTadTuuuuauaauaL96 |
| AD-273621.1 | C5 | 945 | A-529248.10 | asasgcaagadTadTuuuuauaauaL96 |
| AD-273622.1 | C5 | 947 | A-529248.11 | asasgcaagadTadTuuuuauaauaL96 |
| AD-273623.1 | C5 | 949 | A-529248.12 | asasgcaagadTadTuuuuauaauaL96 |
| AD-273624.1 | C5 | 951 | A-529248.13 | asasgcaagadTadTuuuuauaauaL96 |
| AD-273625.1 | C5 | 953 | A-529248.14 | asasgcaagadTadTuuuuauaauaL96 |
| AD-273626.1 | C5 | 955 | A-529248.15 | asasgcaagadTadTuuuuauaauaL96 |
| AD-273627.1 | C5 | 957 | A-529248.16 | asasgcaagadTadTuuuuauaauaL96 |
| AD-273628.1 | C5 | 959 | A-529248.17 | asasgcaagadTadTuuuuauaauaL96 |
| AD-273629.1 | C5 | 961 | A-529248.18 | asasgcaagadTadTuuuuauaauaL96 |
| AD-273630.1 | C5 | 963 | A-529248.19 | asasgcaagadTadTuuuuauaauaL96 |

| Duplex Number | SEQ ID NO: | asOligoName | asOligoSeq |
|---|---|---|---|
| AD-157529.3 | 8 | A-311777.2 | usdGsuacdTcucaudTgdTggaugacsgsa |
| AD-191860.3 | 10 | A-379557.3 | usdGsuadCucucaudTgdTggaugacsgsa |
| AD-192113.1 | 12 | A-379557.4 | usdGsuadCucucaudTgdTggaugacsgsa |
| AD-192114.1 | 14 | A-380002.1 | usdGsdTadCucucaudTgdTggaugacsgsa |
| AD-192115.1 | 16 | A-380003.1 | usdGsudAdCucucaudTgdTggaugacsgsa |
| AD-192116.1 | 18 | A-380004.1 | usdGsuadCdTcucaudTgdTggaugacsgsa |
| AD-192117.1 | 20 | A-380005.1 | usdGsuadCudCucaudTgdTggaugacsgsa |
| AD-192118.1 | 22 | A-380006.1 | usdGsuadCucdTcaudTgdTggaugacsgsa |
| AD-192119.1 | 24 | A-379557.5 | usdGsuadCucucaudTgdTggaugacsgsa |
| AD-192120.1 | 26 | A-379557.6 | usdGsuadCucucaudTgdTggaugacsgsa |
| AD-157541.2 | 28 | A-145692.4 | asdTsuadGaagaaadAgdGugggagascsu |
| AD-192121.1 | 30 | A-145692.5 | asdTsuadGaagaaadAgdGugggagascsu |
| AD-192122.1 | 32 | A-380010.1 | asdTsdTadGaagaaadAgdGugggagascsu |
| AD-192123.1 | 34 | A-380011.1 | asdTsudAdGaagaaadAgdGugggagascsu |
| AD-192124.1 | 36 | A-380012.1 | asdTsuadGdAagaaadAgdGugggagascsu |

TABLE 1-continued

| Exemplary dsRNA agents | | | |
|---|---|---|---|
| AD-192125.1 | 38 | A-380013.1 | asdTsuadGadAgaaadAgdGugggagascsu |
| AD-192126.1 | 40 | A-380014.1 | asdTsuadGaadGaaadAgdGugggagascsu |
| AD-192127.1 | 42 | A-145692.6 | asdTsuadGaagaaadAgdGugggagascsu |
| AD-192128.1 | 44 | A-145692.7 | asdTsuadGaagaaadAgdGugggagascsu |
| AD-157552.3 | 46 | A-311793.2 | usdTscacadGguacdTcdTcauugugsgsa |
| AD-192129.1 | 48 | A-380017.1 | usdTscadCagguacdTcdTcauugugsgsa |
| AD-192130.1 | 50 | A-380017.2 | usdTscadCagguacdTcdTcauugugsgsa |
| AD-192131.1 | 52 | A-380019.1 | usdTsdCadCagguacdTcdTcauugugsgsa |
| AD-192132.1 | 54 | A-380020.1 | usdTscdAdCagguacdTcdTcauugugsgsa |
| AD-192133.1 | 56 | A-380021.1 | usdTscadCdAgguacdTcdTcauugugsgsa |
| AD-192134.1 | 58 | A-380022.1 | usdTscadCadGguacdTcdTcauugugsgsa |
| AD-192135.1 | 60 | A-380023.1 | usdTscadCagdGuacdTcdTcauugugsgsa |
| AD-192136.1 | 62 | A-380017.3 | usdTscadCagguacdTcdTcauugugsgsa |
| AD-192137.1 | 64 | A-380017.4 | usdTscadCagguacdTcdTcauugugsgsa |
| AD-157563.2 | 66 | A-311802.2 | asdGsuuucdTucaudCcdAguugaggsgsa |
| AD-192138.1 | 68 | A-380026.1 | asdGsuudTcuucaudCcdAguugaggsgsa |
| AD-192139.1 | 70 | A-380026.2 | asdGsuudTcuucaudCcdAguugaggsgsa |
| AD-192140.1 | 72 | A-380028.1 | asdGsdTudTcuucaudCcdAguugaggsgsa |
| AD-192141.1 | 74 | A-380029.1 | asdGsudTdTcuucaudCcdAguugaggsgsa |
| AD-192142.1 | 76 | A-380030.1 | asdGsuudTdCuucaudCcdAguugaggsgsa |
| AD-192143.1 | 78 | A-380031.1 | asdGsuudTcdTucaudCcdAguugaggsgsa |
| AD-192144.1 | 80 | A-380032.1 | asdGsuudTcudTcaudCcdAguugaggsgsa |
| AD-192145.1 | 82 | A-380026.3 | asdGsuudTcuucaudCcdAguugaggsgsa |
| AD-192146.1 | 84 | A-380026.4 | asdGsuudTcuucaudCcdAguugaggsgsa |
| AD-157574.2 | 86 | A-311810.2 | usdAsaccdTgucaadTcdTucucagcsasg |
| AD-192147.1 | 88 | A-380035.1 | usdAsacdCugucaadTcdTucucagcsasg |
| AD-192148.1 | 90 | A-380035.2 | usdAsacdCugucaadTcdTucucagcsasg |
| AD-192149.1 | 92 | A-380037.1 | usdAsdAcdCugucaadTcdTucucagcsasg |
| AD-192150.1 | 94 | A-380038.1 | usdAsadCdCugucaadTcdTucucagcsasg |
| AD-192151.1 | 96 | A-380039.1 | usdAsacdCdTgucaadTcdTucucagcsasg |
| AD-192152.1 | 98 | A-380040.1 | usdAsacdCudGucaadTcdTucucagcsasg |
| AD-192153.1 | 100 | A-380041.1 | usdAsacdCugdTcaadTcdTucucagcsasg |
| AD-192154.1 | 102 | A-380035.3 | usdAsacdCugucaadTcdTucucagcsasg |
| AD-192155.1 | 104 | A-380035.4 | usdAsacdCugucaadTcdTucucagcsasg |
| AD-157584.2 | 106 | A-311817.2 | usdAsguudTugcugdGadAagugagascsc |
| AD-192156.1 | 108 | A-380044.1 | usdAsgudTuugcugdGadAagugagascsc |
| AD-192157.1 | 110 | A-380044.2 | usdAsgudTuugcugdGadAagugagascsc |
| AD-192158.1 | 112 | A-380046.1 | usdAsdGudTuugcugdGadAagugagascsc |
| AD-192159.1 | 114 | A-380047.1 | usdAsgdTdTuugcugdGadAagugagascsc |

TABLE 1-continued

| Exemplary dsRNA agents | | | |
|---|---|---|---|
| AD-192160.1 | 116 | A-380048.1 | usdAsgudTdTugcugdGadAagugagascsc |
| AD-192161.1 | 118 | A-380049.1 | usdAsgudTudTgcugdGadAagugagascsc |
| AD-192162.1 | 120 | A-380050.1 | usdAsgudTuudGcugdGadAagugagascsc |
| AD-192163.1 | 122 | A-380044.3 | usdAsgudTuugcugdGadAagugagascsc |
| AD-192164.1 | 124 | A-380044.4 | usdAsgudTuugcugdGadAagugagascsc |
| AD-264555.1 | 126 | A-511273.1 | usdTsucdAadAgcacdTudTauugagususc |
| AD-264556.1 | 128 | A-511274.1 | usdAsgadAgdCugagdGcdTcaaagcascsu |
| AD-264557.1 | 130 | A-511275.1 | usdTsggdTcdTuucadCudTucuugggscsu |
| AD-264558.1 | 132 | A-511276.1 | usdAsaadGcdAcuuudAudTgaguuccsusg |
| AD-264559.1 | 134 | A-511277.1 | usdGsgudCudTucacdTudTcuugggcsusc |
| AD-264560.1 | 136 | A-511278.1 | usdAsagdCudGaggcdTcdAaagcacususc |
| AD-264561.1 | 138 | A-511279.1 | asdTsuudTcdAaagcdAcdTuuauugasgsu |
| AD-264562.1 | 140 | A-511280.1 | usdTscudTudCacuudTcdTugggcucscsa |
| AD-264563.1 | 142 | A-511281.1 | usdTsuudCadCuuucdTudGggcuccascsa |
| AD-264564.1 | 144 | A-511282.1 | usdTscadAadGcacudTudAuugaguuscsc |
| AD-264565.1 | 146 | A-511283.1 | asdGsaadGcdTgaggdCudCaaagcacsusu |
| AD-264566.1 | 148 | A-511284.1 | usdTscadCudTucuudGgdGcuccacascsa |
| AD-264567.1 | 150 | A-511285.1 | usdTsuudCadAagcadCudTuauugagsusu |
| AD-264568.1 | 152 | A-511286.1 | usdGsagdAadGcugadGgdCucaaagcsasc |
| AD-264569.1 | 154 | A-511287.1 | usdTsucdAcdTuucudTgdGgcuccacsasc |
| AD-264570.1 | 156 | A-511288.1 | usdCsuudTcdAcuuudCudTgggcuccsasc |
| AD-264571.1 | 158 | A-511289.1 | usdCsaadAgdCacuudTadTugaguucscsu |
| AD-264572.1 | 160 | A-511290.1 | usdTsugdTudGcggudCadCcacagccscsg |
| AD-264573.1 | 162 | A-511291.1 | usdGsucdTudTcacudTudCuugggcuscsc |
| AD-264574.1 | 164 | A-511292.1 | usdTsugdGadCagagdAadGucugaugsasu |
| AD-264575.1 | 166 | A-511293.1 | usdTsugdCudGcaaudGgdTcuuucacsusu |
| AD-264576.1 | 168 | A-511294.1 | usdAsaadTudTcuugdGadGucuuuccsasu |
| AD-264577.1 | 170 | A-511295.1 | usdAsugdAadGcaaudAudGcuucuggsasu |
| AD-264578.1 | 172 | A-511296.1 | usdAsuadAadGccugdGudTaguuaugsasa |
| AD-264579.1 | 174 | A-511297.1 | usdAsuudTcdTcuuudCudGgcaaugususu |
| AD-264580.1 | 176 | A-511298.1 | usdAsaadGcdAcuuudAudTgaguuucsusg |
| AD-264581.1 | 178 | A-511299.1 | asdAsgudCgdCaaaadAudAuccagugsusa |
| AD-264582.1 | 180 | A-511300.1 | usdAsagdTcdGcaaadAadTauccagusgsu |
| AD-264583.1 | 182 | A-511301.1 | usdAsagdGadTaaagdCcdTgguuagususa |
| AD-264584.1 | 184 | A-511302.1 | asdAsagdGudCcaagdTcdGcaaaaausasu |
| AD-264585.1 | 186 | A-511303.1 | usdTsaudGadAgcaadTadTgcuucugsgsa |
| AD-264586.1 | 188 | A-511304.1 | asdAsaudTudCuuggdAgdTcuuuccasusg |
| AD-264587.1 | 190 | A-511305.1 | usdTscgdCadAaaaudAudCcaguguasgsc |
| AD-264588.1 | 192 | A-511306.1 | usdTsaadAudTucuudGgdAgucuuucscsa |

TABLE 1-continued

| Exemplary dsRNA agents | | | |
|---|---|---|---|
| AD-264589.1 | 194 | A-511307.1 | usdAsaadGgdTccaadGudCgcaaaaasusa |
| AD-264590.1 | 196 | A-511308.1 | gsdTsuudTcdAaagcdAcdTuuauugasgsu |
| AD-264591.1 | 198 | A-511309.1 | asdAsaadAudAuccadGudGuagccugsusa |
| AD-264592.1 | 200 | A-511310.1 | asdTsuudCudTggagdTcdTuuccaugsgsu |
| AD-264593.1 | 202 | A-511311.1 | usdTsuadGcdGcuugdCudTcucagucsasu |
| AD-264594.1 | 204 | A-511312.1 | usdTsccdTudAaauudTcdTuggagucsusu |
| AD-264595.1 | 206 | A-511313.1 | usdAsaudGgdTcuuudCadCuuucuugsgsg |
| AD-264596.1 | 208 | A-511314.1 | usdTsucdAadAgcacdTudTauugagusuau |
| AD-264597.1 | 210 | A-511315.1 | usdAsuadGcdTcauudCudCguggaagsasa |
| AD-264598.1 | 212 | A-511316.1 | asdAsggdAudAaagcdCudGguuaguusasu |
| AD-264599.1 | 214 | A-511317.1 | usdAsaadGudGucagdAudCcagacucsasu |
| AD-264600.1 | 216 | A-511318.1 | usdAsaadGcdAuuucdTcdTuucuggcsasa |
| AD-264601.1 | 218 | A-511319.1 | usdAsgadAgdCugagdGcdTcaaagcasusu |
| AD-237788.1 | 220 | A-461233.1 | usdAsacdAcdGguuudAudAgagcaagsasa |
| AD-237789.1 | 222 | A-461234.1 | usdTsuudAudAgagcdAadGaacacugsusu |
| AD-237790.1 | 224 | A-461235.1 | asdAscadCgdGuuuadTadGagcaagasasc |
| AD-237791.1 | 226 | A-461236.1 | usdAscgdGudTuauadGadGcaagaacsasc |
| AD-237792.1 | 228 | A-461237.1 | usdTsaadCadCgguudTadTagagcaasgsa |
| AD-237793.1 | 230 | A-461238.1 | usdGsuudTadTagagdCadAgaacacusgsu |
| AD-237794.1 | 232 | A-461239.1 | usdAsggdAcdTuugadCcdAucagaggsasc |
| AD-237795.1 | 234 | A-461240.1 | usdAscgdAudTuggudGudCcaguucusasc |
| AD-237796.1 | 236 | A-461241.1 | usdTsuadTadGagcadAgdAacacugusuu |
| AD-237797.1 | 238 | A-461242.1 | usdTsacdGadTuuggdTgdTccaguucsusa |
| AD-237798.1 | 240 | A-461243.1 | usdTsgcdTadAcacgdGudTuauagagscsa |
| AD-237799.1 | 242 | A-461244.1 | usdAsgudAcdGauuudGgdTguccagusuc |
| AD-237800.1 | 244 | A-461245.1 | usdAscudGcdTuuggdCadAgauccugsgsu |
| AD-237801.1 | 246 | A-461246.1 | asdCsggdTudTauagdAgdCaagaacascsu |
| AD-237802.1 | 248 | A-461247.1 | asdAsacdTudCucaudCudGuggugagscsc |
| AD-237803.1 | 250 | A-461248.1 | asdGsgadCudTugacdCadTcagaggascsa |
| AD-237804.1 | 252 | A-461249.1 | asdCsacdGgdTuuaudAgdAgcaagaascsa |
| AD-237805.1 | 254 | A-461250.1 | usdTsacdTgdCuuugdGcdAagauccusgsg |
| AD-237806.1 | 256 | A-461251.1 | usdGscudAadCacggdTudTauagagcsasa |
| AD-237807.1 | 258 | A-461252.1 | usdAsggdGcdTgcgadTgdGuguagugsgsc |
| AD-237808.1 | 260 | A-461253.1 | usdCsuadAcdAcggudTudAuagagcasasg |
| AD-237809.1 | 262 | A-461254.1 | usdTsccdAgdTacgadTudTgguguccsasg |
| AD-237810.1 | 264 | A-461255.1 | asdCsugdCudTuggcdAadGauccuggsusc |
| AD-237811.1 | 266 | A-461256.1 | usdCsugdCgdAuggudGudAguggcgasusg |
| AD-237812.1 | 268 | A-461257.1 | usdAsagdAudCcuggdTcdCuccugggscsu |
| AD-237813.1 | 270 | A-461258.1 | usdAscadGcdAuccadGgdAcuuugacscsa |

TABLE 1-continued

| Exemplary dsRNA agents | | | |
|---|---|---|---|
| AD-237814.1 | 272 | A-461259.1 | usdAsgcdAgdGgcugdCgdAugguguasgsu |
| AD-237815.1 | 274 | A-461260.1 | usdAsgcdAudCcaggdAcdTuugaccasusc |
| AD-237816.1 | 276 | A-461261.1 | usdCsggdAcdAgcaudCcdAggacuuusgsa |
| AD-237817.1 | 278 | A-461262.1 | usdAsgcdAgdGgcugdCcdTcggacagscsa |
| AD-237818.1 | 280 | A-461263.1 | usdGsgudTudAuagadGcdAagaacacsusg |
| AD-237819.1 | 282 | A-461264.1 | usdAsucdCadGgacudTudGaccaucasgsa |
| AD-237820.1 | 284 | A-461265.1 | asdGsggdCudGcgaudGgdTguaguggscsg |
| AD-237821.1 | 286 | A-461266.1 | usdTsucdTcdAucugdTgdGugagcccsgsu |
| AD-237822.1 | 288 | A-461267.1 | usdTsgcdTudTggcadAgdAuccuggusCsc |
| AD-237823.1 | 290 | A-461268.1 | usdTsgcdCudCggacdAgdCauccaggsasc |
| AD-237824.1 | 292 | A-461269.1 | asdCsagdCadTccagdGadCuuugaccsasu |
| AD-237825.1 | 294 | A-461270.1 | usdTscadTcdTguggdTgdAgcccgugscsa |
| AD-237826.1 | 296 | A-461271.1 | usdCsuadCudGcuuudGgdCaagauccsusg |
| AD-237827.1 | 298 | A-461272.1 | asdAscudTcdTcaucdTgdTggugagcscsc |
| AD-237828.1 | 300 | A-461273.1 | usdCsagdGadCuuugdAcdCaucagagsgsa |
| AD-237829.1 | 302 | A-461274.1 | usdCsagdTadCgauudTgdGuguccagsusu |
| AD-237830.1 | 304 | A-461275.1 | usdTscudCadTcugudGgdTgagcccgsusg |
| AD-237831.1 | 306 | A-461276.1 | usdCscadGudAcgaudTudGguguccasgsu |
| AD-237832.1 | 308 | A-461277.1 | usdTsgadGcdCcgugdCadGcucuccasgsa |
| AD-237833.1 | 310 | A-461278.1 | asdAsgadTcdCuggudCcdTccugggcsusg |
| AD-237834.1 | 312 | A-461279.1 | usdCsuudTgdGcaagdAudCcugguccsusc |
| AD-237835.1 | 314 | A-461280.1 | usdAsucdTgdTggugdAgdCccgugcasgsc |
| AD-237836.1 | 316 | A-461281.1 | usdCsgadAgdGgaagdCcdAuccugucsasg |
| AD-237837.1 | 318 | A-461282.1 | usdGscudGcdGauggdTgdTaguggcgsasu |
| AD-237838.1 | 320 | A-461283.1 | usdTscgdGadCagcadTcdCaggacuusug |
| AD-237839.1 | 322 | A-461284.1 | usdCsucdGgdAcagcdAudCcaggacususu |
| AD-237840.1 | 324 | A-461285.1 | asdTscudGudGgugadGcdCcgugcagscsu |
| AD-237841.1 | 326 | A-461286.1 | usdGscudTudGgcaadGadTccuggucscsu |
| AD-237842.1 | 328 | A-461287.1 | asdGsuadCgdAuuugdGudGuccaguuscsu |
| AD-237843.1 | 330 | A-461288.1 | usdCsaudCcdAggacdTudTgaccaucsasg |
| AD-237844.1 | 332 | A-461289.1 | asdGscadTcdCaggadCudTugaccauscsa |
| AD-237845.1 | 334 | A-461290.1 | usdGsgcdTgdCgaugdGudGuaguggcsgsa |
| AD-237846.1 | 336 | A-461291.1 | usdGsaadGgdGaagcdCadTccugucasgsg |
| AD-237847.1 | 338 | A-461292.1 | usdTsggdTgdAgcccdGudGcagcucuscsc |
| AD-237848.1 | 340 | A-461293.1 | usdCscudCgdGacagdCadTccaggacsusu |
| AD-237849.1 | 342 | A-461294.1 | usdAsggdGcdTgccudCgdGacagcauscsc |
| AD-237850.1 | 344 | A-461295.1 | usdGsugdAgdCccgudGcdAgcucuccsasg |
| AD-237851.1 | 346 | A-461296.1 | usdCsugdCcdTcggadCadGcauccagsgsa |
| AD-237852.1 | 348 | A-461297.1 | usdGsagdCadGggcudGcdGauggugusasg |

TABLE 1-continued

| Exemplary dsRNA agents | | | |
|---|---|---|---|
| AD-237853.1 | 350 | A-461298.1 | usdCsaadGadTccugdGudCcuccuggsgsc |
| AD-237854.1 | 352 | A-461299.1 | usdCsucdAudCugugdGudGagcccgusgsc |
| AD-237855.1 | 354 | A-461300.1 | usdGscudAcdTgcuudTgdGcaagaucscsu |
| AD-237856.1 | 356 | A-461301.1 | usdAsgcdCcdGugcadGcdTcuccagascsu |
| AD-237857.1 | 358 | A-461302.1 | usdCsaudCudGuggudGadGcccgugcsasg |
| AD-237858.1 | 360 | A-461303.1 | usdGscudGcdCucggdAcdAgcauccasgsg |
| AD-237859.1 | 362 | A-461304.1 | asdGsggdCudGccucdGgdAcagcaucscsa |
| AD-237860.1 | 364 | A-461305.1 | asdGsccdCgdTgcagdCudCuccagacsusc |
| AD-237861.1 | 366 | A-461306.1 | usdGsagdCcdCgugcdAgdCucuccagsasc |
| AD-237862.1 | 368 | A-461307.1 | asdCsuudCudCaucudGudGgugagccscsg |
| AD-237863.1 | 370 | A-461308.1 | usdGsccdTcdGgacadGcdAuccaggascsu |
| AD-237864.1 | 372 | A-461309.1 | usdGsgcdTgdCcucgdGadCagcauccsasg |
| AD-237865.1 | 374 | A-461310.1 | usdGscadAgdAuccudGgdTccuccugsgsg |
| AD-237866.1 | 376 | A-461311.1 | usdGsgudGadGcccgdTgdCagcucucscsa |
| AD-218795.6 | 378 | A-432271.4 | usdTsaudAgadGcaadGadAcacuguususu |
| AD-238829.1 | 380 | A-129907.9 | usdTsauagagcaadGadAcacuguususu |
| AD-238830.1 | 382 | A-463179.1 | usdTsadTagagcaadGadAcacuguususu |
| AD-238831.1 | 384 | A-463180.1 | usdTsadTadGagcaadGadAcacuguususu |
| AD-238832.1 | 386 | A-463181.1 | usdTsadTadGadGcaadGadAcacuguususu |
| AD-238833.1 | 388 | A-463182.1 | usdTsadTadGadGcdAadGadAcacuguususu |
| AD-238834.1 | 390 | A-463183.1 | usdTsaudAgdAgdCaadGadAcacuguususu |
| AD-238835.1 | 392 | A-463184.1 | usdTsaudAgagcaadGadAcacuguususu |
| AD-238836.1 | 394 | A-463185.1 | usdTsauadGagcaadGadAcacuguususu |
| AD-238837.1 | 396 | A-463186.1 | usdTsauagdAgcaadGadAcacuguususu |
| AD-238838.1 | 398 | A-463187.1 | usdTsauagadGcaadGadAcacuguususu |
| AD-238839.1 | 400 | A-463188.1 | usdTsauadGadGcaadGadAcacuguususu |
| AD-238840.1 | 402 | A-463189.1 | usdTsadTagdAgcaadGadAcacuguususu |
| AD-238841.1 | 404 | A-463190.1 | usdTsaudAgdAgcaadGadAcacuguususu |
| AD-238842.1 | 406 | A-463191.1 | usdTsauagagcaadGadAcdAcuguususu |
| AD-238843.1 | 408 | A-463192.1 | usdTsadTagagcaadGadAcdAcuguususu |
| AD-238844.1 | 410 | A-463193.1 | usdTsadTadGagcaadGadAcdAcuguususu |
| AD-238845.1 | 412 | A-463194.1 | usdTsadTadGadGcaadGadAcdAcuguususu |
| AD-238846.1 | 414 | A-463195.1 | usdTsadTadGadGcdAadGadAcdAcuguususu |
| AD-238847.1 | 416 | A-463196.1 | usdTsaudAgdAgdCaadGadAcdAcuguususu |
| AD-238848.1 | 418 | A-463197.1 | usdTsaudAgagcaadGadAcdAcuguususu |
| AD-238849.1 | 420 | A-463198.1 | usdTsauadGagcaadGadAcdAcuguususu |
| AD-238850.1 | 422 | A-463199.1 | usdTsauagdAgcaadGadAcdAcuguususu |
| AD-238851.1 | 424 | A-463200.1 | usdTsauagadGcaadGadAcdAcuguususu |
| AD-238852.1 | 426 | A-463201.1 | usdTsauadGadGcaadGadAcdAcuguususu |

TABLE 1-continued

| Exemplary dsRNA agents | | | |
|---|---|---|---|
| AD-238853.1 | 428 | A-463202.1 | usdTsadTagdAgcaadGadAcdAcuguususu |
| AD-238854.1 | 430 | A-463203.1 | usdTsaudAgdAgcaadGadAcdAcuguususu |
| AD-238855.1 | 432 | A-463204.1 | usdTsdAdTdAdGdAdGcaadGadAcacuguususu |
| AD-238856.1 | 434 | A-463205.1 | usdTsdAdTdAdGdAdGcaadGadAcdAcuguususu |
| AD-238857.1 | 436 | A-463206.1 | usdTsdAudAgdAgcaadGadAcacuguususu |
| AD-238858.1 | 438 | A-463207.1 | usdTsadTdAgdAgcaadGadAcacuguususu |
| AD-238859.1 | 440 | A-463208.1 | usdTsaudAdGdAgcaadGadAcacuguususu |
| AD-238860.1 | 442 | A-463209.1 | usdTsaudAgdAdGcaadGadAcacuguususu |
| AD-238861.1 | 444 | A-463190.2 | usdTsaudAgdAgcaadGadAcacuguususu |
| AD-238862.1 | 446 | A-463190.3 | usdTsaudAgdAgcaadGadAcacuguususu |
| AD-238863.1 | 448 | A-463190.4 | usdTsaudAgdAgcaadGadAcacuguususu |
| AD-192134.4 | 450 | A-380022.5 | usdTscadCadGguacdTcdTcauugugsgsa |
| AD-157553.2 | 452 | A-250577.10 | usdTscacagguacdTcdTcauugugsgsa |
| AD-238872.1 | 454 | A-463221.1 | usdTscdAcagguacdTcdTcauugugsgsa |
| AD-238873.1 | 456 | A-463222.1 | usdTscdAcdAgguacdTcdTcauugugsgsa |
| AD-238874.1 | 458 | A-463223.1 | usdTscdAcdAgdGuacdTcdTcauugugsgsa |
| AD-238875.1 | 460 | A-463224.1 | usdTscdAcdAgdGudAcdTcdTcauugugsgsa |
| AD-238876.1 | 462 | A-463225.1 | usdTscadCadGgdTacdTcdTcauugugsgsa |
| AD-192129.4 | 464 | A-380017.6 | usdTscadCagguacdTcdTcauugugsgsa |
| AD-238877.1 | 466 | A-463226.1 | usdTscacdAgguacdTcdTcauugugsgsa |
| AD-157552.4 | 468 | A-311793.3 | usdTscacadGguacdTcdTcauugugsgsa |
| AD-238878.1 | 470 | A-463227.1 | usdTscacagdGuacdTcdTcauugugsgsa |
| AD-238879.1 | 472 | A-463228.1 | usdTscacdAgdGuacdTcdTcauugugsgsa |
| AD-238880.1 | 474 | A-463229.1 | usdTscdAcadGguacdTcdTcauugugsgsa |
| AD-192135.2 | 476 | A-380023.2 | usdTscadCagdGuacdTcdTcauugugsgsa |
| AD-238881.1 | 478 | A-463230.1 | usdTscacagguacdTcdTcdAuugugsgsa |
| AD-238882.1 | 480 | A-463231.1 | usdTscdAcagguacdTcdTcdAuugugsgsa |
| AD-238883.1 | 482 | A-463232.1 | usdTscdAcdAgguacdTcdTcdAuugugsgsa |
| AD-238884.1 | 484 | A-463233.1 | usdTscdAcdAgdGuacdTcdTcdAuugugsgsa |
| AD-238885.1 | 486 | A-463234.1 | usdTscdAcdAgdGudAcdTcdTcdAuugugsgsa |
| AD-238886.1 | 488 | A-463235.1 | usdTscadCadGgdTacdTcdTcdAuugugsgsa |
| AD-238887.1 | 490 | A-463236.1 | usdTscadCagguacdTcdTcdAuugugsgsa |
| AD-238888.1 | 492 | A-463237.1 | usdTscacdAgguacdTcdTcdAuugugsgsa |
| AD-238889.1 | 494 | A-463238.1 | usdTscacadGguacdTcdTcdAuugugsgsa |
| AD-238890.1 | 496 | A-463239.1 | usdTscacagdGuacdTcdTcdAuugugsgsa |
| AD-238891.1 | 498 | A-463240.1 | usdTscacdAgdGuacdTcdTcdAuugugsgsa |
| AD-238892.1 | 500 | A-463241.1 | usdTscdAcadGguacdTcdTcdAuugugsgsa |
| AD-238893.1 | 502 | A-463242.1 | usdTscadCadGguacdTcdTcdAuugugsgsa |
| AD-238894.1 | 504 | A-463243.1 | usdTsdCdAdCdAdGdGuacdTcdTcauugugsgsa |

TABLE 1-continued

| Exemplary dsRNA agents | | | |
|---|---|---|---|
| AD-238895.1 | 506 | A-463244.1 | usdTsdCdAdCdAdGdGuacdTcdTcdAuugugsgsa |
| AD-238896.1 | 508 | A-463245.1 | usdTsdCadCadGguacdTcdTcauugugsgsa |
| AD-238897.1 | 510 | A-463246.1 | usdTscdAdCadGguacdTcdTcauugugsgsa |
| AD-238898.1 | 512 | A-463247.1 | usdTscadCdAdGguacdTcdTcauugugsgsa |
| AD-238899.1 | 514 | A-463248.1 | usdTscadCadGdGuacdTcdTcauugugsgsa |
| AD-238900.1 | 516 | A-380022.6 | usdTscadCadGguacdTcdTcauugugsgsa |
| AD-238901.1 | 518 | A-380022.7 | usdTscadCadGguacdTcdTcauugugsgsa |
| AD-238902.1 | 520 | A-380022.8 | usdTscadCadGguacdTcdTcauugugsgsa |
| AD-264561.2 | 522 | A-511279.2 | asdTsuudTcdAaagcdAcdTuuauugasgsu |
| AD-273421.1 | 524 | A-511279.3 | asdTsuudTcdAaagcdAcdTuuauugasgsu |
| AD-273422.1 | 526 | A-511279.4 | asdTsuudTcdAaagcdAcdTuuauugasgsu |
| AD-273423.1 | 528 | A-511279.5 | asdTsuudTcdAaagcdAcdTuuauugasgsu |
| AD-273424.1 | 530 | A-511279.6 | asdTsuudTcdAaagcdAcdTuuauugasgsu |
| AD-273425.1 | 532 | A-511279.7 | asdTsuudTcdAaagcdAcdTuuauugasgsu |
| AD-273426.1 | 534 | A-511279.8 | asdTsuudTcdAaagcdAcdTuuauugasgsu |
| AD-273427.1 | 536 | A-511279.9 | asdTsuudTcdAaagcdAcdTuuauugasgsu |
| AD-273428.1 | 538 | A-511279.10 | asdTsuudTcdAaagcdAcdTuuauugasgsu |
| AD-273429.1 | 540 | A-511279.11 | asdTsuudTcdAaagcdAcdTuuauugasgsu |
| AD-273430.1 | 542 | A-511279.12 | asdTsuudTcdAaagcdAcdTuuauugasgsu |
| AD-273431.1 | 544 | A-511279.13 | asdTsuudTcdAaagcdAcdTuuauugasgsu |
| AD-273432.1 | 546 | A-511279.14 | asdTsuudTcdAaagcdAcdTuuauugasgsu |
| AD-273433.1 | 548 | A-511279.15 | asdTsuudTcdAaagcdAcdTuuauugasgsu |
| AD-273434.1 | 550 | A-511279.16 | asdTsuudTcdAaagcdAcdTuuauugasgsu |
| AD-273435.1 | 552 | A-511279.17 | asdTsuudTcdAaagcdAcdTuuauugasgsu |
| AD-273436.1 | 554 | A-511279.18 | asdTsuudTcdAaagcdAcdTuuauugasgsu |
| AD-273437.1 | 556 | A-511279.19 | asdTsuudTcdAaagcdAcdTuuauugasgsu |
| AD-273438.1 | 558 | A-511279.20 | asdTsuudTcdAaagcdAcdTuuauugasgsu |
| AD-273439.1 | 560 | A-529094.1 | asdTsdTudTcdAaagcdAcdTuuauugasgsu |
| AD-273440.1 | 562 | A-529095.1 | asdTsudTdTcdAaagcdAcdTuuauugasgsu |
| AD-273441.1 | 564 | A-529096.1 | asdTsuuucdAaagcdAcdTuuauugasgsu |
| AD-273442.1 | 566 | A-529097.1 | asdTsuudTdCdAaagcdAcdTuuauugasgsu |
| AD-273443.1 | 568 | A-529098.1 | asdTsuudTcaaagcdAcdTuuauugasgsu |
| AD-273444.1 | 570 | A-529099.1 | asdTsuudTcdAdAagcdAcdTuuauugasgsu |
| AD-273445.1 | 572 | A-529100.1 | asdTsuudTcdAadAgcdAcdTuuauugasgsu |
| AD-273446.1 | 574 | A-529101.1 | asdTsuudTcdAaadGcdAcdTuuauugasgsu |
| AD-273447.1 | 576 | A-529102.1 | asdTsuudTcdAaagdCdAcdTuuauugasgsu |
| AD-273448.1 | 578 | A-529103.1 | asdTsuudTcdAaagcacdTuuauugasgsu |
| AD-273449.1 | 580 | A-529104.1 | asdTsuudTcdAaagcdAdCdTuuauugasgsu |
| AD-273450.1 | 582 | A-529105.1 | asdTsuudTcdAaagcdAcuuuauugasgsu |

TABLE 1-continued

| Exemplary dsRNA agents | | | |
|---|---|---|---|
| AD-273451.1 | 584 | A-529106.1 | asdTsuudTcdAaagcdAcdTdTuauugasgsu |
| AD-273452.1 | 586 | A-529107.1 | asdTsuudTcdAaagcdAcdTudTauugasgsu |
| AD-273453.1 | 588 | A-529108.1 | asdTsuudTcdAaagcdAcdTuudAuugasgsu |
| AD-273454.1 | 590 | A-529109.1 | asdTsuudTcdAaagcdAcdTuuadTugasgsu |
| AD-273455.1 | 592 | A-529110.1 | asdTsuudTcdAaagcdAcdTuuaudTgasgsu |
| AD-273456.1 | 594 | A-529111.1 | asdTsuudTcdAaagcdAcdTuuauudGasgsu |
| AD-264567.2 | 596 | A-511285.2 | usdTsuudCadAagcadCudTuauugagsusu |
| AD-273457.1 | 598 | A-511285.3 | usdTsuudCadAagcadCudTuauugagsusu |
| AD-273458.1 | 600 | A-511285.4 | usdTsuudCadAagcadCudTuauugagsusu |
| AD-273459.1 | 602 | A-511285.5 | usdTsuudCadAagcadCudTuauugagsusu |
| AD-273460.1 | 604 | A-511285.6 | usdTsuudCadAagcadCudTuauugagsusu |
| AD-273461.1 | 606 | A-511285.7 | usdTsuudCadAagcadCudTuauugagsusu |
| AD-273462.1 | 608 | A-511285.8 | usdTsuudCadAagcadCudTuauugagsusu |
| AD-273463.1 | 610 | A-511285.9 | usdTsuudCadAagcadCudTuauugagsusu |
| AD-273464.1 | 612 | A-511285.10 | usdTsuudCadAagcadCudTuauugagsusu |
| AD-273465.1 | 614 | A-511285.11 | usdTsuudCadAagcadCudTuauugagsusu |
| AD-273466.1 | 616 | A-511285.12 | usdTsuudCadAagcadCudTuauugagsusu |
| AD-273467.1 | 618 | A-511285.13 | usdTsuudCadAagcadCudTuauugagsusu |
| AD-273468.1 | 620 | A-511285.14 | usdTsuudCadAagcadCudTuauugagsusu |
| AD-273469.1 | 622 | A-511285.15 | usdTsuudCadAagcadCudTuauugagsusu |
| AD-273470.1 | 624 | A-511285.16 | usdTsuudCadAagcadCudTuauugagsusu |
| AD-273471.1 | 626 | A-511285.17 | usdTsuudCadAagcadCudTuauugagsusu |
| AD-273472.1 | 628 | A-511285.18 | usdTsuudCadAagcadCudTuauugagsusu |
| AD-273473.1 | 630 | A-511285.19 | usdTsuudCadAagcadCudTuauugagsusu |
| AD-273474.1 | 632 | A-511285.20 | usdTsuudCadAagcadCudTuauugagsusu |
| AD-273475.1 | 634 | A-529129.1 | usdTsdTudCadAagcadCudTuauugagsusu |
| AD-273476.1 | 636 | A-529130.1 | usdTsudTdCadAagcadCudTuauugagsusu |
| AD-273477.1 | 638 | A-529131.1 | usdTsuucadAagcadCudTuauugagsusu |
| AD-273478.1 | 640 | A-529132.1 | usdTsuudCdAdAagcadCudTuauugagsusu |
| AD-273479.1 | 642 | A-529133.1 | usdTsuudCaaagcadCudTuauugagsusu |
| AD-273480.1 | 644 | A-529134.1 | usdTsuudCadAdAgcadCudTuauugagsusu |
| AD-273481.1 | 646 | A-529135.1 | usdTsuudCadAadGcadCudTuauugagsusu |
| AD-273482.1 | 648 | A-529136.1 | usdTsuudCadAagdCadCudTuauugagsusu |
| AD-273483.1 | 650 | A-529137.1 | usdTsuudCadAagcdAdCudTuauugagsusu |
| AD-273484.1 | 652 | A-529138.1 | usdTsuudCadAagcacudTuauugagsusu |
| AD-273485.1 | 654 | A-529139.1 | usdTsuudCadAagcadCdTdTuauugagsusu |
| AD-273486.1 | 656 | A-529140.1 | usdTsuudCadAagcadCuuuauugagsusu |
| AD-273487.1 | 658 | A-529141.1 | usdTsuudCadAagcadCudTdTauugagsusu |
| AD-273488.1 | 660 | A-529142.1 | usdTsuudCadAagcadCudTudAuugagsusu |

TABLE 1-continued

| Exemplary dsRNA agents | | | |
|---|---|---|---|
| AD-273489.1 | 662 | A-529143.1 | usdTsuudCadAagcadCudTuadTugagsusu |
| AD-273490.1 | 664 | A-529144.1 | usdTsuudCadAagcadCudTuaudTgagsusu |
| AD-273491.1 | 666 | A-529145.1 | usdTsuudCadAagcadCudTuauudGagsusu |
| AD-273492.1 | 668 | A-529146.1 | usdTsuudCadAagcadCudTuauugdAgsusu |
| AD-238841.2 | 670 | A-463190.5 | usdTsaudAgdAgcaadGadAcacuguususu |
| AD-273493.1 | 672 | A-463190.6 | usdTsaudAgdAgcaadGadAcacuguususu |
| AD-273494.1 | 674 | A-463190.7 | usdTsaudAgdAgcaadGadAcacuguususu |
| AD-273495.1 | 676 | A-463190.8 | usdTsaudAgdAgcaadGadAcacuguususu |
| AD-273496.1 | 678 | A-463190.9 | usdTsaudAgdAgcaadGadAcacuguususu |
| AD-273497.1 | 680 | A-463190.10 | usdTsaudAgdAgcaadGadAcacuguususu |
| AD-273498.1 | 682 | A-463190.11 | usdTsaudAgdAgcaadGadAcacuguususu |
| AD-273499.1 | 684 | A-463190.12 | usdTsaudAgdAgcaadGadAcacuguususu |
| AD-273500.1 | 686 | A-463190.13 | usdTsaudAgdAgcaadGadAcacuguususu |
| AD-273501.1 | 688 | A-463190.14 | usdTsaudAgdAgcaadGadAcacuguususu |
| AD-273502.1 | 690 | A-463190.15 | usdTsaudAgdAgcaadGadAcacuguususu |
| AD-273503.1 | 692 | A-463190.16 | usdTsaudAgdAgcaadGadAcacuguususu |
| AD-273504.1 | 694 | A-463190.17 | usdTsaudAgdAgcaadGadAcacuguususu |
| AD-273505.1 | 696 | A-463190.18 | usdTsaudAgdAgcaadGadAcacuguususu |
| AD-273506.1 | 698 | A-463190.19 | usdTsaudAgdAgcaadGadAcacuguususu |
| AD-273507.1 | 700 | A-463190.20 | usdTsaudAgdAgcaadGadAcacuguususu |
| AD-273508.1 | 702 | A-463190.21 | usdTsaudAgdAgcaadGadAcacuguususu |
| AD-273509.1 | 704 | A-463190.22 | usdTsaudAgdAgcaadGadAcacuguususu |
| AD-273510.1 | 706 | A-463190.23 | usdTsaudAgdAgcaadGadAcacuguususu |
| AD-238857.2 | 708 | A-463206.2 | usdTsdAudAgdAgcaadGadAcacuguususu |
| AD-238858.2 | 710 | A-463207.2 | usdTsadTdAgdAgcaadGadAcacuguususu |
| AD-238837.2 | 712 | A-463186.2 | usdTsauagdAgcaadGadAcacuguususu |
| AD-238859.2 | 714 | A-463208.2 | usdTsaudAdGdAgcaadGadAcacuguususu |
| AD-238835.2 | 716 | A-463184.2 | usdTsaudAgagcaadGadAcacuguususu |
| AD-238860.2 | 718 | A-463209.2 | usdTsaudAgdAdGcaadGadAcacuguususu |
| AD-238834.2 | 720 | A-463183.2 | usdTsaudAgdAgdCaadGadAcacuguususu |
| AD-273511.1 | 722 | A-529164.1 | usdTsaudAgdAgcdAadGadAcacuguususu |
| AD-273512.1 | 724 | A-529165.1 | usdTsaudAgdAgcadAdGadAcacuguususu |
| AD-273513.1 | 726 | A-529166.1 | usdTsaudAgdAgcaagadAcacuguususu |
| AD-273514.1 | 728 | A-529167.1 | usdTsaudAgdAgcaadGdAdAcacuguususu |
| AD-273515.1 | 730 | A-529168.1 | usdTsaudAgdAgcaadGaacacuguususu |
| AD-273516.1 | 732 | A-529169.1 | usdTsaudAgdAgcaadGadAdCacuguususu |
| AD-238854.2 | 734 | A-463203.2 | usdTsaudAgdAgcaadGadAcdAcuguususu |
| AD-273517.1 | 736 | A-529170.1 | usdTsaudAgdAgcaadGadAcadCuguususu |
| AD-273518.1 | 738 | A-529171.1 | usdTsaudAgdAgcaadGadAcacdTguususu |

TABLE 1-continued

| Exemplary dsRNA agents | | | |
|---|---|---|---|
| AD-273519.1 | 740 | A-529172.1 | usdTsaudAgdAgcaadGadAcacudGuususu |
| AD-273520.1 | 742 | A-529173.1 | usdTsaudAgdAgcaadGadAcacugdTususu |
| AD-237793.2 | 744 | A-461238.2 | usdGsuudTadTagagdCadAgaacacusgsu |
| AD-273521.1 | 746 | A-461238.3 | usdGsuudTadTagagdCadAgaacacusgsu |
| AD-273522.1 | 748 | A-461238.4 | usdGsuudTadTagagdCadAgaacacusgsu |
| AD-273523.1 | 750 | A-461238.5 | usdGsuudTadTagagdCadAgaacacusgsu |
| AD-273524.1 | 752 | A-461238.6 | usdGsuudTadTagagdCadAgaacacusgsu |
| AD-273525.1 | 754 | A-461238.7 | usdGsuudTadTagagdCadAgaacacusgsu |
| AD-273526.1 | 756 | A-461238.8 | usdGsuudTadTagagdCadAgaacacusgsu |
| AD-273527.1 | 758 | A-461238.9 | usdGsuudTadTagagdCadAgaacacusgsu |
| AD-273528.1 | 760 | A-461238.10 | usdGsuudTadTagagdCadAgaacacusgsu |
| AD-273529.1 | 762 | A-461238.11 | usdGsuudTadTagagdCadAgaacacusgsu |
| AD-273530.1 | 764 | A-461238.12 | usdGsuudTadTagagdCadAgaacacusgsu |
| AD-273531.1 | 766 | A-461238.13 | usdGsuudTadTagagdCadAgaacacusgsu |
| AD-273532.1 | 768 | A-461238.14 | usdGsuudTadTagagdCadAgaacacusgsu |
| AD-273533.1 | 770 | A-461238.15 | usdGsuudTadTagagdCadAgaacacusgsu |
| AD-273534.1 | 772 | A-461238.16 | usdGsuudTadTagagdCadAgaacacusgsu |
| AD-273535.1 | 774 | A-461238.17 | usdGsuudTadTagagdCadAgaacacusgsu |
| AD-273536.1 | 776 | A-461238.18 | usdGsuudTadTagagdCadAgaacacusgsu |
| AD-273537.1 | 778 | A-461238.19 | usdGsuudTadTagagdCadAgaacacusgsu |
| AD-273538.1 | 780 | A-461238.20 | usdGsuudTadTagagdCadAgaacacusgsu |
| AD-273539.1 | 782 | A-529192.1 | usdGsdTudTadTagagdCadAgaacacusgsu |
| AD-273540.1 | 784 | A-529193.1 | usdGsudTdTadTagagdCadAgaacacusgsu |
| AD-273541.1 | 786 | A-529194.1 | usdGsuuuadTagagdCadAgaacacusgsu |
| AD-273542.1 | 788 | A-529195.1 | usdGsuudTdAdTagagdCadAgaacacusgsu |
| AD-273543.1 | 790 | A-529196.1 | usdGsuudTauagagdCadAgaacacusgsu |
| AD-273544.1 | 792 | A-529197.1 | usdGsuudTadTdAgagdCadAgaacacusgsu |
| AD-273545.1 | 794 | A-529198.1 | usdGsuudTadTadGagdCadAgaacacusgsu |
| AD-273546.1 | 796 | A-529199.1 | usdGsuudTadTagdAgdCadAgaacacusgsu |
| AD-273547.1 | 798 | A-529200.1 | usdGsuudTadTagadGdCadAgaacacusgsu |
| AD-273548.1 | 800 | A-529201.1 | usdGsuudTadTagagcadAgaacacusgsu |
| AD-273549.1 | 802 | A-529202.1 | usdGsuudTadTagagdCdAdAgaacacusgsu |
| AD-273550.1 | 804 | A-529203.1 | usdGsuudTadTagagdCaagaacacusgsu |
| AD-273551.1 | 806 | A-529204.1 | usdGsuudTadTagagdCadAdGaacacusgsu |
| AD-273552.1 | 808 | A-529205.1 | usdGsuudTadTagagdCadAgdAacacusgsu |
| AD-273553.1 | 810 | A-529206.1 | usdGsuudTadTagagdCadAgadAcacusgsu |
| AD-273554.1 | 812 | A-529207.1 | usdGsuudTadTagagdCadAgaadCacusgsu |
| AD-273555.1 | 814 | A-529208.1 | usdGsuudTadTagagdCadAgaacdAcusgsu |
| AD-273556.1 | 816 | A-529209.1 | usdGsuudTadTagagdCadAgaacadCusgsu |

TABLE 1-continued

| Exemplary dsRNA agents | | | |
|---|---|---|---|
| AD-273557.1 | 818 | A-529211.1 | usdTsaudAgdTgagudTadTuuugucasasu |
| AD-273558.1 | 820 | A-529211.2 | usdTsaudAgdTgagudTadTuuugucasasu |
| AD-273559.1 | 822 | A-529211.3 | usdTsaudAgdTgagudTadTuuugucasasu |
| AD-273560.1 | 824 | A-529211.4 | usdTsaudAgdTgagudTadTuuugucasasu |
| AD-273561.1 | 826 | A-529211.5 | usdTsaudAgdTgagudTadTuuugucasasu |
| AD-273562.1 | 828 | A-529211.6 | usdTsaudAgdTgagudTadTuuugucasasu |
| AD-273563.1 | 830 | A-529211.7 | usdTsaudAgdTgagudTadTuuugucasasu |
| AD-273564.1 | 832 | A-529211.8 | usdTsaudAgdTgagudTadTuuugucasasu |
| AD-273565.1 | 834 | A-529211.9 | usdTsaudAgdTgagudTadTuuugucasasu |
| AD-273566.1 | 836 | A-529211.10 | usdTsaudAgdTgagudTadTuuugucasasu |
| AD-273567.1 | 838 | A-529211.11 | usdTsaudAgdTgagudTadTuuugucasasu |
| AD-273568.1 | 840 | A-529211.12 | usdTsaudAgdTgagudTadTuuugucasasu |
| AD-273569.1 | 842 | A-529211.13 | usdTsaudAgdTgagudTadTuuugucasasu |
| AD-273570.1 | 844 | A-529211.14 | usdTsaudAgdTgagudTadTuuugucasasu |
| AD-273571.1 | 846 | A-529211.15 | usdTsaudAgdTgagudTadTuuugucasasu |
| AD-273572.1 | 848 | A-529211.16 | usdTsaudAgdTgagudTadTuuugucasasu |
| AD-273573.1 | 850 | A-529211.17 | usdTsaudAgdTgagudTadTuuugucasasu |
| AD-273574.1 | 852 | A-529211.18 | usdTsaudAgdTgagudTadTuuugucasasu |
| AD-273575.1 | 854 | A-529211.19 | usdTsaudAgdTgagudTadTuuugucasasu |
| AD-273576.1 | 856 | A-529230.1 | usdTsdAudAgdTgagudTadTuuugucasasu |
| AD-273577.1 | 858 | A-529231.1 | usdTsadTdAgdTgagudTadTuuugucasasu |
| AD-273578.1 | 860 | A-529232.1 | usdTsauagdTgagudTadTuuugucasasu |
| AD-273579.1 | 862 | A-529233.1 | usdTsaudAdGdTgagudTadTuuugucasasu |
| AD-273580.1 | 864 | A-529234.1 | usdTsaudAgugagudTadTuuugucasasu |
| AD-273581.1 | 866 | A-529235.1 | usdTsaudAgdTdGagudTadTuuugucasasu |
| AD-273582.1 | 868 | A-529236.1 | usdTsaudAgdTgdAgudTadTuuugucasasu |
| AD-273583.1 | 870 | A-529237.1 | usdTsaudAgdTgadGudTadTuuugucasasu |
| AD-273584.1 | 872 | A-529238.1 | usdTsaudAgdTgagdTdTadTuuugucasasu |
| AD-273585.1 | 874 | A-529239.1 | usdTsaudAgdTgaguuadTuuugucasasu |
| AD-273586.1 | 876 | A-529240.1 | usdTsaudAgdTgagudTdAdTuuugucasasu |
| AD-273587.1 | 878 | A-529241.1 | usdTsaudAgdTgagudTauuuugucasasu |
| AD-273588.1 | 880 | A-529242.1 | usdTsaudAgdTgagudTadTdTuugucasasu |
| AD-273589.1 | 882 | A-529243.1 | usdTsaudAgdTgagudTadTudTugucasasu |
| AD-273590.1 | 884 | A-529244.1 | usdTsaudAgdTgagudTadTuudTgucasasu |
| AD-273591.1 | 886 | A-529245.1 | usdTsaudAgdTgagudTadTuuudGucasasu |
| AD-273592.1 | 888 | A-529246.1 | usdTsaudAgdTgagudTadTuuugdTcasasu |
| AD-273593.1 | 890 | A-529247.1 | usdTsaudAgdTgagudTadTuuugudCasasu |
| AD-273594.1 | 892 | A-529249.1 | usdAsuudAudAaaaadTadTcuugcuususu |
| AD-273595.1 | 894 | A-529249.2 | usdAsuudAudAaaaadTadTcuugcuususu |

TABLE 1-continued

| Exemplary dsRNA agents | | | |
|---|---|---|---|
| AD-273596.1 | 896 | A-529249.3 | usdAsuudAudAaaaadTadTcuugcuususu |
| AD-273597.1 | 898 | A-529249.4 | usdAsuudAudAaaaadTadTcuugcuususu |
| AD-273598.1 | 900 | A-529249.5 | usdAsuudAudAaaaadTadTcuugcuususu |
| AD-273599.1 | 902 | A-529249.6 | usdAsuudAudAaaaadTadTcuugcuususu |
| AD-273600.1 | 904 | A-529249.7 | usdAsuudAudAaaaadTadTcuugcuususu |
| AD-273601.1 | 906 | A-529249.8 | usdAsuudAudAaaaadTadTcuugcuususu |
| AD-273602.1 | 908 | A-529249.9 | usdAsuudAudAaaaadTadTcuugcuususu |
| AD-273603.1 | 910 | A-529249.10 | usdAsuudAudAaaaadTadTcuugcuususu |
| AD-273604.1 | 912 | A-529249.11 | usdAsuudAudAaaaadTadTcuugcuususu |
| AD-273605.1 | 914 | A-529249.12 | usdAsuudAudAaaaadTadTcuugcuususu |
| AD-273606.1 | 916 | A-529249.13 | usdAsuudAudAaaaadTadTcuugcuususu |
| AD-273607.1 | 918 | A-529249.14 | usdAsuudAudAaaaadTadTcuugcuususu |
| AD-273608.1 | 920 | A-529249.15 | usdAsuudAudAaaaadTadTcuugcuususu |
| AD-273609.1 | 922 | A-529249.16 | usdAsuudAudAaaaadTadTcuugcuususu |
| AD-273610.1 | 924 | A-529249.17 | usdAsuudAudAaaaadTadTcuugcuususu |
| AD-273611.1 | 926 | A-529249.18 | usdAsuudAudAaaaadTadTcuugcuususu |
| AD-273612.1 | 928 | A-529249.19 | usdAsuudAudAaaaadTadTcuugcuususu |
| AD-273613.1 | 930 | A-529267.1 | usdAsdTudAudAaaaadTadTcuugcuususu |
| AD-273614.1 | 932 | A-529268.1 | usdAsudTdAudAaaaadTadTcuugcuususu |
| AD-273615.1 | 934 | A-529269.1 | usdAsuuaudAaaaadTadTcuugcuususu |
| AD-273616.1 | 936 | A-529270.1 | usdAsuudAdTdAaaaadTadTcuugcuususu |
| AD-273617.1 | 938 | A-529271.1 | usdAsuudAuaaaaadTadTcuugcuususu |
| AD-273618.1 | 940 | A-529272.1 | usdAsuudAudAdAaaadTadTcuugcuususu |
| AD-273619.1 | 942 | A-529273.1 | usdAsuudAudAadAaadTadTcuugcuususu |
| AD-273620.1 | 944 | A-529274.1 | usdAsuudAudAaadAadTadTcuugcuususu |
| AD-273621.1 | 946 | A-529275.1 | usdAsuudAudAaaadAdTadTcuugcuususu |
| AD-273622.1 | 948 | A-529276.1 | usdAsuudAudAaaaauadTcuugcuususu |
| AD-273623.1 | 950 | A-529277.1 | usdAsuudAudAaaaadTdAdTcuugcuususu |
| AD-273624.1 | 952 | A-529278.1 | usdAsuudAudAaaaadTaucuugcuususu |
| AD-273625.1 | 954 | A-529279.1 | usdAsuudAudAaaaadTadTdCuugcuususu |
| AD-273626.1 | 956 | A-529280.1 | usdAsuudAudAaaaadTadTcdTugcuususu |
| AD-273627.1 | 958 | A-529281.1 | usdAsuudAudAaaaadTadTcudTgcuususu |
| AD-273628.1 | 960 | A-529282.1 | usdAsuudAudAaaaadTadTcuudGcuususu |
| AD-273629.1 | 962 | A-529283.1 | usdAsuudAudAaaaadTadTcuugdCuususu |
| AD-273630.1 | 964 | A-529284.1 | usdAsuudAudAaaaadTadTcuugcdTususu |

TABLE 2

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-157529.3 | AGT01-related | Cyno hepatocyte | Transfection | | | 8.2 | 1.5 | | | 78.0 | 7.9 |
| AD-191860.3 | AGT01-related | Cyno hepatocyte | Transfection | | | 7.3 | 2.3 | | | 68.1 | 8.9 |
| AD-192113.1 | AGT01-related | Cyno hepatocyte | Transfection | | | 3.8 | 0.4 | | | 59.9 | 9.6 |
| AD-192114.1 | AGT01-related | Cyno hepatocyte | Transfection | | | 4.1 | 0.4 | | | 58.4 | 9.6 |
| AD-192115.1 | AGT01-related | Cyno hepatocyte | Transfection | | | 3.9 | 1.1 | | | 69.6 | 5.6 |
| AD-192116.1 | AGT01-related | Cyno hepatocyte | Transfection | | | 4.8 | 0.6 | | | 62.4 | 5.1 |
| AD-192117.1 | AGT01-related | Cyno hepatocyte | Transfection | | | 4.4 | 0.6 | | | 61.8 | 7.6 |
| AD-192118.1 | AGT01-related | Cyno hepatocyte | Transfection | | | 5.4 | 0.3 | | | 63.7 | 9.0 |
| AD-192119.1 | AGT01-related | Cyno hepatocyte | Transfection | | | 4.3 | 0.4 | | | 61.8 | 6.0 |
| AD-192120.1 | AGT01-related | Cyno hepatocyte | Transfection | | | 4.2 | 0.8 | | | 61.1 | 9.3 |
| AD-157541.2 | Not AGT01-related | Cyno hepatocyte | Transfection | | | 15.9 | 1.7 | | | 85.1 | 3.3 |
| AD-192121.1 | Not AGT01-related | Cyno hepatocyte | Transfection | | | 7.7 | 1.3 | | | 72.2 | 6.5 |
| AD-192122.1 | Not AGT01-related | Cyno hepatocyte | Transfection | | | 19.7 | 2.8 | | | 86.9 | 4.3 |
| AD-192123.1 | Not AGT01-related | Cyno hepatocyte | Transfection | | | 12.6 | 3.0 | | | 76.3 | 4.6 |
| AD-192124.1 | Not AGT01-related | Cyno hepatocyte | Transfection | | | 15.0 | 3.7 | | | 81.4 | 10.1 |
| AD-192125.1 | Not AGT01-related | Cyno hepatocyte | Transfection | | | 8.5 | 0.6 | | | 76.8 | 6.1 |
| AD-192126.1 | Not AGT01-related | Cyno hepatocyte | Transfection | | | 15.1 | 0.9 | | | 92.8 | 6.8 |
| AD-192127.1 | Not AGT01-related | Cyno hepatocyte | Transfection | | | 11.9 | 2.5 | | | 94.6 | 8.1 |
| AD-192128.1 | Not AGT01-related | Cyno hepatocyte | Transfection | | | 9.9 | 2.1 | | | 70.3 | 5.8 |
| AD-157552.3 | Not AGT01-related | Cyno hepatocyte | Transfection | | | 25.7 | 1.7 | | | 91.8 | 1.1 |
| AD-192129.1 | Not AGT01-related | Cyno hepatocyte | Transfection | | | 18.1 | 2.4 | | | 98.0 | 5.3 |
| AD-192130.1 | Not AGT01-related | Cyno hepatocyte | Transfection | | | 10.6 | 1.8 | | | 92.0 | 9.7 |
| AD-192131.1 | Not AGT01-related | Cyno hepatocyte | Transfection | | | 26.7 | 3.2 | | | 107.2 | 9.6 |
| AD-192132.1 | Not AGT01-related | Cyno hepatocyte | Transfection | | | 17.3 | 3.7 | | | 85.8 | 5.5 |
| AD-192133.1 | Not AGT01-related | Cyno hepatocyte | Transfection | | | 10.9 | 1.4 | | | 80.3 | 6.8 |
| AD-192134.1 | Not AGT01-related | Cyno hepatocyte | Transfection | | | 7.2 | 1.3 | | | 70.4 | 6.2 |
| AD-192135.1 | Not AGT01-related | Cyno hepatocyte | Transfection | | | 13.8 | 1.6 | | | 81.6 | 5.8 |
| AD-192136.1 | Not AGT01-related | Cyno hepatocyte | Transfection | | | 8.1 | 1.5 | | | 79.4 | 6.9 |
| AD-192137.1 | Not AGT01-related | Cyno hepatocyte | Transfection | | | 8.4 | 2.0 | | | 78.9 | 7.3 |
| AD-157563.2 | Not AGT01-related | Cyno hepatocyte | Transfection | | | 37.4 | 2.8 | | | 95.9 | 2.9 |
| AD-192138.1 | Not AGT01-related | Cyno hepatocyte | Transfection | | | 20.4 | 2.4 | | | 91.2 | 3.1 |
| AD-192139.1 | Not AGT01-related | Cyno hepatocyte | Transfection | | | 14.3 | 1.2 | | | 94.5 | 3.1 |
| AD-192140.1 | Not AGT01-related | Cyno hepatocyte | Transfection | | | 15.4 | 1.0 | | | 87.3 | 3.1 |
| AD-192141.1 | Not AGT01-related | Cyno hepatocyte | Transfection | | | 8.8 | 1.6 | | | 77.3 | 4.8 |
| AD-192142.1 | Not AGT01-related | Cyno hepatocyte | Transfection | | | 28.4 | 1.5 | | | 103.1 | 4.3 |
| AD-192143.1 | Not AGT01-related | Cyno hepatocyte | Transfection | | | 13.8 | 1.6 | | | 86.0 | 2.8 |
| AD-192144.1 | Not AGT01-related | Cyno hepatocyte | Transfection | | | 22.4 | 2.1 | | | 92.5 | 4.4 |
| AD-192145.1 | Not AGT01-related | Cyno hepatocyte | Transfection | | | 13.5 | 4.2 | | | 87.3 | 5.5 |
| AD-192146.1 | Not AGT01-related | Cyno hepatocyte | Transfection | | | 8.6 | 1.1 | | | 85.5 | 5.9 |
| AD-157574.2 | Not AGT01-related | Cyno hepatocyte | Transfection | | | 35.5 | 8.5 | | | 112.2 | 8.3 |
| AD-192147.1 | Not AGT01-related | Cyno hepatocyte | Transfection | | | 17.0 | 3.4 | | | 90.6 | 5.3 |
| AD-192148.1 | Not AGT01-related | Cyno hepatocyte | Transfection | | | 12.4 | 1.6 | | | 82.5 | 7.1 |

TABLE 2-continued

| Duplex Number | Restrictions | Cell Type | Method | % of Control 50 nM (Avg) | 50 nM (SD) | 10 nM (Avg) | 10 nM (SD) | 1 nM (Avg) | 1 nM (SD) | 0.1 nM (Avg) | 0.1 nM (SD) |
|---|---|---|---|---|---|---|---|---|---|---|---|
| AD-192149.1 | Not AGT01-related | Cyno hepatocyte | Transfection | | | 17.9 | 1.0 | | | 87.8 | 3.5 |
| AD-192150.1 | Not AGT01-related | Cyno hepatocyte | Transfection | | | 9.7 | 2.6 | | | 78.3 | 6.3 |
| AD-192151.1 | Not AGT01-related | Cyno hepatocyte | Transfection | | | 20.1 | 0.9 | | | 89.0 | 3.7 |
| AD-192152.1 | Not AGT01-related | Cyno hepatocyte | Transfection | | | 7.5 | 1.3 | | | 80.6 | 4.6 |
| AD-192153.1 | Not AGT01-related | Cyno hepatocyte | Transfection | | | 13.1 | 1.2 | | | 86.9 | 4.3 |
| AD-192154.1 | Not AGT01-related | Cyno hepatocyte | Transfection | | | 15.4 | 3.9 | | | 94.9 | 11.0 |
| AD-192155.1 | Not AGT01-related | Cyno hepatocyte | Transfection | | | 10.2 | 2.8 | | | 85.2 | 3.2 |
| AD-157584.2 | Not AGT01-related | Cyno hepatocyte | Transfection | | | 91.7 | 1.6 | | | 99.3 | 3.4 |
| AD-192156.1 | Not AGT01-related | Cyno hepatocyte | Transfection | | | 61.9 | 3.3 | | | 96.8 | 4.5 |
| AD-192157.1 | Not AGT01-related | Cyno hepatocyte | Transfection | | | 36.8 | 2.0 | | | 102.6 | 2.1 |
| AD-192158.1 | Not AGT01-related | Cyno hepatocyte | Transfection | | | 96.3 | 16.3 | | | 118.3 | 17.2 |
| AD-192159.1 | Not AGT01-related | Cyno hepatocyte | Transfection | | | 79.3 | 17.3 | | | 105.2 | 8.9 |
| AD-192160.1 | Not AGT01-related | Cyno hepatocyte | Transfection | | | 65.5 | 3.7 | | | 97.0 | 6.1 |
| AD-192161.1 | Not AGT01-related | Cyno hepatocyte | Transfection | | | 47.4 | 4.6 | | | 99.6 | 4.3 |
| AD-192162.1 | Not AGT01-related | Cyno hepatocyte | Transfection | | | 62.1 | 4.7 | | | 95.4 | 2.8 |
| AD-192163.1 | Not AGT01-related | Cyno hepatocyte | Transfection | | | 51.8 | 1.8 | | | 97.9 | 3.1 |
| AD-192164.1 | Not AGT01-related | Cyno hepatocyte | Transfection | | | 31.6 | 2.8 | | | 97.4 | 7.6 |
| AD-264555.1 | Unknown | Primary Mouse Hepatocytes | Transfection | | | 20.2 | 0.7 | | | 74.4 | 4.9 |
| AD-264556.1 | Unknown | Primary Mouse Hepatocytes | Transfection | | | 21.6 | 3.4 | | | 70.0 | 7.7 |
| AD-264557.1 | Unknown | Primary Mouse Hepatocytes | Transfection | | | 62.6 | 4.7 | | | 91.3 | 10.8 |
| AD-264558.1 | Unknown | Primary Mouse Hepatocytes | Transfection | | | 22.8 | 2.3 | | | 52.9 | 4.7 |
| AD-264559.1 | Unknown | Primary Mouse Hepatocytes | Transfection | | | 77.4 | 5.4 | | | 105.0 | 5.8 |
| AD-264560.1 | Unknown | Primary Mouse Hepatocytes | Transfection | | | 51.4 | 5.6 | | | 106.6 | 5.5 |
| AD-264561.1 | Unknown | Primary Mouse Hepatocytes | Transfection | | | 19.0 | 3.4 | | | 69.2 | 3.5 |
| AD-264562.1 | Unknown | Primary Mouse Hepatocytes | Transfection | | | 57.9 | 8.0 | | | 91.1 | 14.2 |
| AD-264563.1 | Unknown | Primary Mouse Hepatocytes | Transfection | | | 88.3 | 5.6 | | | 106.6 | 4.9 |
| AD-264564.1 | Unknown | Primary Mouse Hepatocytes | Transfection | | | 23.5 | 2.2 | | | 81.6 | 2.8 |
| AD-264565.1 | Unknown | Primary Mouse Hepatocytes | Transfection | | | 63.5 | 6.2 | | | 106.3 | 1.1 |
| AD-264566.1 | Unknown | Primary Mouse Hepatocytes | Transfection | | | 91.8 | 6.5 | | | 98.5 | 9.4 |
| AD-264567.1 | Unknown | Primary Mouse Hepatocytes | Transfection | | | 18.5 | 1.6 | | | 71.2 | 3.8 |
| AD-264568.1 | Unknown | Primary Mouse Hepatocytes | Transfection | | | 53.7 | 4.4 | | | 98.4 | 16.1 |
| AD-264569.1 | Unknown | Primary Mouse Hepatocytes | Transfection | | | 56.4 | 4.4 | | | 93.5 | 13.0 |
| AD-264570.1 | Unknown | Primary Mouse Hepatocytes | Transfection | | | 52.9 | 6.0 | | | 91.0 | 26.7 |
| AD-264571.1 | Unknown | Primary Mouse Hepatocytes | Transfection | | | 20.6 | 2.1 | | | 72.0 | 1.8 |
| AD-264572.1 | Unknown | Primary Mouse Hepatocytes | Transfection | | | 99.5 | 19.3 | | | 78.0 | 18.8 |
| AD-264573.1 | Unknown | Primary Mouse Hepatocytes | Transfection | | | 73.2 | 4.4 | | | 96.8 | 17.1 |
| AD-264574.1 | Unknown | Primary Mouse Hepatocytes | Transfection | | | 74.3 | 10.5 | | | 104.4 | 5.3 |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-264575.1 | Unknown | Primary Mouse Hepatocytes | Transfection | | | 39.6 | 2.2 | | | 75.9 | 26.0 |
| AD-264576.1 | Unknown | Primary Mouse Hepatocytes | Transfection | | | 25.0 | 2.1 | | | 80.7 | 7.1 |
| AD-264577.1 | Unknown | Primary Mouse Hepatocytes | Transfection | | | 55.3 | 3.7 | | | 89.7 | 10.3 |
| AD-264578.1 | Unknown | Primary Mouse Hepatocytes | Transfection | | | 22.6 | 1.7 | | | 86.6 | 14.2 |
| AD-264579.1 | Unknown | Primary Mouse Hepatocytes | Transfection | | | 30.6 | 2.0 | | | 85.6 | 4.4 |
| AD-264580.1 | Unknown | Primary Mouse Hepatocytes | Transfection | | | 11.2 | 2.2 | | | 36.8 | 6.4 |
| AD-264581.1 | Unknown | Primary Mouse Hepatocytes | Transfection | | | 22.7 | 1.4 | | | 78.6 | 8.7 |
| AD-264582.1 | Unknown | Primary Mouse Hepatocytes | Transfection | | | 26.3 | 6.2 | | | 77.2 | 8.5 |
| AD-264583.1 | Unknown | Primary Mouse Hepatocytes | Transfection | | | 24.4 | 2.3 | | | 60.5 | 8.1 |
| AD-264584.1 | Unknown | Primary Mouse Hepatocytes | Transfection | | | 46.2 | 4.4 | | | 94.4 | 7.1 |
| AD-264585.1 | Unknown | Primary Mouse Hepatocytes | Transfection | | | 20.0 | 1.9 | | | 85.5 | 5.9 |
| AD-264586.1 | Unknown | Primary Mouse Hepatocytes | Transfection | | | 32.4 | 7.5 | | | 88.8 | 29.5 |
| AD-264587.1 | Unknown | Primary Mouse Hepatocytes | Transfection | | | 21.8 | 1.4 | | | 81.5 | 8.8 |
| AD-264588.1 | Unknown | Primary Mouse Hepatocytes | Transfection | | | 13.0 | 1.0 | | | 68.2 | 3.3 |
| AD-264589.1 | Unknown | Primary Mouse Hepatocytes | Transfection | | | 14.9 | 0.7 | | | 75.1 | 8.0 |
| AD-264590.1 | Unknown | Primary Mouse Hepatocytes | Transfection | | | 31.7 | 7.8 | | | 96.3 | 10.1 |
| AD-264591.1 | Unknown | Primary Mouse Hepatocytes | Transfection | | | 77.8 | 1.7 | | | 99.0 | 1.4 |
| AD-264592.1 | Unknown | Primary Mouse Hepatocytes | Transfection | | | 23.3 | 2.9 | | | 71.0 | 6.5 |
| AD-264593.1 | Unknown | Primary Mouse Hepatocytes | Transfection | | | 49.1 | 7.4 | | | 92.8 | 6.4 |
| AD-264594.1 | Unknown | Primary Mouse Hepatocytes | Transfection | | | 40.2 | 3.7 | | | 101.0 | 9.9 |
| AD-264595.1 | Unknown | Primary Mouse Hepatocytes | Transfection | | | 31.8 | 2.8 | | | 84.4 | 6.5 |
| AD-264596.1 | Unknown | Primary Mouse Hepatocytes | Transfection | | | 17.8 | 0.7 | | | 98.7 | 50.8 |
| AD-264597.1 | Unknown | Primary Mouse Hepatocytes | Transfection | | | 18.2 | 3.1 | | | 84.4 | 6.9 |
| AD-264598.1 | Unknown | Primary Mouse Hepatocytes | Transfection | | | 35.3 | 3.1 | | | 90.8 | 7.9 |
| AD-264599.1 | Unknown | Primary Mouse Hepatocytes | Transfection | | | 40.7 | 3.4 | | | 95.3 | 3.8 |
| AD-264600.1 | Unknown | Primary Mouse Hepatocytes | Transfection | | | 15.7 | 0.4 | | | 67.2 | 5.4 |
| AD-264601.1 | Unknown | Primary Mouse Hepatocytes | Transfection | | | 22.6 | 1.4 | | | 73.0 | 5.3 |
| AD-237788.1 | Unknown | Unknown | Transfection | | | 28.1 | 4.6 | | | 66.3 | 18.2 |
| AD-237789.1 | Unknown | Unknown | Transfection | | | 17.3 | 4.7 | | | 51.4 | 13.7 |
| AD-237790.1 | Unknown | Unknown | Transfection | | | 18.0 | 1.7 | | | 44.1 | 22.0 |
| AD-237791.1 | Unknown | Unknown | Transfection | | | 21.2 | 11.5 | | | 47.9 | 19.5 |
| AD-237792.1 | Unknown | Unknown | Transfection | | | 23.4 | 2.4 | | | 70.7 | 16.6 |
| AD-237793.1 | Unknown | Unknown | Transfection | | | 14.6 | 2.8 | | | 47.3 | 1.1 |
| AD-237794.1 | Unknown | Unknown | Transfection | | | 50.2 | 8.4 | | | 96.6 | 16.1 |
| AD-237795.1 | Unknown | Unknown | Transfection | | | 52.0 | 26.8 | | | 82.7 | 13.0 |
| AD-237796.1 | Unknown | Unknown | Transfection | | | 25.3 | 3.3 | | | 65.3 | 18.8 |
| AD-237797.1 | Unknown | Unknown | Transfection | | | 39.4 | 16.7 | | | 89.1 | 8.2 |
| AD-237798.1 | Unknown | Unknown | Transfection | | | 51.0 | 1.7 | | | 81.6 | 19.7 |
| AD-237799.1 | Unknown | Unknown | Transfection | | | 78.9 | 33.6 | | | 81.1 | 22.9 |
| AD-237800.1 | Unknown | Unknown | Transfection | | | 41.0 | 16.2 | | | 102.1 | 16.3 |
| AD-237801.1 | Unknown | Unknown | Transfection | | | 79.4 | 12.9 | | | 108.9 | 8.2 |
| AD-237802.1 | Unknown | Unknown | Transfection | | | 56.2 | 4.5 | | | 91.5 | 14.4 |
| AD-237803.1 | Unknown | Unknown | Transfection | | | 48.4 | 7.3 | | | 61.9 | 25.2 |
| AD-237804.1 | Unknown | Unknown | Transfection | | | 19.8 | 7.3 | | | 70.3 | 7.9 |
| AD-237805.1 | Unknown | Unknown | Transfection | | | 83.1 | 8.9 | | | 106.0 | 13.8 |
| AD-237806.1 | Unknown | Unknown | Transfection | | | 42.1 | 17.0 | | | 99.1 | 9.4 |
| AD-237807.1 | Unknown | Unknown | Transfection | | | 74.6 | 24.0 | | | 75.6 | 18.7 |
| AD-237808.1 | Unknown | Unknown | Transfection | | | 33.4 | 4.6 | | | 99.3 | 20.1 |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-237809.1 | Unknown | Unknown | Transfection | | | 60.1 | 13.3 | | | 99.7 | 11.2 |
| AD-237810.1 | Unknown | Unknown | Transfection | | | 61.2 | 6.9 | | | 91.7 | 14.1 |
| AD-237811.1 | Unknown | Unknown | Transfection | | | 49.1 | 6.9 | | | 96.2 | 0.6 |
| AD-237812.1 | Unknown | Unknown | Transfection | | | 64.6 | 5.3 | | | 82.0 | 0.5 |
| AD-237813.1 | Unknown | Unknown | Transfection | | | 24.0 | 5.7 | | | 122.3 | 32.4 |
| AD-237814.1 | Unknown | Unknown | Transfection | | | 52.0 | 7.9 | | | 122.6 | 37.0 |
| AD-237815.1 | Unknown | Unknown | Transfection | | | 45.6 | 6.4 | | | 112.5 | 39.3 |
| AD-237816.1 | Unknown | Unknown | Transfection | | | 56.1 | 7.2 | | | 96.0 | 10.2 |
| AD-237817.1 | Unknown | Unknown | Transfection | | | 74.0 | 10.0 | | | 94.4 | 18.4 |
| AD-237818.1 | Unknown | Unknown | Transfection | | | 35.3 | 9.9 | | | 95.8 | 9.9 |
| AD-237819.1 | Unknown | Unknown | Transfection | | | 45.1 | 8.8 | | | 113.1 | 27.2 |
| AD-237820.1 | Unknown | Unknown | Transfection | | | 76.9 | 17.6 | | | 97.6 | 15.0 |
| AD-237821.1 | Unknown | Unknown | Transfection | | | 78.4 | 15.3 | | | 88.2 | 11.1 |
| AD-237822.1 | Unknown | Unknown | Transfection | | | 66.9 | 13.2 | | | 112.1 | 14.5 |
| AD-237823.1 | Unknown | Unknown | Transfection | | | 67.1 | 10.0 | | | 117.0 | 16.5 |
| AD-237824.1 | Unknown | Unknown | Transfection | | | 64.8 | 10.8 | | | 106.0 | 23.5 |
| AD-237825.1 | Unknown | Unknown | Transfection | | | 79.7 | 11.6 | | | 84.3 | 4.1 |
| AD-237826.1 | Unknown | Unknown | Transfection | | | 42.7 | 8.3 | | | 101.6 | 13.9 |
| AD-237827.1 | Unknown | Unknown | Transfection | | | 39.3 | 11.3 | | | 109.6 | 14.9 |
| AD-237828.1 | Unknown | Unknown | Transfection | | | 92.3 | 8.0 | | | 97.8 | 13.7 |
| AD-237829.1 | Unknown | Unknown | Transfection | | | 68.4 | 11.9 | | | 95.9 | 15.5 |
| AD-237830.1 | Unknown | Unknown | Transfection | | | 82.9 | 5.9 | | | 68.1 | 33.3 |
| AD-237831.1 | Unknown | Unknown | Transfection | | | 33.6 | 21.1 | | | 101.6 | 15.0 |
| AD-237832.1 | Unknown | Unknown | Transfection | | | 107.6 | 19.5 | | | 104.8 | 18.4 |
| AD-237833.1 | Unknown | Unknown | Transfection | | | 46.8 | 14.4 | | | 83.9 | 12.9 |
| AD-237834.1 | Unknown | Unknown | Transfection | | | 79.5 | 21.3 | | | 110.0 | 22.4 |
| AD-237835.1 | Unknown | Unknown | Transfection | | | 57.9 | 17.2 | | | 101.2 | 11.1 |
| AD-237836.1 | Unknown | Unknown | Transfection | | | 14.6 | 4.7 | | | 75.6 | 17.7 |
| AD-237837.1 | Unknown | Unknown | Transfection | | | 63.6 | 14.2 | | | 81.0 | 6.2 |
| AD-237838.1 | Unknown | Unknown | Transfection | | | 64.1 | 10.4 | | | 65.2 | 6.3 |
| AD-237839.1 | Unknown | Unknown | Transfection | | | 67.8 | 7.7 | | | 88.6 | 24.4 |
| AD-237840.1 | Unknown | Unknown | Transfection | | | 78.4 | 8.1 | | | 92.8 | 16.2 |
| AD-237841.1 | Unknown | Unknown | Transfection | | | 56.8 | 25.9 | | | 87.6 | 9.1 |
| AD-237842.1 | Unknown | Unknown | Transfection | | | 27.7 | 4.7 | | | 67.9 | 13.0 |
| AD-237843.1 | Unknown | Unknown | Transfection | | | 47.9 | 13.1 | | | 119.3 | 12.3 |
| AD-237844.1 | Unknown | Unknown | Transfection | | | 73.2 | 12.8 | | | 101.2 | 11.5 |
| AD-237845.1 | Unknown | Unknown | Transfection | | | 81.8 | 8.7 | | | 99.3 | 5.3 |
| AD-237846.1 | Unknown | Unknown | Transfection | | | 27.7 | 3.1 | | | 62.0 | 20.8 |
| AD-237847.1 | Unknown | Unknown | Transfection | | | 84.6 | 12.9 | | | 120.3 | 16.3 |
| AD-237848.1 | Unknown | Unknown | Transfection | | | 60.6 | 14.9 | | | 106.2 | 16.6 |
| AD-237849.1 | Unknown | Unknown | Transfection | | | 76.1 | 4.3 | | | 94.3 | 5.6 |
| AD-237850.1 | Unknown | Unknown | Transfection | | | 75.4 | 21.5 | | | 83.3 | 38.0 |
| AD-237851.1 | Unknown | Unknown | Transfection | | | 63.0 | 22.6 | | | 108.0 | 24.4 |
| AD-237852.1 | Unknown | Unknown | Transfection | | | 88.9 | 14.3 | | | 111.4 | 7.1 |
| AD-237853.1 | Unknown | Unknown | Transfection | | | 49.5 | 7.1 | | | 97.7 | 12.4 |
| AD-237854.1 | Unknown | Unknown | Transfection | | | 64.7 | 24.0 | | | 65.8 | 27.2 |
| AD-237855.1 | Unknown | Unknown | Transfection | | | 71.6 | 14.6 | | | 121.0 | 6.4 |
| AD-237856.1 | Unknown | Unknown | Transfection | | | 93.1 | 12.6 | | | 112.3 | 18.9 |
| AD-237857.1 | Unknown | Unknown | Transfection | | | 95.8 | 22.7 | | | 106.9 | 17.1 |
| AD-237858.1 | Unknown | Unknown | Transfection | | | 83.0 | 16.7 | | | 93.3 | 23.7 |
| AD-237859.1 | Unknown | Unknown | Transfection | | | 111.8 | 19.6 | | | 129.9 | 34.3 |
| AD-237860.1 | Unknown | Unknown | Transfection | | | 94.0 | 28.8 | | | 112.1 | 14.3 |
| AD-237861.1 | Unknown | Unknown | Transfection | | | 82.0 | 7.9 | | | 94.7 | 30.5 |
| AD-237862.1 | Unknown | Unknown | Transfection | | | 102.1 | 27.9 | | | 104.1 | 30.0 |
| AD-237863.1 | Unknown | Unknown | Transfection | | | 103.5 | 28.9 | | | 120.3 | 12.5 |
| AD-237864.1 | Unknown | Unknown | Transfection | | | 99.3 | 15.4 | | | 105.9 | 9.4 |
| AD-237865.1 | Unknown | Unknown | Transfection | | | 72.8 | 12.7 | | | 115.3 | 22.1 |
| AD-237866.1 | Unknown | Unknown | Transfection | | | 94.9 | 19.5 | | | 73.4 | 12.9 |
| AD-218795.6 | Unknown | Unknown | Transfection | 17.0 | 3.4 | 15.3 | 3.5 | 21.6 | 4.7 | | |
| AD-238829.1 | Unknown | Unknown | Transfection | 15.2 | 5.7 | 18.8 | 4.7 | 18.5 | 5.4 | | |
| AD-238830.1 | Unknown | Unknown | Transfection | 18.1 | 2.5 | 19.7 | 2.0 | 23.3 | 4.5 | | |
| AD-238831.1 | Unknown | Unknown | Transfection | 12.9 | 2.5 | 19.1 | 5.5 | 16.4 | 1.4 | | |
| AD-238832.1 | Unknown | Unknown | Transfection | 19.5 | 2.6 | 18.0 | 4.0 | 21.4 | 0.7 | | |
| AD-238833.1 | Unknown | Unknown | Transfection | 13.3 | 2.5 | 15.1 | 3.8 | 26.2 | 2.6 | | |
| AD-238834.1 | Unknown | Unknown | Transfection | 12.1 | 3.0 | 8.2 | 2.3 | 15.9 | 1.4 | | |
| AD-238835.1 | Unknown | Unknown | Transfection | 13.5 | 3.1 | 13.5 | 1.5 | 20.1 | 2.4 | | |
| AD-238836.1 | Unknown | Unknown | Transfection | 13.7 | 3.1 | 12.2 | 1.8 | 25.1 | 3.3 | | |
| AD-238837.1 | Unknown | Unknown | Transfection | 10.0 | 2.2 | 10.4 | 3.2 | 15.3 | 0.9 | | |
| AD-238838.1 | Unknown | Unknown | Transfection | 26.7 | 3.4 | 22.6 | 1.8 | 30.0 | 4.8 | | |
| AD-238839.1 | Unknown | Unknown | Transfection | 18.8 | 4.5 | 15.5 | 4.0 | 27.1 | 3.5 | | |
| AD-238840.1 | Unknown | Unknown | Transfection | 11.3 | 1.8 | 13.0 | 2.2 | 14.9 | 2.1 | | |
| AD-238841.1 | Unknown | Unknown | Transfection | 10.5 | 4.7 | 8.3 | 2.9 | 14.8 | 1.1 | | |
| AD-238842.1 | Unknown | Unknown | Transfection | 15.0 | 2.1 | 17.6 | 3.1 | 24.8 | 5.5 | | |
| AD-238843.1 | Unknown | Unknown | Transfection | 12.6 | 3.1 | 12.0 | 1.0 | 17.5 | 4.1 | | |
| AD-238844.1 | Unknown | Unknown | Transfection | 8.6 | 4.3 | 11.8 | 1.3 | 11.6 | 1.6 | | |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-238845.1 | Unknown | Unknown | Transfection | 10.4 | 2.1 | 9.2 | 0.8 | 11.9 | 3.1 | | |
| AD-238846.1 | Unknown | Unknown | Transfection | 9.0 | 3.0 | 10.8 | 0.1 | 11.9 | 2.8 | | |
| AD-238847.1 | Unknown | Unknown | Transfection | 10.2 | 2.2 | 11.5 | 2.9 | 13.1 | 2.3 | | |
| AD-238848.1 | Unknown | Unknown | Transfection | 12.0 | 1.2 | 12.0 | 1.2 | 14.8 | 2.6 | | |
| AD-238849.1 | Unknown | Unknown | Transfection | 9.0 | 1.9 | 12.3 | 2.3 | 20.2 | 3.3 | | |
| AD-238850.1 | Unknown | Unknown | Transfection | 10.7 | 1.4 | 10.8 | 4.2 | 16.9 | 4.4 | | |
| AD-238851.1 | Unknown | Unknown | Transfection | 16.1 | 2.7 | 19.4 | 2.3 | 23.3 | 3.0 | | |
| AD-238852.1 | Unknown | Unknown | Transfection | 13.8 | 3.5 | 13.6 | 0.5 | 20.2 | 4.4 | | |
| AD-238853.1 | Unknown | Unknown | Transfection | 9.9 | 3.4 | 10.0 | 0.4 | 13.1 | 2.3 | | |
| AD-238854.1 | Unknown | Unknown | Transfection | 6.7 | 2.0 | 10.1 | 1.9 | 13.5 | 0.9 | | |
| AD-238855.1 | Unknown | Unknown | Transfection | 14.8 | 1.6 | 14.2 | 2.5 | 23.6 | 2.6 | | |
| AD-238856.1 | Unknown | Unknown | Transfection | 11.9 | 1.7 | 12.5 | 5.0 | 13.4 | 2.3 | | |
| AD-238857.1 | Unknown | Unknown | Transfection | 12.2 | 1.8 | 12.3 | 2.5 | 16.0 | 4.5 | | |
| AD-238858.1 | Unknown | Unknown | Transfection | 15.0 | 3.7 | 17.0 | 5.3 | 18.0 | 4.2 | | |
| AD-238859.1 | Unknown | Unknown | Transfection | 11.2 | 1.8 | 9.9 | 0.9 | 17.2 | 2.3 | | |
| AD-238860.1 | Unknown | Unknown | Transfection | 16.1 | 2.7 | 12.9 | 1.8 | 15.3 | 4.4 | | |
| AD-238861.1 | Unknown | Unknown | Transfection | 6.3 | 2.6 | 7.9 | 1.8 | 10.3 | 1.4 | | |
| AD-238862.1 | Unknown | Unknown | Transfection | 10.3 | 5.2 | 8.5 | 2.0 | 9.7 | 3.7 | | |
| AD-238863.1 | Unknown | Unknown | Transfection | 10.4 | 2.9 | 13.4 | 3.2 | 17.8 | 4.5 | | |
| AD-192134.4 | Not AGT01-related | Unknown | Transfection | 43.0 | 17.5 | 44.1 | 10.6 | 68.0 | 15.6 | | |
| AD-157553.2 | Not AGT01-related | Unknown | Transfection | 118.9 | 46.7 | 87.1 | 19.3 | 99.0 | 14.4 | | |
| AD-238872.1 | Not AGT01-related | Unknown | Transfection | 91.9 | 42.5 | 90.0 | 28.9 | 90.8 | 19.0 | | |
| AD-238873.1 | Not AGT01-related | Unknown | Transfection | 57.6 | 22.2 | 64.5 | 10.0 | 83.0 | 16.0 | | |
| AD-238874.1 | Not AGT01-related | Unknown | Transfection | 39.9 | 16.4 | 61.8 | 9.8 | 67.9 | 13.6 | | |
| AD-238875.1 | Not AGT01-related | Unknown | Transfection | 26.5 | 9.3 | 49.0 | 4.9 | 75.6 | 10.9 | | |
| AD-238876.1 | Not AGT01-related | Unknown | Transfection | 17.0 | 3.4 | 38.4 | 6.9 | 67.0 | 13.0 | | |
| AD-192129.4 | Not AGT01-related | Unknown | Transfection | 57.1 | 17.5 | 61.6 | 11.4 | 90.7 | 0.9 | | |
| AD-238877.1 | Not AGT01-related | Unknown | Transfection | 52.3 | 20.5 | 71.1 | 18.7 | 82.0 | 7.8 | | |
| AD-157552.4 | Not AGT01-related | Unknown | Transfection | 54.4 | 4.7 | 95.9 | 13.6 | 91.3 | 4.1 | | |
| AD-238878.1 | Not AGT01-related | Unknown | Transfection | 91.3 | 20.5 | 100.3 | 19.4 | 92.5 | 17.9 | | |
| AD-238879.1 | Not AGT01-related | Unknown | Transfection | 36.4 | 12.1 | 70.8 | 16.8 | 93.8 | 8.9 | | |
| AD-238880.1 | Not AGT01-related | Unknown | Transfection | 58.0 | 20.3 | 68.5 | 12.0 | 77.6 | 9.8 | | |
| AD-192135.2 | Not AGT01-related | Unknown | Transfection | 50.3 | 14.9 | 60.1 | 23.2 | 93.9 | 20.5 | | |
| AD-238881.1 | Not AGT01-related | Unknown | Transfection | 74.0 | 2.7 | 84.4 | 7.1 | 101.7 | 13.9 | | |
| AD-238882.1 | Not AGT01-related | Unknown | Transfection | 51.2 | 15.6 | 73.6 | 15.0 | 102.5 | 19.2 | | |
| AD-238883.1 | Not AGT01-related | Unknown | Transfection | 48.9 | 18.6 | 61.9 | 20.8 | 94.6 | 14.5 | | |
| AD-238884.1 | Not AGT01-related | Unknown | Transfection | 30.2 | 10.6 | 52.0 | 13.7 | 83.7 | 10.9 | | |
| AD-238885.1 | Not AGT01-related | Unknown | Transfection | 32.2 | 17.4 | 37.5 | 4.8 | 77.7 | 11.9 | | |
| AD-238886.1 | Not AGT01-related | Unknown | Transfection | 25.0 | 6.7 | 39.2 | 9.7 | 74.2 | 12.6 | | |
| AD-238887.1 | Not AGT01-related | Unknown | Transfection | 40.8 | 9.8 | 65.4 | 11.8 | 105.2 | 25.1 | | |
| AD-238888.1 | Not AGT01-related | Unknown | Transfection | 40.8 | 15.7 | 71.0 | 20.9 | 89.9 | 5.1 | | |
| AD-238889.1 | Not AGT01-related | Unknown | Transfection | 39.5 | 21.1 | 76.5 | 24.9 | 78.9 | 10.1 | | |
| AD-238890.1 | Not AGT01-related | Unknown | Transfection | 49.9 | 8.5 | 73.1 | 5.6 | 102.4 | 16.9 | | |
| AD-238891.1 | Not AGT01-related | Unknown | Transfection | 45.9 | 27.7 | 54.1 | 25.3 | 80.0 | 8.1 | | |
| AD-238892.1 | Not AGT01-related | Unknown | Transfection | 38.7 | 11.9 | 65.6 | 9.1 | 80.4 | 9.8 | | |
| AD-238893.1 | Not AGT01-related | Unknown | Transfection | 27.6 | 10.1 | 46.8 | 7.0 | 79.8 | 8.0 | | |
| AD-238894.1 | Not AGT01-related | Unknown | Transfection | 36.6 | 10.6 | 44.0 | 14.6 | 90.5 | 5.7 | | |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-238895.1 | Not AGT01-related | Unknown | Transfection | 38.6 | 22.6 | 39.0 | 7.0 | 70.8 | 9.9 | | |
| AD-238896.1 | Not AGT01-related | Unknown | Transfection | 27.5 | 12.5 | 49.1 | 5.1 | 71.6 | 11.4 | | |
| AD-238897.1 | Not AGT01-related | Unknown | Transfection | 26.0 | 8.4 | 48.3 | 8.6 | 63.1 | 16.4 | | |
| AD-238898.1 | Not AGT01-related | Unknown | Transfection | 40.8 | 17.1 | 53.3 | 10.3 | 84.5 | 21.6 | | |
| AD-238899.1 | Not AGT01-related | Unknown | Transfection | 14.5 | 5.6 | 48.6 | 13.3 | 65.8 | 4.2 | | |
| AD-238900.1 | Not AGT01-related | Unknown | Transfection | 28.0 | 7.4 | 38.0 | 10.0 | 77.8 | 17.4 | | |
| AD-238901.1 | Not AGT01-related | Unknown | Transfection | 42.9 | 11.9 | 57.6 | 22.4 | 77.0 | 27.2 | | |
| AD-238902.1 | Not AGT01-related | Unknown | Transfection | 31.7 | 6.0 | 43.9 | 11.1 | 96.3 | 22.3 | | |
| AD-264561.2 | Unknown | Unknown | Transfection | | | 17.6 | 4.5 | | | 66.6 | 22.3 |
| AD-273421.1 | Unknown | Unknown | Transfection | | | 16.8 | 7.3 | | | 79.3 | 26.5 |
| AD-273422.1 | Unknown | Unknown | Transfection | | | 18.0 | 3.9 | | | 54.8 | 25.8 |
| AD-273423.1 | Unknown | Unknown | Transfection | | | 15.3 | 6.9 | | | 72.7 | 24.8 |
| AD-273424.1 | Unknown | Unknown | Transfection | | | 12.9 | 4.9 | | | 68.3 | 22.5 |
| AD-273425.1 | Unknown | Unknown | Transfection | | | 11.7 | 1.4 | | | 69.1 | 23.9 |
| AD-273426.1 | Unknown | Unknown | Transfection | | | 14.4 | 6.4 | | | 59.4 | 10.8 |
| AD-273427.1 | Unknown | Unknown | Transfection | | | 16.1 | 6.5 | | | 45.7 | 4.0 |
| AD-273428.1 | Unknown | Unknown | Transfection | | | 13.8 | 5.1 | | | 69.6 | 26.0 |
| AD-273429.1 | Unknown | Unknown | Transfection | | | 17.2 | 2.9 | | | 73.1 | 26.9 |
| AD-273430.1 | Unknown | Unknown | Transfection | | | 14.0 | 2.9 | | | 75.8 | 14.7 |
| AD-273431.1 | Unknown | Unknown | Transfection | | | 16.3 | 7.5 | | | 67.7 | 19.8 |
| AD-273432.1 | Unknown | Unknown | Transfection | | | 16.9 | 6.3 | | | 71.8 | 19.5 |
| AD-273433.1 | Unknown | Unknown | Transfection | | | 16.4 | 5.5 | | | 64.4 | 20.0 |
| AD-273434.1 | Unknown | Unknown | Transfection | | | 13.5 | 6.7 | | | 59.0 | 15.8 |
| AD-273435.1 | Unknown | Unknown | Transfection | | | 11.1 | 3.3 | | | 75.7 | 18.3 |
| AD-273436.1 | Unknown | Unknown | Transfection | | | 11.8 | 3.8 | | | 63.5 | 17.9 |
| AD-273437.1 | Unknown | Unknown | Transfection | | | 17.2 | 7.3 | | | 46.0 | 7.2 |
| AD-273438.1 | Unknown | Unknown | Transfection | | | 12.7 | 5.7 | | | 47.0 | 12.1 |
| AD-273439.1 | Unknown | Unknown | Transfection | | | 14.9 | 6.0 | | | 53.6 | 6.0 |
| AD-273440.1 | Unknown | Unknown | Transfection | | | 22.5 | 6.5 | | | 65.8 | 5.8 |
| AD-273441.1 | Unknown | Unknown | Transfection | | | 22.0 | 12.6 | | | 69.1 | 9.7 |
| AD-273442.1 | Unknown | Unknown | Transfection | | | 13.0 | 4.4 | | | 67.7 | 18.9 |
| AD-273443.1 | Unknown | Unknown | Transfection | | | 16.4 | 11.8 | | | 55.6 | 9.3 |
| AD-273444.1 | Unknown | Unknown | Transfection | | | 16.4 | 5.4 | | | 74.0 | 11.7 |
| AD-273445.1 | Unknown | Unknown | Transfection | | | 20.6 | 4.1 | | | 56.1 | 12.1 |
| AD-273446.1 | Unknown | Unknown | Transfection | | | 13.8 | 3.5 | | | 66.8 | 24.8 |
| AD-273447.1 | Unknown | Unknown | Transfection | | | 16.5 | 4.8 | | | 63.4 | 22.8 |
| AD-273448.1 | Unknown | Unknown | Transfection | | | 14.9 | 9.1 | | | 67.4 | 13.9 |
| AD-273449.1 | Unknown | Unknown | Transfection | | | 17.8 | 7.6 | | | 60.0 | 25.3 |
| AD-273450.1 | Unknown | Unknown | Transfection | | | 13.4 | 3.5 | | | 58.8 | 22.0 |
| AD-273451.1 | Unknown | Unknown | Transfection | | | 17.4 | 9.7 | | | 65.4 | 9.0 |
| AD-273452.1 | Unknown | Unknown | Transfection | | | 14.3 | 1.4 | | | 73.6 | 9.7 |
| AD-273453.1 | Unknown | Unknown | Transfection | | | 16.6 | 4.8 | | | 51.1 | 12.5 |
| AD-273454.1 | Unknown | Unknown | Transfection | | | 16.1 | 4.2 | | | 58.4 | 8.1 |
| AD-273455.1 | Unknown | Unknown | Transfection | | | 20.2 | 6.7 | | | 63.9 | 19.0 |
| AD-273456.1 | Unknown | Unknown | Transfection | | | 12.9 | 3.7 | | | 71.0 | 16.3 |
| AD-264567.2 | Unknown | Unknown | Transfection | | | 12.2 | 5.2 | | | 51.5 | 18.2 |
| AD-273457.1 | Unknown | Unknown | Transfection | | | 9.6 | 3.6 | | | 48.8 | 15.4 |
| AD-273458.1 | Unknown | Unknown | Transfection | | | 14.1 | 3.5 | | | 55.2 | 17.3 |
| AD-273459.1 | Unknown | Unknown | Transfection | | | 12.0 | 4.1 | | | 58.5 | 15.0 |
| AD-273460.1 | Unknown | Unknown | Transfection | | | 13.1 | 5.3 | | | 64.2 | 12.3 |
| AD-273461.1 | Unknown | Unknown | Transfection | | | 12.0 | 3.0 | | | 52.5 | 19.2 |
| AD-273462.1 | Unknown | Unknown | Transfection | | | 13.5 | 2.5 | | | 51.3 | 25.3 |
| AD-273463.1 | Unknown | Unknown | Transfection | | | 17.7 | 6.3 | | | 57.7 | 18.0 |
| AD-273464.1 | Unknown | Unknown | Transfection | | | 11.7 | 4.1 | | | 52.7 | 23.6 |
| AD-273465.1 | Unknown | Unknown | Transfection | | | 15.0 | 6.9 | | | 67.6 | 19.2 |
| AD-273466.1 | Unknown | Unknown | Transfection | | | 12.5 | 5.9 | | | 55.8 | 7.5 |
| AD-273467.1 | Unknown | Unknown | Transfection | | | 13.8 | 2.9 | | | 62.0 | 25.5 |
| AD-273468.1 | Unknown | Unknown | Transfection | | | 10.2 | 4.2 | | | 65.5 | 16.8 |
| AD-273469.1 | Unknown | Unknown | Transfection | | | 11.4 | 1.2 | | | 44.8 | 12.5 |
| AD-273470.1 | Unknown | Unknown | Transfection | | | 14.8 | 7.2 | | | 51.3 | 11.2 |
| AD-273471.1 | Unknown | Unknown | Transfection | | | 9.3 | 2.5 | | | 43.7 | 14.0 |
| AD-273472.1 | Unknown | Unknown | Transfection | | | 11.7 | 6.1 | | | 54.0 | 7.3 |
| AD-273473.1 | Unknown | Unknown | Transfection | | | 11.0 | 3.3 | | | 48.4 | 10.7 |
| AD-273474.1 | Unknown | Unknown | Transfection | | | 14.6 | 4.5 | | | 59.4 | 8.3 |
| AD-273475.1 | Unknown | Unknown | Transfection | | | 10.5 | 4.2 | | | 47.5 | 13.9 |
| AD-273476.1 | Unknown | Unknown | Transfection | | | 10.0 | 4.1 | | | 50.8 | 5.2 |
| AD-273477.1 | Unknown | Unknown | Transfection | | | 11.9 | 1.8 | | | 74.1 | 24.2 |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-273478.1 | Unknown | Unknown | Transfection | | | 9.3 | 2.9 | | | 46.2 | 12.9 |
| AD-273479.1 | Unknown | Unknown | Transfection | | | 11.1 | 3.3 | | | 52.8 | 9.7 |
| AD-273480.1 | Unknown | Unknown | Transfection | | | 12.5 | 5.4 | | | 38.6 | 8.3 |
| AD-273481.1 | Unknown | Unknown | Transfection | | | 14.6 | 3.3 | | | 56.3 | 6.2 |
| AD-273482.1 | Unknown | Unknown | Transfection | | | 11.8 | 4.6 | | | 52.1 | 8.3 |
| AD-273483.1 | Unknown | Unknown | Transfection | | | 9.6 | 3.9 | | | 51.3 | 14.7 |
| AD-273484.1 | Unknown | Unknown | Transfection | | | 12.2 | 3.1 | | | 59.4 | 27.2 |
| AD-273485.1 | Unknown | Unknown | Transfection | | | 12.9 | 6.4 | | | 45.9 | 6.3 |
| AD-273486.1 | Unknown | Unknown | Transfection | | | 14.6 | 5.9 | | | 63.0 | 16.0 |
| AD-273487.1 | Unknown | Unknown | Transfection | | | 7.8 | 2.0 | | | 52.4 | 9.2 |
| AD-273488.1 | Unknown | Unknown | Transfection | | | 12.3 | 2.1 | | | 46.6 | 17.6 |
| AD-273489.1 | Unknown | Unknown | Transfection | | | 11.3 | 2.1 | | | 49.2 | 11.9 |
| AD-273490.1 | Unknown | Unknown | Transfection | | | 10.6 | 3.9 | | | 63.4 | 16.9 |
| AD-273491.1 | Unknown | Unknown | Transfection | | | 9.8 | 3.1 | | | 45.1 | 10.1 |
| AD-273492.1 | Unknown | Unknown | Transfection | | | 12.4 | 6.4 | | | 63.9 | 6.8 |
| AD-238841.2 | Unknown | Unknown | Transfection | | | 10.1 | 2.2 | | | 52.2 | 23.3 |
| AD-273493.1 | Unknown | Unknown | Transfection | | | 3.1 | 2.2 | | | 25.6 | 17.0 |
| AD-273494.1 | Unknown | Unknown | Transfection | | | 5.1 | 1.5 | | | 30.2 | 9.7 |
| AD-273495.1 | Unknown | Unknown | Transfection | | | 7.0 | 1.5 | | | 44.2 | 11.5 |
| AD-273496.1 | Unknown | Unknown | Transfection | | | 6.7 | 1.4 | | | 46.3 | 20.0 |
| AD-273497.1 | Unknown | Unknown | Transfection | | | 5.7 | 1.8 | | | 39.7 | 29.4 |
| AD-273498.1 | Unknown | Unknown | Transfection | | | 8.4 | 0.2 | | | 58.3 | 10.2 |
| AD-273499.1 | Unknown | Unknown | Transfection | | | 9.7 | 1.4 | | | 53.6 | 30.3 |
| AD-273500.1 | Unknown | Unknown | Transfection | | | 5.0 | 0.8 | | | 35.8 | 17.5 |
| AD-273501.1 | Unknown | Unknown | Transfection | | | 7.0 | 1.8 | | | 31.1 | 17.4 |
| AD-273502.1 | Unknown | Unknown | Transfection | | | 6.4 | 0.9 | | | 41.4 | 31.4 |
| AD-273503.1 | Unknown | Unknown | Transfection | | | 8.8 | 2.1 | | | 33.2 | 18.4 |
| AD-273504.1 | Unknown | Unknown | Transfection | | | 7.5 | 1.5 | | | 50.1 | 18.5 |
| AD-273505.1 | Unknown | Unknown | Transfection | | | 7.2 | 1.2 | | | 82.4 | 26.7 |
| AD-273506.1 | Unknown | Unknown | Transfection | | | 7.3 | 0.9 | | | 44.8 | 25.5 |
| AD-273507.1 | Unknown | Unknown | Transfection | | | 3.5 | 1.2 | | | 44.4 | 24.6 |
| AD-273508.1 | Unknown | Unknown | Transfection | | | 5.1 | 1.8 | | | 50.8 | 26.4 |
| AD-273509.1 | Unknown | Unknown | Transfection | | | 3.6 | 2.2 | | | 28.5 | 11.9 |
| AD-273510.1 | Unknown | Unknown | Transfection | | | 7.3 | 1.7 | | | 57.0 | 13.3 |
| AD-238857.2 | Unknown | Unknown | Transfection | | | 10.9 | 1.3 | | | 54.7 | 17.6 |
| AD-238858.2 | Unknown | Unknown | Transfection | | | 5.8 | 0.4 | | | 49.4 | 16.5 |
| AD-238837.2 | Unknown | Unknown | Transfection | | | 10.8 | 1.2 | | | 51.7 | 31.2 |
| AD-238859.2 | Unknown | Unknown | Transfection | | | 6.4 | 2.0 | | | 61.5 | 9.2 |
| AD-238835.2 | Unknown | Unknown | Transfection | | | 10.7 | 1.5 | | | 46.0 | 9.0 |
| AD-238860.2 | Unknown | Unknown | Transfection | | | 8.7 | 3.7 | | | 21.4 | 2.1 |
| AD-238834.2 | Unknown | Unknown | Transfection | | | 5.5 | 1.7 | | | 57.6 | 28.3 |
| AD-273511.1 | Unknown | Unknown | Transfection | | | 8.6 | 1.1 | | | 67.9 | 24.2 |
| AD-273512.1 | Unknown | Unknown | Transfection | | | 7.7 | 2.3 | | | 75.6 | 6.7 |
| AD-273513.1 | Unknown | Unknown | Transfection | | | 10.6 | 3.4 | | | 94.2 | 7.5 |
| AD-273514.1 | Unknown | Unknown | Transfection | | | 8.9 | 1.8 | | | 77.5 | 6.9 |
| AD-273515.1 | Unknown | Unknown | Transfection | | | 16.8 | 0.9 | | | 90.2 | 24.3 |
| AD-273516.1 | Unknown | Unknown | Transfection | | | 6.2 | 2.6 | | | 37.6 | 14.4 |
| AD-238854.2 | Unknown | Unknown | Transfection | | | 6.0 | 2.7 | | | 30.5 | 6.6 |
| AD-273517.1 | Unknown | Unknown | Transfection | | | 8.7 | 3.0 | | | 26.7 | 10.2 |
| AD-273518.1 | Unknown | Unknown | Transfection | | | 6.9 | 0.4 | | | 55.6 | 13.3 |
| AD-273519.1 | Unknown | Unknown | Transfection | | | 14.0 | 2.3 | | | 59.5 | 23.4 |
| AD-273520.1 | Unknown | Unknown | Transfection | | | 8.3 | 1.9 | | | 77.2 | 20.0 |
| AD-237793.2 | Unknown | Unknown | Transfection | | | 10.5 | 4.5 | | | 76.2 | 12.4 |
| AD-273521.1 | Unknown | Unknown | Transfection | | | 8.3 | 2.9 | | | 54.1 | 15.5 |
| AD-273522.1 | Unknown | Unknown | Transfection | | | 5.6 | 1.9 | | | 45.1 | 24.2 |
| AD-273523.1 | Unknown | Unknown | Transfection | | | 5.3 | 3.1 | | | 38.1 | 14.2 |
| AD-273524.1 | Unknown | Unknown | Transfection | | | 9.4 | 0.9 | | | 82.2 | 9.4 |
| AD-273525.1 | Unknown | Unknown | Transfection | | | 10.0 | 1.0 | | | 51.8 | 25.7 |
| AD-273526.1 | Unknown | Unknown | Transfection | | | 8.9 | 1.3 | | | 44.3 | 27.9 |
| AD-273527.1 | Unknown | Unknown | Transfection | | | 12.1 | 7.0 | | | 91.5 | 11.8 |
| AD-273528.1 | Unknown | Unknown | Transfection | | | 9.8 | 1.4 | | | 56.5 | 37.4 |
| AD-273529.1 | Unknown | Unknown | Transfection | | | 11.7 | 2.3 | | | 49.0 | 27.4 |
| AD-273530.1 | Unknown | Unknown | Transfection | | | 9.5 | 3.1 | | | 27.8 | 8.2 |
| AD-273531.1 | Unknown | Unknown | Transfection | | | 8.0 | 6.2 | | | 40.9 | 29.7 |
| AD-273532.1 | Unknown | Unknown | Transfection | | | 7.7 | 4.2 | | | 42.3 | 27.7 |
| AD-273533.1 | Unknown | Unknown | Transfection | | | 9.3 | 2.4 | | | 45.0 | 26.6 |
| AD-273534.1 | Unknown | Unknown | Transfection | | | 8.0 | 1.3 | | | 59.1 | 40.0 |
| AD-273535.1 | Unknown | Unknown | Transfection | | | 7.3 | 2.3 | | | 59.2 | 26.3 |
| AD-273536.1 | Unknown | Unknown | Transfection | | | 7.9 | 2.7 | | | 37.0 | 17.9 |
| AD-273537.1 | Unknown | Unknown | Transfection | | | 9.5 | 0.5 | | | 56.4 | 13.6 |
| AD-273538.1 | Unknown | Unknown | Transfection | | | 5.8 | 1.9 | | | 46.1 | 38.1 |
| AD-273539.1 | Unknown | Unknown | Transfection | | | 6.4 | 4.5 | | | 42.6 | 27.9 |
| AD-273540.1 | Unknown | Unknown | Transfection | | | 6.7 | 1.3 | | | 36.6 | 23.1 |
| AD-273541.1 | Unknown | Unknown | Transfection | | | 14.4 | 3.0 | | | 65.9 | 27.3 |
| AD-273542.1 | Unknown | Unknown | Transfection | | | 17.1 | 3.1 | | | 79.4 | 57.3 |

TABLE 2-continued

| Duplex Number | Restrictions | Cell Type | Method | % of Control 50 nM (Avg) | 50 nM (SD) | 10 nM (Avg) | 10 nM (SD) | 1 nM (Avg) | 1 nM (SD) | 0.1 nM (Avg) | 0.1 nM (SD) |
|---|---|---|---|---|---|---|---|---|---|---|---|
| AD-273543.1 | Unknown | Unknown | Transfection | | | 15.0 | 2.6 | | | 57.4 | 31.4 |
| AD-273544.1 | Unknown | Unknown | Transfection | | | 10.2 | 2.8 | | | 45.0 | 29.1 |
| AD-273545.1 | Unknown | Unknown | Transfection | | | 10.5 | 1.6 | | | 56.8 | 18.6 |
| AD-273546.1 | Unknown | Unknown | Transfection | | | 6.6 | 2.7 | | | 33.6 | 19.7 |
| AD-273547.1 | Unknown | Unknown | Transfection | | | 8.7 | 1.1 | | | 40.6 | 13.6 |
| AD-273548.1 | Unknown | Unknown | Transfection | | | 13.2 | 3.4 | | | 50.0 | 27.7 |
| AD-273549.1 | Unknown | Unknown | Transfection | | | 8.5 | 2.3 | | | 45.5 | 28.1 |
| AD-273550.1 | Unknown | Unknown | Transfection | | | 18.7 | 2.2 | | | 40.5 | 6.5 |
| AD-273551.1 | Unknown | Unknown | Transfection | | | 11.0 | 3.1 | | | 59.4 | 22.8 |
| AD-273552.1 | Unknown | Unknown | Transfection | | | 10.6 | 2.5 | | | 47.0 | 14.2 |
| AD-273553.1 | Unknown | Unknown | Transfection | | | 11.2 | 8.4 | | | 46.4 | 19.3 |
| AD-273554.1 | Unknown | Unknown | Transfection | | | 4.8 | 0.8 | | | 26.2 | 12.6 |
| AD-273555.1 | Unknown | Unknown | Transfection | | | 3.6 | 0.9 | | | 29.3 | 13.2 |
| AD-273556.1 | Unknown | Unknown | Transfection | | | 5.5 | 2.5 | | | 22.1 | 6.9 |
| AD-273557.1 | Unknown | Unknown | Transfection | | | 12.9 | 5.4 | | | 53.6 | 15.0 |
| AD-273558.1 | Unknown | Unknown | Transfection | | | 13.0 | 3.1 | | | 76.1 | 18.9 |
| AD-273559.1 | Unknown | Unknown | Transfection | | | 8.7 | 2.6 | | | 45.3 | 17.1 |
| AD-273560.1 | Unknown | Unknown | Transfection | | | 8.3 | 3.9 | | | 35.8 | 12.1 |
| AD-273561.1 | Unknown | Unknown | Transfection | | | 8.1 | 0.8 | | | 40.1 | 13.9 |
| AD-273562.1 | Unknown | Unknown | Transfection | | | 8.3 | 0.6 | | | 65.9 | 16.8 |
| AD-273563.1 | Unknown | Unknown | Transfection | | | 16.7 | 7.3 | | | 70.0 | 13.5 |
| AD-273564.1 | Unknown | Unknown | Transfection | | | 11.2 | 3.7 | | | 61.5 | 17.1 |
| AD-273565.1 | Unknown | Unknown | Transfection | | | 12.8 | 2.8 | | | 64.5 | 26.1 |
| AD-273566.1 | Unknown | Unknown | Transfection | | | 9.9 | 4.1 | | | 49.4 | 14.3 |
| AD-273567.1 | Unknown | Unknown | Transfection | | | 10.1 | 4.0 | | | 76.8 | 31.7 |
| AD-273568.1 | Unknown | Unknown | Transfection | | | 13.0 | 7.7 | | | 43.0 | 8.7 |
| AD-273569.1 | Unknown | Unknown | Transfection | | | 6.1 | 2.9 | | | 40.6 | 19.3 |
| AD-273570.1 | Unknown | Unknown | Transfection | | | 12.5 | 4.9 | | | 62.4 | 9.8 |
| AD-273571.1 | Unknown | Unknown | Transfection | | | 15.5 | 1.3 | | | 64.0 | 19.4 |
| AD-273572.1 | Unknown | Unknown | Transfection | | | 10.1 | 3.0 | | | 54.0 | 16.2 |
| AD-273573.1 | Unknown | Unknown | Transfection | | | 11.7 | 6.7 | | | 43.4 | 15.5 |
| AD-273574.1 | Unknown | Unknown | Transfection | | | 7.7 | 0.7 | | | 51.4 | 9.4 |
| AD-273575.1 | Unknown | Unknown | Transfection | | | 14.0 | 4.8 | | | 46.0 | 9.8 |
| AD-273576.1 | Unknown | Unknown | Transfection | | | 10.9 | 7.6 | | | 39.4 | 9.3 |
| AD-273577.1 | Unknown | Unknown | Transfection | | | 5.8 | 3.7 | | | 30.7 | 7.7 |
| AD-273578.1 | Unknown | Unknown | Transfection | | | 12.9 | 8.8 | | | 83.1 | 3.4 |
| AD-273579.1 | Unknown | Unknown | Transfection | | | 14.4 | 5.7 | | | 65.6 | 18.9 |
| AD-273580.1 | Unknown | Unknown | Transfection | | | 14.2 | 5.9 | | | 81.2 | 18.1 |
| AD-273581.1 | Unknown | Unknown | Transfection | | | 14.1 | 5.9 | | | 80.5 | 23.6 |
| AD-273582.1 | Unknown | Unknown | Transfection | | | 17.3 | 6.9 | | | 54.7 | 11.4 |
| AD-273583.1 | Unknown | Unknown | Transfection | | | 15.7 | 6.6 | | | 57.4 | 24.4 |
| AD-273584.1 | Unknown | Unknown | Transfection | | | 14.5 | 8.8 | | | 59.6 | 11.2 |
| AD-273585.1 | Unknown | Unknown | Transfection | | | 7.5 | 2.1 | | | 26.3 | 8.5 |
| AD-273586.1 | Unknown | Unknown | Transfection | | | 10.6 | 5.8 | | | 52.7 | 17.0 |
| AD-273587.1 | Unknown | Unknown | Transfection | | | 27.2 | 8.8 | | | 89.1 | 34.9 |
| AD-273588.1 | Unknown | Unknown | Transfection | | | 11.1 | 5.0 | | | 61.4 | 18.2 |
| AD-273589.1 | Unknown | Unknown | Transfection | | | 8.9 | 3.9 | | | 65.4 | 15.5 |
| AD-273590.1 | Unknown | Unknown | Transfection | | | 17.5 | 4.5 | | | 68.9 | 30.5 |
| AD-273591.1 | Unknown | Unknown | Transfection | | | 8.8 | 2.7 | | | 57.3 | 19.1 |
| AD-273592.1 | Unknown | Unknown | Transfection | | | 5.6 | 2.2 | | | 19.6 | 5.9 |
| AD-273593.1 | Unknown | Unknown | Transfection | | | 8.4 | 3.4 | | | 45.2 | 13.3 |
| AD-273594.1 | Unknown | Unknown | Transfection | | | 9.3 | 4.1 | | | 49.1 | 16.1 |
| AD-273595.1 | Unknown | Unknown | Transfection | | | 5.3 | 2.8 | | | 44.1 | 16.2 |
| AD-273596.1 | Unknown | Unknown | Transfection | | | 4.7 | 2.8 | | | 47.8 | 11.5 |
| AD-273597.1 | Unknown | Unknown | Transfection | | | 8.2 | 5.2 | | | 43.9 | 11.8 |
| AD-273598.1 | Unknown | Unknown | Transfection | | | 7.8 | 4.9 | | | 45.5 | 16.6 |
| AD-273599.1 | Unknown | Unknown | Transfection | | | 3.5 | 0.6 | | | 22.6 | 7.3 |
| AD-273600.1 | Unknown | Unknown | Transfection | | | 4.0 | 0.9 | | | 38.3 | 14.3 |
| AD-273601.1 | Unknown | Unknown | Transfection | | | 4.8 | 1.0 | | | 33.7 | 10.9 |
| AD-273602.1 | Unknown | Unknown | Transfection | | | 8.2 | 3.5 | | | 46.1 | 24.4 |
| AD-273603.1 | Unknown | Unknown | Transfection | | | 6.7 | 1.5 | | | 33.3 | 10.8 |
| AD-273604.1 | Unknown | Unknown | Transfection | | | 5.9 | 0.6 | | | 52.9 | 13.8 |
| AD-273605.1 | Unknown | Unknown | Transfection | | | 8.3 | 3.4 | | | 43.3 | 16.0 |
| AD-273606.1 | Unknown | Unknown | Transfection | | | 5.5 | 2.1 | | | 38.4 | 4.4 |
| AD-273607.1 | Unknown | Unknown | Transfection | | | 4.3 | 0.3 | | | 22.1 | 5.9 |
| AD-273608.1 | Unknown | Unknown | Transfection | | | 4.8 | 2.1 | | | 37.2 | 15.4 |
| AD-273609.1 | Unknown | Unknown | Transfection | | | 4.9 | 3.3 | | | 39.4 | 15.6 |
| AD-273610.1 | Unknown | Unknown | Transfection | | | 5.1 | 1.7 | | | 36.3 | 17.4 |
| AD-273611.1 | Unknown | Unknown | Transfection | | | 5.7 | 1.8 | | | 41.1 | 12.0 |
| AD-273612.1 | Unknown | Unknown | Transfection | | | 6.2 | 1.6 | | | 26.2 | 13.1 |
| AD-273613.1 | Unknown | Unknown | Transfection | | | 5.5 | 2.5 | | | 43.7 | 11.8 |
| AD-273614.1 | Unknown | Unknown | Transfection | | | 8.3 | 4.0 | | | 60.1 | 9.0 |
| AD-273615.1 | Unknown | Unknown | Transfection | | | 6.6 | 4.5 | | | 28.1 | 4.3 |
| AD-273616.1 | Unknown | Unknown | Transfection | | | 15.2 | 8.0 | | | 54.1 | 23.2 |
| AD-273617.1 | Unknown | Unknown | Transfection | | | 8.0 | 2.9 | | | 36.4 | 11.4 |

TABLE 2-continued

| | | | | % of Control | | | | | | | |
|---|---|---|---|---|---|---|---|---|---|---|---|
| Duplex Number | Restrictions | Cell Type | Method | 50 nM (Avg) | 50 nM (SD) | 10 nM (Avg) | 10 nM (SD) | 1 nM (Avg) | 1 nM (SD) | 0.1 nM (Avg) | 0.1 nM (SD) |
| AD-273618.1 | Unknown | Unknown | Transfection | | | 7.1 | 3.4 | | | 29.5 | 5.5 |
| AD-273619.1 | Unknown | Unknown | Transfection | | | 5.5 | 4.6 | | | 34.2 | 8.3 |
| AD-273620.1 | Unknown | Unknown | Transfection | | | 6.6 | 2.8 | | | 56.1 | 16.6 |
| AD-273621.1 | Unknown | Unknown | Transfection | | | 8.6 | 4.7 | | | 43.6 | 20.7 |
| AD-273622.1 | Unknown | Unknown | Transfection | | | 8.4 | 4.2 | | | 38.0 | 7.5 |
| AD-273623.1 | Unknown | Unknown | Transfection | | | 7.1 | 5.1 | | | 27.2 | 3.8 |
| AD-273624.1 | Unknown | Unknown | Transfection | | | 12.0 | 6.8 | | | 52.6 | 7.1 |
| AD-273625.1 | Unknown | Unknown | Transfection | | | 5.3 | 3.1 | | | 40.4 | 10.0 |
| AD-273626.1 | Unknown | Unknown | Transfection | | | 3.4 | 1.5 | | | 41.4 | 17.3 |
| AD-273627.1 | Unknown | Unknown | Transfection | | | 12.6 | 4.6 | | | 28.9 | 4.0 |
| AD-273628.1 | Unknown | Unknown | Transfection | | | 15.0 | 10.4 | | | 46.8 | 12.2 |
| AD-273629.1 | Unknown | Unknown | Transfection | | | 8.4 | 2.8 | | | 26.2 | 12.3 |
| AD-273630.1 | Unknown | Unknown | Transfection | | | 6.5 | 4.7 | | | 36.0 | 3.0 |

Abbreviations used in describing the sequences, e.g., sequences described in Table 1 are collected and described in Table 3 for convenience.

TABLE 3

| Abbreviation | Nucleotide(s) |
|---|---|
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |

TABLE 3-continued

| Abbreviation | Nucleotide(s) |
|---|---|
| (m5Ceos) | 2'-O-methoxyethyl-5-methylcytidine-3'-phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxyethylphosphorothioate |
| (Uhd) | 2'-O-hexadecyl-uridine-3'-phosphate |
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| Y44 | 2-hydroxymethyl-tetrahydrofurane-5-phosphate |
| Q173 | N-((GalNAc)-amidopentanoyl)-prolinol-4-phosphate (Hyp-C5-(GalNAc)) |

Example 2: Mouse In Vivo Study

AGT-Targeting duplexes in vivo: Mice (n=3/group) were treated with AAV encoding for human Angiotensinogen. At least two weeks post AAV8 dosing, mice received a single dose of siRNA (3 mg/kg). On days 1 (pretreatment), 7, 14, and 21 post-dose, blood was obtained and processed to serum. AGT levels were determined by ELISA and expressed as percent of day 1. Results are shown in FIG. 1.

Figure 2:
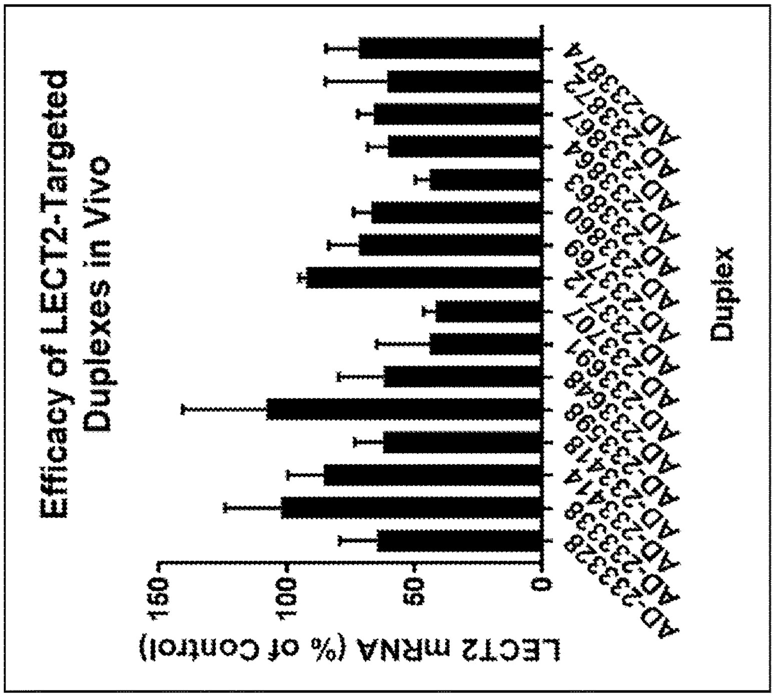

Efficacy of LECT2-targeted duplexes in vivo: Mice (n=3/group) were treated with AAV encoding for human LECT2/At least two weeks post AAV8 dosing, mice received a single dose of siRNA (2 mg/kg). On day 14 post-dose, mice were sacrificed and liver obtained. Following purification of mRNA, LECT2 levels were determined by qPCR and normalized to GAPDH. Data were then expressed as percent of PBS-treated animals. Results are ahown in FIG. 2.

Efficacy of mTTr duplexes in vivo: Mice (n=3/group) received a single dose of siRNA (1 mg/kg). On days 1 (pretreatment), 7, 14, 21, and 35 post-dose, blood was obtained and processed to serum. TTR levels were determined by ELISA and expressed as percent of day 1. Results are ahown in FIG. 3.

Figure 4:

Efficacy of ANgPTL3 duplexes in vivo: Mice (n=3/group) were treated with AAV encoding for human AngPTL3. At least two weeks post AAV8 dosing, mice received a single dose of siRNA (1 mg/kg). On days 1 and 14, blood was obtained and processed to serum. Human AngPTL3 levels were determined by ELISA and expressed as percent of day 1. Results are shown in FIG. 4.

Example 3: Non-Human Primate In Vivo Study

Figure 5:
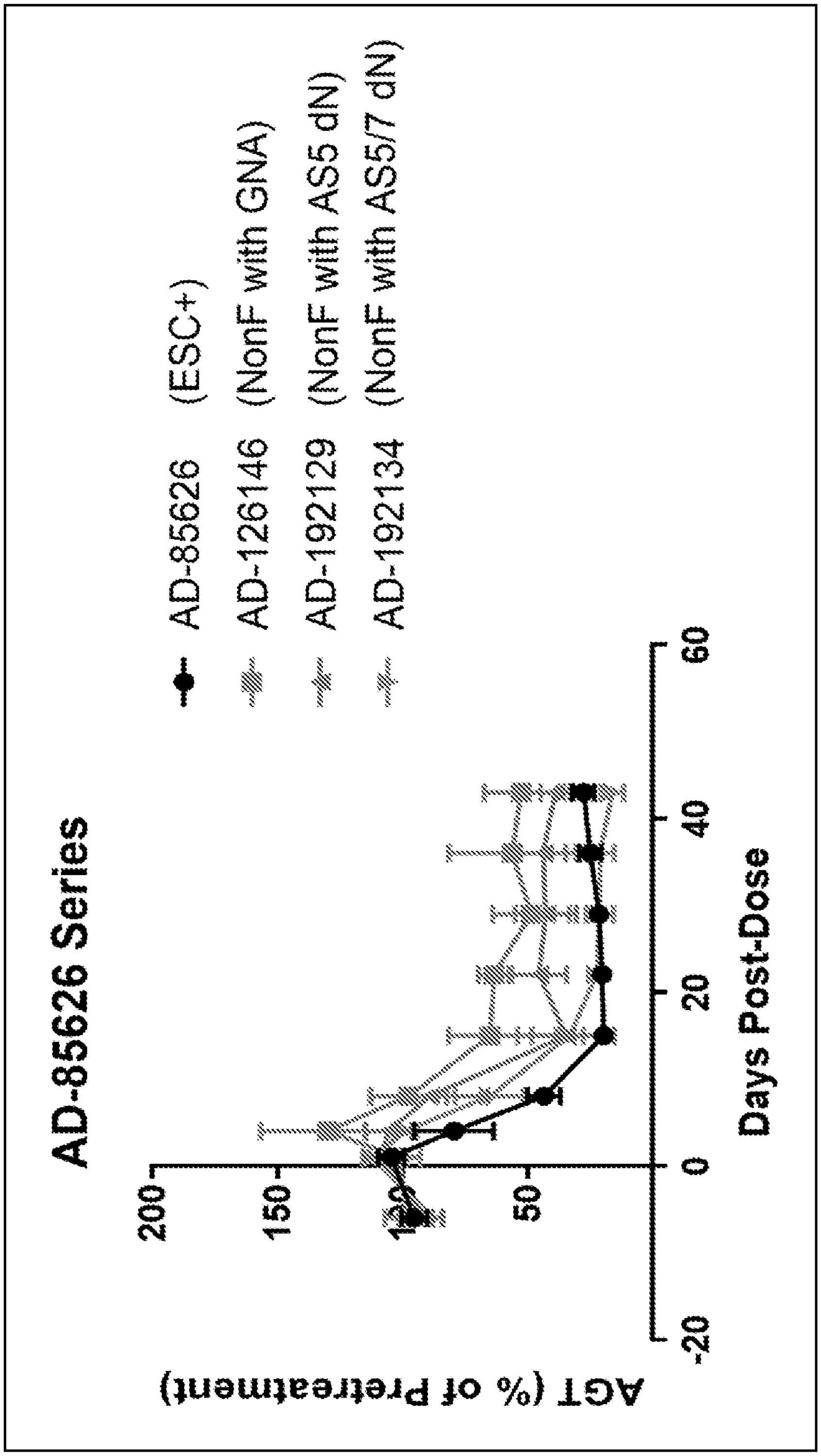
FIG. 5-8 show in vivo efficacy of some exemplary dsRNA of the invention in non-human primates.
Figure 6:
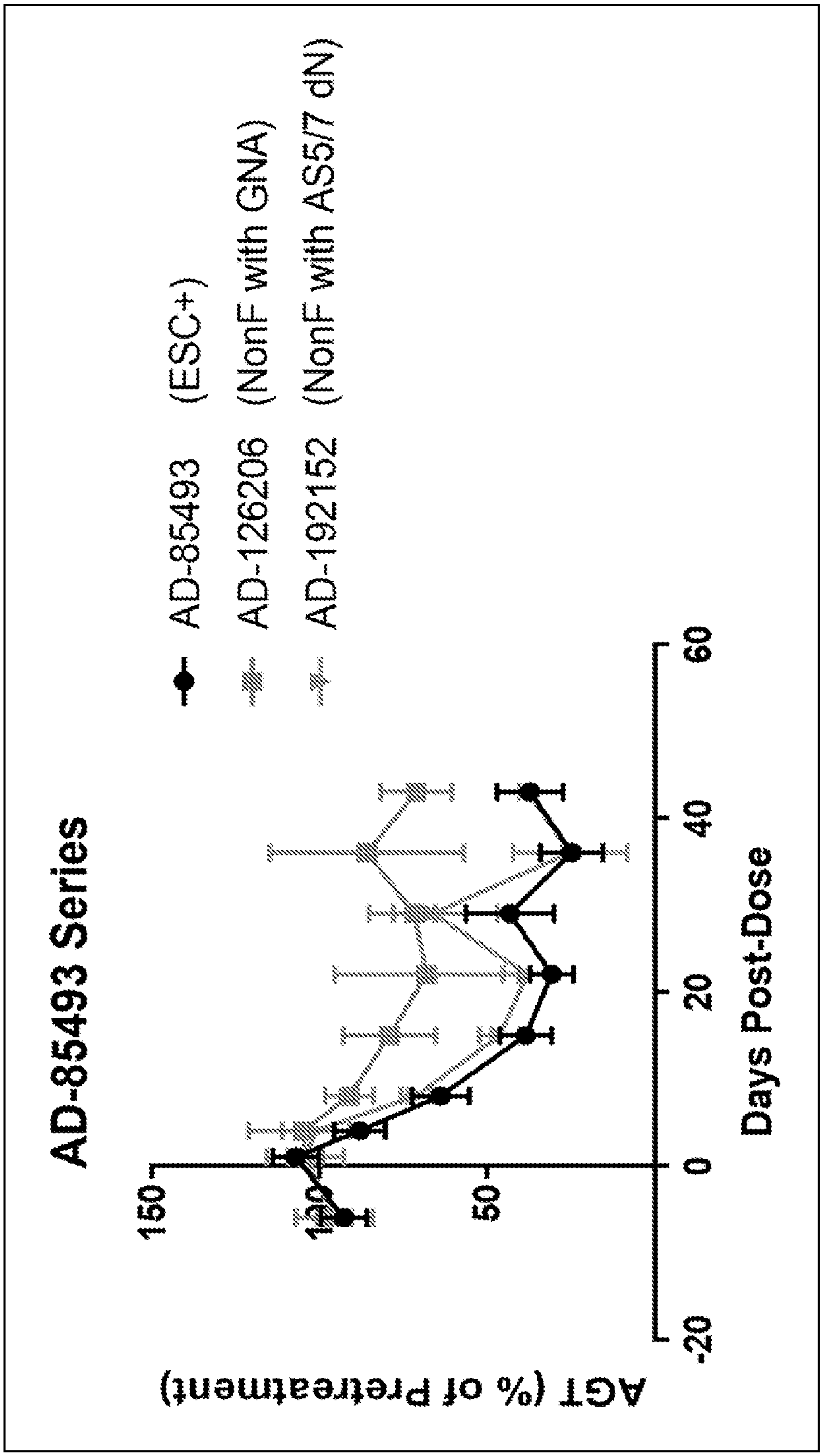

Cyno AGT: Cynomolgus monkey (n=3/group) received a single dose of siRNA (3 mg/kg). At various time-points post-dose, blood was obtained and processed to serum. AGT levels were determined by ELISA and expressed as percent of day 1. Results are shown in FIG. 5 (AD-85626 based duplexes) and FIG. 6 (AD-85493 based duplexes).

Figure 7:
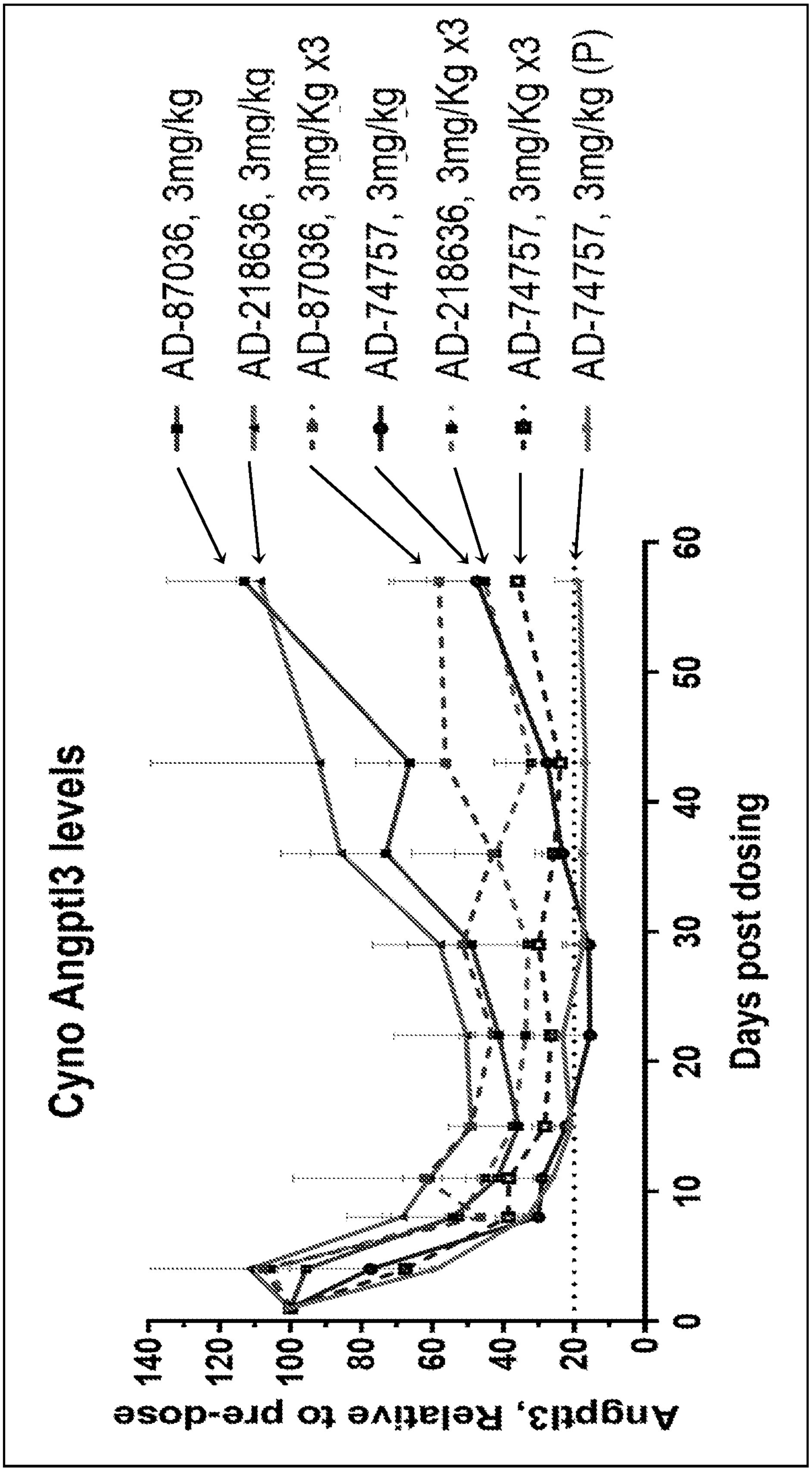

Cyno AngPTL3: In one study, cynomolgus monkey (n=3/group) received a single or multiple doses of siRNA (3 mg/kg). At various timepoints post-dose, blood was obtained and processed to serum. AngPTL3 levels were determined by ELISA and expressed as percent of day 1. Results are shown in FIG. 7.

Figure 8:
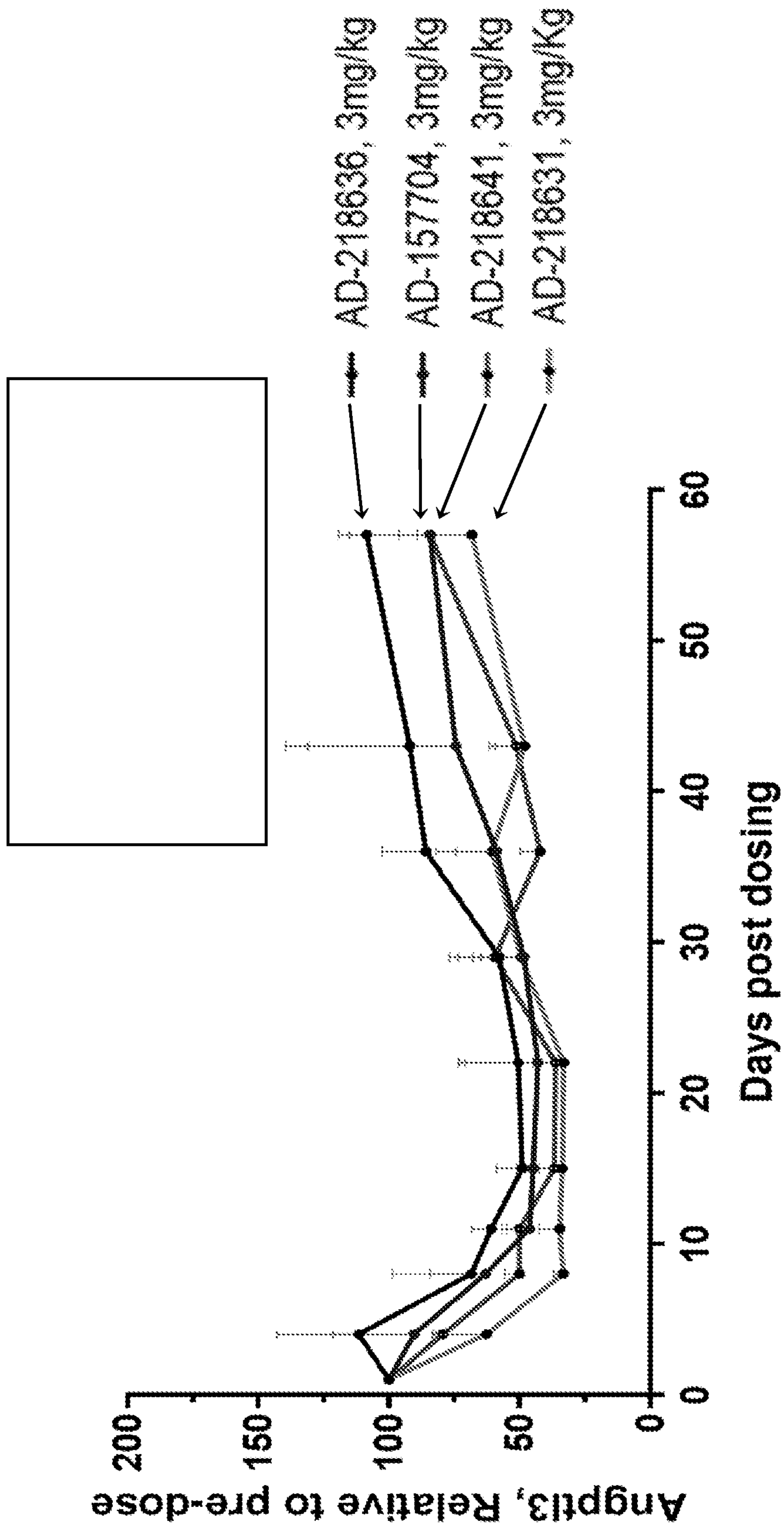

In another study, cynomolgus monkey (n=3/group) received a single dose of siRNA (3 mg/kg). At various time-points post-dose, blood was obtained and processed to serum. AGT levels were determined by ELISA and expressed as percent of day 1. Results are shown in FIG. 8.

All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A dsRNA agent comprising:

a sense strand having a length of 17-35 nucleotides;

an antisense strand having a length of 17-35 nucleotides;

at least two phosphorothioate internucleotide linkages between the first five nucleotides of the antisense strand, counting from the 5' end of the antisense strand; and only three, four, five or six 2'-deoxy modifications on the antisense strand;

wherein:

at least two 2'-deoxy modifications are in a central region of the sense strand, wherein the central region of the sense strand is positions 7, 8, 9, 10, 11, 12, and 13 counting from the 5'-end of the sense strand;

three of the 2'-deoxy modifications of the antisense strand are at positions 2, 12, and 14, counting from the 5'-end of the antisense strand;

the sense strand and the antisense strand form a duplex region containing between 17 to 25 base pairs;

the dsRNA agent comprises a ligand;

the sense strand does not comprise a glycol nucleic acid (GNA); and the 2'-deoxy modifications are not 2'-deoxy-2'-fluoro (2'-F) nucleoside.

2. The dsRNA agent of claim 1, wherein the dsRNA agents have all natural nucleotides, or less than 20% non-natural nucleotides.

3. The dsRNA agent of claim 1, wherein the dsRNA comprises a sense strand having a length of 18-30 nucleotides.

4. The dsRNA agent of claim 1, wherein the dsRNA comprises an antisense strand having a length of 18-30 nucleotides.

5. The dsRNA agent of claim 1, wherein the dsRNA comprises an antisense strand having a length of 18-23 nucleotides, and five 2'-deoxy modifications in the antisense strand at positions 2, 5, 7, 12 and 14 counting from the 5'-end of the antisense strand.

6. The dsRNA agent of claim 1, wherein at least one of the 2'-deoxy modifications is in the sense strand at position 11, counting from the 5'-end of the sense strand.

7. The dsRNA agent of claim 1, wherein at least two of the 2'-deoxy modifications are in the sense strand at positions 9 and 11 counting from the 5'-end of the sense strand.

8. The dsRNA agent of claim 1, wherein at least five of the 2'-deoxy modifications are in the antisense strand at positions 2, 5, 7, 12 and 14 counting from the 5'-end of the antisense strand, and at least two of the 2'-deoxy modifications are in the sense strand at positions 9 and 11 counting from the 5'-end of the sense strand.

9. The dsRNA agent of claim 2, wherein the non-natural nucleotide is selected from the group consisting of acyclic nucleotides, locked nucleic acid (LNA) nucleotides, hexitol nucleic acid (HNA) nucleotides, cyclohexenyl nucleic acid (CeNA) nucleotides, 2'-methoxyethyl nucleotides, 2'-O-allyl nucleotides, 2'-C-allyl nucleotides, 2'-fluoro nucleotides, 2'-O—N-methylacetamido (2'-O-NMA) nucleotides, 2'-O-dimethylaminoethoxyethyl (2'-O-DMAEOE) nucleotides, 2'-O-aminopropyl (2'-O-AP) nucleotides, and 2'-ara-F nucleotides.

10. The dsRNA agent of claim 2, wherein the natural nucleotide is selected from the group consisting of 2'-OH nucleotides, 2'-OMe nucleotides, and 2'-deoxy nucleotides.

11. The dsRNA agent of claim 1, wherein the ligand is an ASGPR ligand.

12. The dsRNA agent of claim 1, wherein:

the sense strand has:

a length of 19-25 nucleotides and only two 2'-deoxy modifications in a central region of the sense strand, wherein the central region of the sense strand is positions 7, 8, 9, 10, 11, 12 and 13, counting from 5'-end of the sense strand;

and the antisense strand has:

a length of 19-25 nucleotides, and three, four, or five 2'-deoxy modifications in the antisense strand, and wherein three of the 2'-deoxy modifications in the antisense strand are at positions 2, 12 and 14, counting from the 5'-end of the antisense strand, and wherein the duplex region contains between 17 to 25 base pairs.

13. The dsRNA agent of claim 1, wherein the dsRNA does not comprise a 2'-fluoro nucleotide.

14. The dsRNA agent of claim 1, wherein the sense strand contains only two 2'-deoxy modifications and the antisense strand contains only three, four, five or six 2'-deoxy modifications.

15. The dsRNA agent of claim 1, wherein the ligand is coupled to the 3'-end, 5'-end, and/or at an internal position of the sense strand.

16. The dsRNA agent of claim 1, wherein the ligand is a cell or tissue targeting agent.

17. The dsRNA agent of claim 16, wherein the ligand is an antibody.

18. The dsRNA agent of claim 1, wherein the ligand is an integrin receptor ligand.

19. The dsRNA agent of claim 1, wherein the ligand is a lipid or cholesterol.

20. The dsRNA agent of claim 1, comprising a two nucleotide overhang at the 3'-end of the antisense strand and a blunt end at the 5'-end of the antisense strand.

21. The dsRNA agent of claim 1, comprising blunt ends at both of the 5'-end and 3'-end of the dsRNA agent.

22. The dsRNA agent of claim 12, wherein the dsRNA agents have all natural nucleotides, or less than 20% non-natural nucleotides.

23. The dsRNA agent of claim 12, comprising a sense strand having a length of 15-17 nucleotides and an antisense strand having a length of 19-23 nucleotides.

24. The dsRNA agent of claim 22, comprising a two nucleotide overhang at the 3'-end of the antisense strand and a blunt end at the 5'-end of the antisense strand.

25. The dsRNA agent of claim 22, comprising blunt ends at both of the 5'-end and 3'-end of the dsRNA agent.

26. The dsRNA agent of claim 12, wherein five 2'-deoxy modifications in the antisense strand at positions 2, 5, 7, 12 and 14 counting from the 5'-end of the antisense strand.

27. The dsRNA agent of claim 12, wherein at least one of the 2'-deoxy modifications is in the sense strand at position 11, counting from the 5'-end of the sense strand.

28. The dsRNA agent of claim 12, wherein at least two of the 2'-deoxy modifications are in the sense strand at positions 9 and 11 counting from the 5'-end of the sense strand.

29. The dsRNA agent of claim 12, wherein five of the 2'-deoxy modifications are in the antisense strand at positions 2, 5, 7, 12 and 14 counting from the 5'-end of the antisense strand, and at least two of the 2'-deoxy modifications are in the sense strand at positions 9 and 11 counting from the 5'-end of the sense strand.

30. The dsRNA agent of claim 22, wherein the non-natural nucleotide is selected from the group consisting of acyclic nucleotides, locked nucleic acid (LNA) nucleotides, hexitol nucleic acid (HNA) nucleotides, cyclohexenyl nucleic acid (CeNA) nucleotides, 2'-methoxyethyl nucleotides, 2'-O-allyl nucleotides, 2'-C-allyl nucleotides, 2'-fluoro nucleotides, 2'-O—N-methylacetamido (2'-O-NMA) nucleotides, 2'-O-dimethylaminoethoxyethyl (2'-O-DMAEOE) nucleotides, 2'-O-aminopropyl (2'-O-AP) nucleotides, and 2'-ara-F nucleotides; and the natural nucleotide is selected from the group consisting of 2'-OH nucleotides, 2'-OMe nucleotides, and 2'-deoxy nucleotides.

31. The dsRNA agent of claim 12, wherein the ligand is an ASGPR ligand.

32. The dsRNA agent of claim 12, wherein the dsRNA does not comprise a 2'-fluoro nucleotide.

33. The dsRNA agent of claim 12, wherein the sense strand contains only two 2'-deoxy modifications and the antisense strand only contains three, four, five or six 2'-deoxy modifications.

34. The dsRNA agent of claim 12, wherein the ligand is coupled to the 3'-end, 5'-end, and/or at an internal position of the sense strand.

35. The dsRNA agent of claim 12, wherein the ligand is a cell or tissue targeting agent.

36. The dsRNA agent of claim 35, wherein the ligand is an antibody.

37. The dsRNA agent of claim 12, wherein the ligand is an integrin receptor ligand.

38. The dsRNA agent of claim 12, wherein the ligand is a lipid or cholesterol.

* * * * *

SEQUENCE LISTING

```
<160> NUMBER OF SEQ ID NOS: 964

<210> SEQ ID NO 1
<211> LENGTH: 16
<212> TYPE: PRT
<213> ORGANISM: Unknown
<220> FEATURE:
<223> OTHER INFORMATION: Description of Unknown:
      RFGF sequence

<400> SEQUENCE: 1

Ala Ala Val Ala Leu Leu Pro Ala Val Leu Leu Ala Leu Leu Ala Pro
1               5                   10                  15


<210> SEQ ID NO 2
<211> LENGTH: 11
<212> TYPE: PRT
<213> ORGANISM: Unknown
<220> FEATURE:
<223> OTHER INFORMATION: Description of Unknown:
      RFGF analogue sequence

<400> SEQUENCE: 2

Ala Ala Leu Leu Pro Val Leu Leu Ala Ala Pro
1               5                   10


<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Arg Pro Pro Gln
1               5                   10


<210> SEQ ID NO 4
<211> LENGTH: 16
<212> TYPE: PRT
<213> ORGANISM: Drosophila sp.
```

<400> SEQUENCE: 4

Arg Gln Ile Lys Ile Trp Phe Gln Asn Arg Arg Met Lys Trp Lys Lys
1 5 10 15

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 5
cuuacgcuga guacuucgat t 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 6
ucgaaguacu cagcguaagt t 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 7
gucauccaca augagaguac a 21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 8
uguactcuca utgtggauga cga 23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 9
gucauccaca augagaguac a 21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 10
uguacucuca utgtggauga cga 23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 11
gucauccaca augagaguac a 21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 12
uguacucuca utgtggauga cga 23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 13
gucauccaca augagaguac a 21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 14
ugtacucuca utgtggauga cga 23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 15
gucauccaca augagaguac a 21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 16
uguacucuca utgtggauga cga 23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 17
gucauccaca augagaguac a 21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 18
uguactcuca utgtggauga cga 23

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 19
gucauccaca augagaguac a 21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 20
uguacucuca utgtggauga cga 23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 21
gucauccaca augagaguac a 21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 22
uguacuctca utgtggauga cga 23

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 23
gucauccaca augagaguac a 21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 24
uguacucuca utgtggauga cga 23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 25
gucatccaca augagaguac a 21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 26
uguacucuca utgtggauga cga 23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 27
ucucccaccu tuucuucuaa u 21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 28
atuagaagaa aaggugggag acu 23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 29
ucucccaccu tuucuucuaa u 21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
atuagaagaa aaggugggag acu 23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
ucucccaccu tuucuucuaa u 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
attagaagaa aaggugggag acu 23

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ucucccaccu tuucuucuaa u 21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 34

atuagaagaa aaggugggag acu                                              23


<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35

ucucccaccu tuucuucuaa u                                                21


<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36

atuagaagaa aaggugggag acu                                              23


<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37

ucucccaccu tuucuucuaa u                                                21


<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38

atuagaagaa aaggugggag acu                                              23


<210> SEQ ID NO 39
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39

ucucccaccu tuucuucuaa u                                              21


<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40

atuagaagaa aaggugggag acu                                            23


<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41

ucucccaccu tuucuucuaa u                                              21


<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42

atuagaagaa aaggugggag acu                                            23


<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43

ucucccaccu tuucuucuaa u                                              21


<210> SEQ ID NO 44
<211> LENGTH: 23
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
atuagaagaa aaggugggag acu 23

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
cacaaugaga guaccuguga a 21

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
utcacaggua ctctcauugu gga 23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
cacaaugaga guaccuguga a 21

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
utcacaggua ctctcauugu gga 23

<210> SEQ ID NO 49
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
cacaaugaga guaccuguga a 21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
utcacaggua ctctcauugu gga 23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cacaaugaga guaccuguga a 21

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
utcacaggua ctctcauugu gga 23

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
cacaaugaga guaccuguga a 21

<210> SEQ ID NO 54
<211> LENGTH: 23

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 54
utcacaggua ctctcauugu gga 23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 55
cacaaugaga guaccuguga a 21

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 56
utcacaggua ctctcauugu gga 23

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 57
cacaaugaga guaccuguga a 21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 58
utcacaggua ctctcauugu gga 23

<210> SEQ ID NO 59

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 59
cacaaugaga guaccuguga a 21

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 60
utcacaggua ctctcauugu gga 23

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 61
cacaaugaga guaccuguga a 21

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 62
utcacaggua ctctcauugu gga 23

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 63
cacaaugaga guaccuguga a 21

```
<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64

utcacaggua ctctcauugu gga                                          23


<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65

ccucaacugg augaagaaac u                                            21


<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66

aguuucuca uccaguugag gga                                           23


<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67

ccucaacugg augaagaaac u                                            21


<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68

aguutcuuca uccaguugag gga                                          23
```

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 69
ccucaacugg augaagaaac u 21

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 70 aguucuuca uccaguugag gga 23

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 71
ccucaacugg augaagaaac u 21

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 72
agtutcuuca uccaguugag gga 23

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 73
ccucaacugg augaagaaac u 21

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 74
aguttcuuca uccaguugag gga 23

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 75
ccucaacugg augaagaaac u 21

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 76
aguutcuuca uccaguugag gga 23

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 77
ccucaacugg augaagaaac u 21

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 78
aguutctuca uccaguugag gga 23

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 79
ccucaacugg augaagaaac u 21

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 80
aguutcutca uccaguugag gga 23

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 81
ccucaacugg augaagaaac u 21

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 82
aguutcuuca uccaguugag gga 23

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 83

```
ccucaacugg augaagaaac u                                             21


<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84

aguucuuca uccaguugag gga                                            23


<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85

gcugagaaga tugacagguu a                                             21


<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86

uaacctguca atctucucag cag                                           23


<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87

gcugagaaga tugacagguu a                                             21


<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 88

uaaccuguca atctucucag cag                                            23


<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89

gcugagaaga tugacagguu a                                              21


<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90

uaaccuguca atctucucag cag                                            23


<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91

gcugagaaga tugacagguu a                                              21


<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92

uaaccuguca atctucucag cag                                            23


<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 93
gcugagaaga tugacagguu a 21

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 94
uaaccuguca atctucucag cag 23

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 95
gcugagaaga tugacagguu a 21

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 96
uaacctguca atctucucag cag 23

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 97
gcugagaaga tugacagguu a 21

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 98
uaaccuguca atctucucag cag 23

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 99
gcugagaaga tugacagguu a 21

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 100
uaaccugtca atctucucag cag 23

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 101
gcugagaaga tugacagguu a 21

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 102
uaaccuguca atctucucag cag 23

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
      Synthetic oligonucleotide

<400> SEQUENCE: 103
gcugagaaga tugacagguu a                                              21

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
uaaccuguca atctucucag cag                                            23

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
ucucacuutc cagcaaaacu a                                              21

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
uaguutugcu ggaaagugag acc                                            23

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
ucucacuutc cagcaaaacu a                                              21

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
Synthetic oligonucleotide

<400> SEQUENCE: 108
uagutuugcu ggaaagugag acc 23

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 109
ucucacuutc cagcaaaacu a 21

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 110
uagutuugcu ggaaagugag acc 23

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 111
ucucacuutc cagcaaaacu a 21

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 112
uagutuugcu ggaaagugag acc 23

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 113

ucucacuutc cagcaaaacu a                                              21


<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114

uagtttugcu ggaaagugag acc                                            23


<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115

ucucacuutc cagcaaaacu a                                              21


<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116

uaguttugcu ggaaagugag acc                                            23


<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117

ucucacuutc cagcaaaacu a                                              21


<210> SEQ ID NO 118
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118

uagututgcu ggaaagugag acc                                            23


<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119

ucucacuutc cagcaaaacu a                                              21


<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120

uagutuugcu ggaaagugag acc                                            23


<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121

ucucactutc cagcaaaacu a                                              21


<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122

uagutuugcu ggaaagugag acc                                            23


<210> SEQ ID NO 123
<211> LENGTH: 21
<212> TYPE: DNA
<213> ORGANISM: Artificial Sequence
```

<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 123
ucucacutuc cagcaaaacu a 21

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 124
uagutuugcu ggaaagugag acc 23

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 125
acucaauaaa gugcuuugaa a 21

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 126
utucaaagca ctutauugag uuc 23

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 127
ugcuuugagc cucagcuucu a 21

<210> SEQ ID NO 128
<211> LENGTH: 23
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
uagaagcuga ggctcaaagc acu 23

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
cccaagaaag tgaaagacca a 21

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
utggtctuuc acutucuugg gcu 23

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
ggaacucaau aaagugcuuu a 21

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
uaaagcacuu uautgaguuc cug 23

<210> SEQ ID NO 133
<211> LENGTH: 21

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 133
gcccaagaaa gugaaagacc a 21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 134
uggucutuca ctutcuuggg cuc 23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 135
agugcuuuga gccucagcuu a 21

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 136
uaagcugagg ctcaaagcac uuc 23

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 137
ucaauaaagu gcuuugaaaa u 21

<210> SEQ ID NO 138

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 138
atuutcaaag cactuuauug agu 23

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 139
gagcccaaga aagugaaaga a 21

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 140
utcutucacu utctugggcu cca 23

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 141
uggagcccaa gaaagugaaa a 21

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 142
utuucacuuu ctugggcucc aca 23

-continued

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 143
aacucaauaa agugcuuuga a 21

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 144
utcaaagcac utuauugagu ucc 23

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 145
gugcuuugag ccucagcuuc u 21

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 146
agaagctgag gcucaaagca cuu 23

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 147
uguggagccc aagaaaguga a 21

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 148
utcacutucu ugggcuccac aca 23

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 149
cucaauaaag tgcuuugaaa a 21

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 150
utuucaaagc acutuauuga guu 23

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 151
gcuuugagcc tcagcuucuc a 21

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 152
ugagaagcug aggcucaaag cac 23

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 153
guggagccca agaaagugaa a 21

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 154
utucactuuc utgggcucca cac 23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 155
ggagcccaag aaagugaaag a 21

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 156
ucuutcacuu ucutgggcuc cac 23

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 157
gaacucaata aagugcuuug a 21

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 158
ucaaagcacu utatugaguu ccu 23

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 159
ggcuguggtg accgcaacaa a 21

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 160
utugtugcgg ucaccacagc ccg 23

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 161
agcccaagaa agugaaagac a 21

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 162
uguctutcac utucuugggc ucc 23

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 163
caucagactu cucuguccaa a 21

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 164
utuggacaga gaagucugau gau 23

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 165
gugaaagacc auugcagcaa a 21

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 166
utugcugcaa uggtcuuuca cuu 23

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 167
ggaaagactc caagaaauuu a 21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 168
uaaatutcuu ggagucuuuc cau 23

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 169
ccagaagcau auugcuucau a 21

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 170
uaugaagcaa uaugcuucug gau 23

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 171
cauaacuaac caggcuuuau a 21

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 172
uauaaagccu ggutaguuau gaa 23

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 173
acauugccag aaagagaaau a 21

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 174
uauutctcuu ucuggcaaug uuu 23

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 175
gaaacucaau aaagugcuuu a 21

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 176
uaaagcacuu uautgaguuu cug 23

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 177
cacuggauau tuuugcgacu u 21

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 178
aagucgcaaa aauauccagu gua 23

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 179
acuggauatu tuugcgacuu a 21

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 180
uaagtcgcaa aaatauccag ugu 23

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 181
acuaaccagg cuuuauccuu a 21

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
      Synthetic oligonucleotide

<400> SEQUENCE: 182
uaaggataaa gcctgguuag uua                                              23

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
auuuuugcga cuuggaccuu u                                                21

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
aaagguccaa gtcgcaaaaa uau                                              23

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
cagaagcata tugcuucaua a                                                21

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
utaugaagca atatgcuucu gga                                              23

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 187
uggaaagacu ccaagaaauu u 21

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
aaautucuug gagtcuuucc aug 23

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
uacacuggau auuuuugcga a 21

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
utcgcaaaaa uauccagugu agc 23

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
gaaagacucc aagaaauuua a 21

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 192
utaaautucu uggagucuuu cca 23

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 193
uuuuugcgac tuggaccuuu a 21

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 194
uaaaggtcca agucgcaaaa aua 23

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 195
ucaauaaagu gcuuugaaaa c 21

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 196
gtuutcaaag cactuuauug agu 23

<210> SEQ ID NO 197
<211> LENGTH: 21
<212> TYPE: DNA
<213> ORGANISM: Artificial Sequence
<220> FEATURE:

<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 197
caggcuacac tggauauuuu u 21

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 198
aaaaauaucc aguguagccu gua 23

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 199
cauggaaaga cuccaagaaa u 21

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 200
atuucutgga gtctuuccau ggu 23

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 201
gacugagaag caagcgcuaa a 21

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 202
utuagcgcuu gcutcucagu cau 23

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 203
gacuccaaga aauuuaagga a 21

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 204
utccuuaaau utctuggagu cuu 23

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 205
caagaaagtg aaagaccauu a 21

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 206
uaauggtcuu ucacuuucuu ggg 23

<210> SEQ ID NO 207
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 207
acucaauaaa gugcuuugaa a 21

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 208
utucaaagca ctutauugag uuu 23

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 209
cuuccacgag aaugagcuau a 21

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 210
uauagctcau ucucguggaa gaa 23

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 211
aacuaaccag gcuuuauccu u 21

<210> SEQ ID NO 212
<211> LENGTH: 23

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
aaggauaaag ccugguuagu uau 23

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
gagucuggau cugacacuuu a 21

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
uaaaguguca gauccagacu cau 23

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
gccagaaaga gaaaugcuuu a 21

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
uaaagcauuu cucuucugg caa 23

<210> SEQ ID NO 217

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 217
ugcuuugagc cucagcuucu a 21

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 218
uagaagcuga ggctcaaagc auu 23

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 219
cuugcucuau aaaccguguu a 21

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 220
uaacacgguu uauagagcaa gaa 23

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 221
caguguuctu gcucuauaaa a 21

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 222
utuuauagag caagaacacu guu 23

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 223
ucuugcucta taaaccgugu u 21

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 224
aacacgguuu atagagcaag aac 23

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 225
guucuugctc tauaaaccgu a 21

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 226
uacggutuau agagcaagaa cac 23

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 227
uugcucuata aaccguguua a 21

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 228
utaacacggu utatagagca aga 23

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 229
aguguucutg cucuauaaac a 21

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 230
uguutataga gcaagaacac ugu 23

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 231
ccucugaugg tcaaaguccu a 21

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 232
uaggactuug accaucagag gac 23

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 233
agaacuggac accaaaucgu a 21

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 234
uacgautugg uguccaguuc uac 23

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 235
acaguguucu tgcucuauaa a 21

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 236
utuatagagc aagaacacug uuu 23

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 237
gaacuggaca ccaaaucgua a 21

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 238
utacgatuug gtgtccaguu cua 23

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 239
cucuauaaac cguguuagca a 21

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 240
utgctaacac ggutuauaga gca 23

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 241
acuggacacc aaaucguacu a 21

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 242
uaguacgauu uggtguccag uuc 23

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 243
caggaucutg ccaaagcagu a 21

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 244
uacugctuug gcaagauccu ggu 23

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 245
uguucuugcu cuauaaaccg u 21

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 246
acggtutaua gagcaagaac acu 23

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 247
cucaccacag augagaaguu u 21

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 248
aaactucuca ucugugguga gcc 23

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 249
uccucugatg gucaaagucc u 21

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 250
aggacutuga ccatcagagg aca 23

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 251
uucuugcucu auaaaccgug u 21

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 252
acacggtuua uagagcaaga aca 23

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 253
aggaucuugc caaagcagua a 21

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 254
utactgcuuu ggcaagaucc ugg 23

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 255
gcucuauaaa ccguguuagc a 21

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 256
ugcuaacacg gtutauagag caa 23

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 257
cacuacacca tcgcagcccu a 21

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 258
uagggctgcg atgguguagu ggc 23

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 259
ugcucuauaa accguguuag a 21

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 260
ucuaacacgg utuauagagc aag 23

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
      Synthetic oligonucleotide

<400> SEQUENCE: 261
ggacaccaaa tcguacugga a 21

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
utccagtacg atutgguguc cag 23

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
ccaggauctu gccaaagcag u 21

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
acugcutugg caagauccug guc 23

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
ucgccacuac accaucgcag a 21

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 266

ucugcgaugg uguaguggcg aug                                          23


<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267

cccaggagga ccaggaucuu a                                            21


<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268

uaagauccug gtccuccugg gcu                                          23


<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269

gucaaagucc tggaugcugu a                                            21


<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270

uacagcaucc aggacuuuga cca                                          23


<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: Description of Combined DNA/RNA Molecule: Synthetic oligonucleotide

<400> SEQUENCE: 271
uacaccaucg cagcccugcu a 21

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 272
uagcagggcu gcgauggugu agu 23

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 273
uggucaaagu ccuggaugcu a 21

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 274
uagcauccag gacuugacca auc 23

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 275
aaaguccugg augcuguccg a 21

<210> SEQ ID NO 276
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
ucggacagca uccaggacuu uga 23

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
cuguccgagg cagcccugcu a 21

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
uagcagggcu gcctcggaca gca 23

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
guguucuugc tcuauaaacc a 21

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
uggutuauag agcaagaaca cug 23

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 281
ugauggucaa aguccuggau a 21

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 282
uauccaggac utugaccauc aga 23

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 283
ccacuacacc aucgcagccc u 21

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 284
agggcugcga uggtguagug gcg 23

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 285
gggcucacca cagaugagaa a 21

<210> SEQ ID NO 286
<211> LENGTH: 23
<212> TYPE: DNA

-continued

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 286
utuctcaucu gtggugagcc cgu 23

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 287
accaggaucu tgccaaagca a 21

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 288
utgctutggc aagauccugg ucc 23

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 289
ccuggaugcu guccgaggca a 21

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 290
utgccucgga cagcauccag gac 23

<210> SEQ ID NO 291
<211> LENGTH: 21

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 291
ggucaaagtc cuggaugcug u 21

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 292
acagcatcca ggacuuugac cau 23

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 293
cacgggcuca ccacagauga a 21

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 294
utcatctgug gtgagcccgu gca 23

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 295
ggaucuugcc aaagcaguag a 21

<210> SEQ ID NO 296

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296

ucuacugcuu uggcaagauc cug                                          23


<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297

gcucaccaca gaugagaagu u                                            21


<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298

aacucucau ctgtggugag ccc                                           23


<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299

cucugauggu caaaguccug a                                            21


<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300

ucaggacuuu gaccaucaga gga                                          23
```

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
cuggacacca aaucguacug a 21

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
ucagtacgau utggugucca guu 23

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
cgggcucacc acagaugaga a 21

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
utcucatcug uggtgagccc gug 23

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
uggacaccaa aucguacugg a 21

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 306
uccaguacga utuggugucc agu 23

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 307
uggagagctg cacgggcuca a 21

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 308
utgagcccgu gcagcucucc aga 23

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 309
gcccaggagg accaggaucu u 21

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 310
aagatccugg ucctccuggg cug 23

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 311
ggaccaggau cuugccaaag a 21

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 312
ucuutggcaa gauccugguc cuc 23

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 313
ugcacgggcu caccacagau a 21

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 314
uauctgtggu gagcccgugc agc 23

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 315
gacaggaugg cuucccuucg a 21

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 316
ucgaagggaa gccauccugu cag 23

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 317
cgccacuaca ccaucgcagc a 21

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 318
ugcugcgaug gtgtaguggc gau 23

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 319
aaguccugga tgcuguccga a 21

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 320
utcggacagc atccaggacu uug 23

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 321
aguccuggau gcuguccgag a 21

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 322
ucucggacag cauccaggac uuu 23

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 323
cugcacgggc tcaccacaga u 21

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 324
atcuguggug agcccgugca gcu 23

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 325
gaccaggatc tugccaaagc a 21

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 326
ugcutuggca agatccuggu ccu 23

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 327
aacuggacac caaaucguac u 21

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 328
aguacgauuu gguguccagu ucu 23

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 329
gauggucaaa guccuggaug a 21

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 330
ucauccagga ctutgaccau cag 23

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 331
auggucaaag tccuggaugc u 21

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 332
agcauccagg acutugacca uca 23

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 333
gccacuacac caucgcagcc a 21

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 334
uggctgcgau gguguagugg cga 23

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 335
ugacaggatg gcuucccuuc a 21

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 336
ugaagggaag ccatccuguc agg 23

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 337
agagcugcac gggcucacca a 21

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 338
utggtgagcc cgugcagcuc ucc 23

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 339
guccuggatg cuguccgagg a 21

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
      Synthetic oligonucleotide

<400> SEQUENCE: 340
uccucggaca gcatccagga cuu 23

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
augcuguccg aggcagcccu a 21

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
uagggctgcc ucggacagca ucc 23

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
ggagagcugc acgggcucac a 21

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
ugugagcccg ugcagcucuc cag 23

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 345
cuggaugctg tccgaggcag a 21

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
ucugcctcgg acagcaucca gga 23

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
acaccaucgc agcccugcuc a 21

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
ugagcagggc ugcgauggug uag 23

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
ccaggaggac caggaucuug a 21

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 350
ucaagatccu gguccuccug ggc 23

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 351
acgggcucac cacagaugag a 21

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 352
ucucaucugu ggugagcccg ugc 23

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 353
gaucuugcca aagcaguagc a 21

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 354
ugcuactgcu utggcaagau ccu 23

<210> SEQ ID NO 355
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
ucuggagagc tgcacgggcu a 21

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
uagcccgugc agctcuccag acu 23

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
gcacgggctc accacagaug a 21

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
ucaucugugg ugagcccgug cag 23

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
uggaugcugu ccgaggcagc a 21

<210> SEQ ID NO 360
<211> LENGTH: 23
<212> TYPE: DNA
<213> ORGANISM: Artificial Sequence -continued
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
ugcugccucg gacagcaucc agg 23

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
gaugcugucc gaggcagccc u 21

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
agggcugccu cggacagcau cca 23

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
gucuggagag cugcacgggc u 21

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
agcccgtgca gcucuccaga cuc 23

<210> SEQ ID NO 365
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 365
cuggagagcu gcacgggcuc a 21

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 366
ugagcccgug cagcucucca gac 23

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 367
ggcucaccac agaugagaag u 21

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 368
acuucucauc uguggugagc ccg 23

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 369
uccuggaugc tguccgaggc a 21

<210> SEQ ID NO 370
<211> LENGTH: 23

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 370
ugcctcggac agcauccagg acu 23

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 371
ggaugcugtc cgaggcagcc a 21

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 372
uggctgccuc ggacagcauc cag 23

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 373
caggaggacc aggaucuugc a 21

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 374
ugcaagaucc uggtccuccu ggg 23

<210> SEQ ID NO 375

-continued

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 375
gagagcugca cgggcucacc a 21

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 376
uggugagccc gtgcagcucu cca 23

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 377
aacagugutc tugcucuaua a 21

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 378
utauagagca agaacacugu uuu 23

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 379
aacagugutc tugcucuaua a 21

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 380
utauagagca agaacacugu uuu 23

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 381
aacagugutc tugcucuaua a 21

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 382
utatagagca agaacacugu uuu 23

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 383
aacagugutc tugcucuaua a 21

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 384
utatagagca agaacacugu uuu 23

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 385
aacagugutc tugcucuaua a 21

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 386
utatagagca agaacacugu uuu 23

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 387
aacagugutc tugcucuaua a 21

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 388
utatagagca agaacacugu uuu 23

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 389
aacagugutc tugcucuaua a 21

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 390
utauagagca agaacacugu uuu 23

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 391
aacagugutc tugcucuaua a 21

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 392
utauagagca agaacacugu uuu 23

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 393
aacagugutc tugcucuaua a 21

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 394
utauagagca agaacacugu uuu 23

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 395
aacagugutc tugcucuaua a 21

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 396
utauagagca agaacacugu uuu 23

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 397
aacagugutc tugcucuaua a 21

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 398
utauagagca agaacacugu uuu 23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 399
aacagugutc tugcucuaua a 21

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 400
utauagagca agaacacugu uuu 23

<210> SEQ ID NO 401
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 401
aacagugutc tugcucuaua a 21

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 402
utatagagca agaacacugu uuu 23

<210> SEQ ID NO 403
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 403
aacagugutc tugcucuaua a 21

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 404
utauagagca agaacacugu uuu 23

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 405
aacagugutc tugcucuaua a 21

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 406
utauagagca agaacacugu uuu 23

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 407
aacagugutc tugcucuaua a 21

<210> SEQ ID NO 408
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 408
utatagagca agaacacugu uuu 23

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 409
aacagugutc tugcucuaua a 21

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 410
utatagagca agaacacugu uuu 23

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 411
aacagugutc tugcucuaua a 21

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 412
utatagagca agaacacugu uuu 23

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 413
aacagugutc tugcucuaua a 21

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 414
utatagagca agaacacugu uuu 23

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 415
aacagugutc tugcucuaua a 21

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 416
utauagagca agaacacugu uuu 23

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 417
aacagugutc tugcucuaua a 21

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 418
utauagagca agaacacugu uuu 23

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 419
aacagugutc tugcucuaua a 21

<210> SEQ ID NO 420
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 420
utauagagca agaacacugu uuu 23

<210> SEQ ID NO 421
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 421
aacagugutc tugcucuaua a 21

<210> SEQ ID NO 422
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 422
utauagagca agaacacugu uuu 23

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 423
aacagugutc tugcucuaua a 21

<210> SEQ ID NO 424
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule: Synthetic oligonucleotide

<400> SEQUENCE: 424
utauagagca agaacacugu uuu 23

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 425
aacagugutc tugcucuaua a 21

<210> SEQ ID NO 426
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 426
utauagagca agaacacugu uuu 23

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 427
aacagugutc tugcucuaua a 21

<210> SEQ ID NO 428
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 428
utatagagca agaacacugu uuu 23

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 429
aacagugutc tugcucuaua a 21

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 430
utauagagca agaacacugu uuu 23

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 431
aacagugutc tugcucuaua a 21

<210> SEQ ID NO 432
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 432
utatagagca agaacacugu uuu 23

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 433
aacagugutc tugcucuaua a 21

<210> SEQ ID NO 434
<211> LENGTH: 23
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 434
utatagagca agaacacugu uuu 23

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 435
aacagugutc tugcucuaua a 21

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 436
utauagagca agaacacugu uuu 23

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 437
aacagugutc tugcucuaua a 21

<210> SEQ ID NO 438
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 438
utatagagca agaacacugu uuu 23

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 439
aacagugutc tugcucuaua a 21

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 440
utauagagca agaacacugu uuu 23

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 441
aacagugutc tugcucuaua a 21

<210> SEQ ID NO 442
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 442
utauagagca agaacacugu uuu 23

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 443
aacagugutc tugcucuaua a 21

<210> SEQ ID NO 444
<211> LENGTH: 23
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 444
utauagagca agaacacugu uuu 23

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 445
aacagtgutc tugcucuaua a 21

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 446
utauagagca agaacacugu uuu 23

<210> SEQ ID NO 447
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 447
taacagugut ctugcucuau aa 22

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 448
utauagagca agaacacugu uuu 23

<210> SEQ ID NO 449
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 449
cacaaugaga guaccuguga a 21

<210> SEQ ID NO 450
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 450
utcacaggua ctctcauugu gga 23

<210> SEQ ID NO 451
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 451
cacaaugaga guaccuguga a 21

<210> SEQ ID NO 452
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 452
utcacaggua ctctcauugu gga 23

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 453
cacaaugaga guaccuguga a 21

<210> SEQ ID NO 454

<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
utcacaggua ctctcauugu gga 23

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
cacaaugaga guaccuguga a 21

<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
utcacaggua ctctcauugu gga 23

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
cacaaugaga guaccuguga a 21

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
utcacaggua ctctcauugu gga 23

```
<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459

cacaaugaga guaccuguga a                                              21


<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460

utcacaggua ctctcauugu gga                                            23


<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461

cacaaugaga guaccuguga a                                              21


<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462

utcacaggta ctctcauugu gga                                            23


<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463

cacaaugaga guaccuguga a                                              21
```

<210> SEQ ID NO 464
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 464
utcacaggua ctctcauugu gga 23

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 465
cacaaugaga guaccuguga a 21

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 466
utcacaggua ctctcauugu gga 23

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 467
cacaaugaga guaccuguga a 21

<210> SEQ ID NO 468
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 468
utcacaggua ctctcauugu gga 23

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 469
cacaaugaga guaccuguga a 21

<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 470
utcacaggua ctctcauugu gga 23

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 471
cacaaugaga guaccuguga a 21

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 472
utcacaggua ctctcauugu gga 23

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 473

-continued cacaaugaga guaccuguga a 21

<210> SEQ ID NO 474
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 474
utcacaggua ctctcauugu gga 23

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 475
cacaaugaga guaccuguga a 21

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 476
utcacaggua ctctcauugu gga 23

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 477
cacaaugaga guaccuguga a 21

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 478
utcacaggua ctctcauugu gga 23

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 479
cacaaugaga guaccuguga a 21

<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 480
utcacaggua ctctcauugu gga 23

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 481
cacaaugaga guaccuguga a 21

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 482
utcacaggua ctctcauugu gga 23

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 483
cacaaugaga guaccuguga a 21

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 484
utcacaggua ctctcauugu gga 23

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 485
cacaaugaga guaccuguga a 21

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 486
utcacaggua ctctcauugu gga 23

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 487
cacaaugaga guaccuguga a 21

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 488
utcacaggta ctctcauugu gga 23

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 489
cacaaugaga guaccuguga a 21

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 490
utcacaggua ctctcauugu gga 23

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 491
cacaaugaga guaccuguga a 21

<210> SEQ ID NO 492
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 492
utcacaggua ctctcauugu gga 23

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 493
cacaaugaga guaccuguga a 21

<210> SEQ ID NO 494
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 494
utcacaggua ctctcauugu gga 23

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 495
cacaaugaga guaccuguga a 21

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 496
utcacaggua ctctcauugu gga 23

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 497
cacaaugaga guaccuguga a 21

<210> SEQ ID NO 498
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 498
utcacaggua ctctcauugu gga 23

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 499
cacaaugaga guaccuguga a 21

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 500
utcacaggua ctctcauugu gga 23

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 501
cacaaugaga guaccuguga a 21

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 502
utcacaggua ctctcauugu gga 23

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

```
<220> FEATURE:
<223> OTHER INFORMATION: Description of Combined DNA/RNA Molecule:
      Synthetic oligonucleotide

<400> SEQUENCE: 503

cacaaugaga guaccuguga a                                              21


<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504

utcacaggua ctctcauugu gga                                            23


<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505

cacaaugaga guaccuguga a                                              21


<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506

utcacaggua ctctcauugu gga                                            23


<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507

cacaaugaga guaccuguga a                                              21


<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: Description of Combined DNA/RNA Molecule:
Synthetic oligonucleotide

<400> SEQUENCE: 508
utcacaggua ctctcauugu gga 23

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 509
cacaaugaga guaccuguga a 21

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 510
utcacaggua ctctcauugu gga 23

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 511
cacaaugaga guaccuguga a 21

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 512
utcacaggua ctctcauugu gga 23

<210> SEQ ID NO 513
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
cacaaugaga guaccuguga a 21

<210> SEQ ID NO 514
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
utcacaggua ctctcauugu gga 23

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
cacaaugaga guaccuguga a 21

<210> SEQ ID NO 516
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
utcacaggua ctctcauugu gga 23

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
cacaatgaga guaccuguga a 21

<210> SEQ ID NO 518
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 518
utcacaggua ctctcauugu gga 23

<210> SEQ ID NO 519
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 519
tcacaaugag aguaccugug aa 22

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 520
utcacaggua ctctcauugu gga 23

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 521
ucaauaaagu gcuuugaaaa u 21

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 522
atuutcaaag cactuuauug agu 23

<210> SEQ ID NO 523
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
ucaauaaagu gcuuugaaaa u 21

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
atuutcaaag cactuuauug agu 23

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
ucaauaaagu gcuuugaaaa u 21

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
atuutcaaag cactuuauug agu 23

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
ucaataaagu gcuuugaaaa u 21

<210> SEQ ID NO 528
<211> LENGTH: 23

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 528
atuutcaaag cactuuauug agu 23

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 529
ucaauaaagu gcuuugaaaa u 21

<210> SEQ ID NO 530
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 530
atuutcaaag cactuuauug agu 23

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 531
ucaauaaagu gcuuugaaaa u 21

<210> SEQ ID NO 532
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 532
atuutcaaag cactuuauug agu 23

<210> SEQ ID NO 533

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 533
ucaauaaagu gcuuugaaaa u 21

<210> SEQ ID NO 534
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 534
atuutcaaag cactuuauug agu 23

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 535
ucaauaaagu gcuuugaaaa u 21

<210> SEQ ID NO 536
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 536
atuutcaaag cactuuauug agu 23

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 537
ucaauaaagt gcuuugaaaa u 21

-continued

<210> SEQ ID NO 538
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 538
atuutcaaag cactuuauug agu 23

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 539
ucaauaaagu gcuuugaaaa u 21

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 540
atuutcaaag cactuuauug agu 23

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 541
ucaauaaagu gcuuugaaaa u 21

<210> SEQ ID NO 542
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 542
atuutcaaag cactuuauug agu 23

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 543
ucaauaaagu gcuugaaaa u 21

<210> SEQ ID NO 544
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 544
atuutcaaag cactuuauug agu 23

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 545
ucaauaaagu gcutugaaaa u 21

<210> SEQ ID NO 546
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 546
atuutcaaag cactuuauug agu 23

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 547
ucaauaaagu gcuutgaaaa u 21

<210> SEQ ID NO 548
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 548
atuutcaaag cactuuauug agu 23

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 549
ucaauaaagu gcuuugaaaa u 21

<210> SEQ ID NO 550
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 550
atuutcaaag cactuuauug agu 23

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 551
ucaauaaagu gcuuugaaaa u 21

<210> SEQ ID NO 552
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 552
atuutcaaag cactuuauug agu 23

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 553
ucaauaaagu gcuuugaaaa u 21

<210> SEQ ID NO 554
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 554
atuutcaaag cactuuauug agu 23

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 555
ucaauaaagu gcuuugaaaa u 21

<210> SEQ ID NO 556
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 556
atuutcaaag cactuuauug agu 23

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 557
ucaauaaagu gcuuugaaaa u 21

<210> SEQ ID NO 558
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 558
atuutcaaag cactuuauug agu 23

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 559
ucaauaaagu gcuuugaaaa u 21

<210> SEQ ID NO 560
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 560
attutcaaag cactuuauug agu 23

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 561
ucaauaaagu gcuuugaaaa u 21

<210> SEQ ID NO 562
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide -continued

<400> SEQUENCE: 562
atuttcaaag cactuuauug agu 23

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 563
ucaauaaagu gcuuugaaaa u 21

<210> SEQ ID NO 564
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 564
atuuucaaag cactuuauug agu 23

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 565
ucaauaaagu gcuuugaaaa u 21

<210> SEQ ID NO 566
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 566
atuutcaaag cactuuauug agu 23

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 567
ucaauaaagu gcuuugaaaa u 21

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 568
atuutcaaag cactuuauug agu 23

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 569
ucaauaaagu gcuuugaaaa u 21

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 570
atuutcaaag cactuuauug agu 23

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 571
ucaauaaagu gcuuugaaaa u 21

<210> SEQ ID NO 572
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 572
atuutcaaag cactuuauug agu 23

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 573
ucaauaaagu gcuuugaaaa u 21

<210> SEQ ID NO 574
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 574
atuutcaaag cactuuauug agu 23

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 575
ucaauaaagu gcuuugaaaa u 21

<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 576
atuutcaaag cactuuauug agu 23

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 577
ucaauaaagu gcuuugaaaa u 21

<210> SEQ ID NO 578
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 578
atuutcaaag cactuuauug agu 23

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 579
ucaauaaagu gcuuugaaaa u 21

<210> SEQ ID NO 580
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 580
atuutcaaag cactuuauug agu 23

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 581
ucaauaaagu gcuuugaaaa u 21

<210> SEQ ID NO 582
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule: Synthetic oligonucleotide

<400> SEQUENCE: 582
atuutcaaag cacuuuauug agu 23

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 583
ucaauaaagu gcuuugaaaa u 21

<210> SEQ ID NO 584
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 584
atuutcaaag cacttuauug agu 23

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 585
ucaauaaagu gcuuugaaaa u 21

<210> SEQ ID NO 586
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 586
atuutcaaag cactutauug agu 23

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 587
ucaauaaagu gcuuugaaaa u 21

<210> SEQ ID NO 588
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 588
atuutcaaag cactuuauug agu 23

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 589
ucaauaaagu gcuuugaaaa u 21

<210> SEQ ID NO 590
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 590
atuutcaaag cactuuatug agu 23

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 591
ucaauaaagu gcuuugaaaa u 21

<210> SEQ ID NO 592
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592

atuutcaaag cactuuautg agu                                              23


<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593

ucaauaaagu gcuuugaaaa u                                                21


<210> SEQ ID NO 594
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594

atuutcaaag cactuuauug agu                                              23


<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595

cucaauaaag tgcuuugaaa a                                                21


<210> SEQ ID NO 596
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596

utuucaaagc acutuauuga guu                                              23


<210> SEQ ID NO 597
<211> LENGTH: 21
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
cucaauaaag tgcuuugaaa a 21

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
utuucaaagc acutuauuga guu 23

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
cucaauaaag tgcuuugaaa a 21

<210> SEQ ID NO 600
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
utuucaaagc acutuauuga guu 23

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
cucaauaaag tgcuuugaaa a 21

<210> SEQ ID NO 602
<211> LENGTH: 23
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 602
utuucaaagc acutuauuga guu 23

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 603
cucaataaag tgcuuugaaa a 21

<210> SEQ ID NO 604
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 604
utuucaaagc acutuauuga guu 23

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 605
cucaauaaag tgcuuugaaa a 21

<210> SEQ ID NO 606
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 606
utuucaaagc acutuauuga guu 23

<210> SEQ ID NO 607
<211> LENGTH: 21

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 607
cucaauaaag tgcuuugaaa a 21

<210> SEQ ID NO 608
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 608 uuucaaagc acutuauuga guu 23

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 609
cucaauaaag tgcuuugaaa a 21

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 610 uuucaaagc acutuauuga guu 23

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 611
cucaauaaag tgcuuugaaa a 21

<210> SEQ ID NO 612

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 612
utuucaaagc acutuauuga guu 23

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 613
cucaauaaag ugcuuugaaa a 21

<210> SEQ ID NO 614
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 614
utuucaaagc acutuauuga guu 23

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 615
cucaauaaag tgcuuugaaa a 21

<210> SEQ ID NO 616
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 616
utuucaaagc acutuauuga guu 23

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 617
cucaauaaag tgcuuugaaa a 21

<210> SEQ ID NO 618
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 618
utuucaaagc acutuauuga guu 23

<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 619
cucaauaaag tgcuttgaaa a 21

<210> SEQ ID NO 620
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 620
utuucaaagc acutuauuga guu 23

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 621
cucaauaaag tgcutugaaa a 21

<210> SEQ ID NO 622
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 622
utuucaaagc acutuauuga guu 23

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 623
cucaauaaag tgcuutgaaa a 21

<210> SEQ ID NO 624
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 624
utuucaaagc acutuauuga guu 23

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 625
cucaauaaag tgcuuugaaa a 21

<210> SEQ ID NO 626
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 626
utuucaaagc acutuauuga guu 23

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 627
cucaauaaag tgcuuugaaa a 21

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 628
utuucaaagc acutuauuga guu 23

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 629
cucaauaaag tgcuuugaaa a 21

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 630
utuucaaagc acutuauuga guu 23

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 631
cucaauaaag tgcuuugaaa a 21

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 632
utuucaaagc acutuauuga guu 23

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 633
cucaauaaag tgcuuugaaa a 21

<210> SEQ ID NO 634
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 634
uttucaaagc acutuauuga guu 23

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 635
cucaauaaag tgcuuugaaa a 21

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 636
ututcaaagc acutuauuga guu 23

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 637
cucaauaaag tgcuuugaaa a 21

<210> SEQ ID NO 638
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 638
utuucaaagc acutuauuga guu 23

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 639
cucaauaaag tgcuuugaaa a 21

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 640
utuucaaagc acutuauuga guu 23

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 641
cucaauaaag tgcuuugaaa a 21

<210> SEQ ID NO 642
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 642
utuucaaagc acutuauuga guu 23

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 643
cucaauaaag tgcuuugaaa a 21

<210> SEQ ID NO 644
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 644
utuucaaagc acutuauuga guu 23

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 645
cucaauaaag tgcuuugaaa a 21

<210> SEQ ID NO 646
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 646
utuucaaagc acutuauuga guu 23

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 647
cucaauaaag tgcuuugaaa a 21

<210> SEQ ID NO 648
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 648
utuucaaagc acutuauuga guu 23

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 649
cucaauaaag tgcuuugaaa a 21

<210> SEQ ID NO 650
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 650
utuucaaagc acutuauuga guu 23

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 651
cucaauaaag tgcuuugaaa a 21

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 652
utuucaaagc acutuauuga guu 23

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 653
cucaauaaag tgcuuugaaa a 21

<210> SEQ ID NO 654
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 654
utuucaaagc acttuauuga guu 23

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 655
cucaauaaag tgcuuugaaa a 21

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 656
utuucaaagc acuuuauuga guu 23

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 657
cucaauaaag tgcuuugaaa a 21

<210> SEQ ID NO 658
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 658
utuucaaagc acuttauuga guu 23

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 659
cucaauaaag tgcuuugaaa a 21

<210> SEQ ID NO 660
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 660
utuucaaagc acutuauuga guu 23

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

```
<220> FEATURE:
<223> OTHER INFORMATION: Description of Combined DNA/RNA Molecule:
      Synthetic oligonucleotide

<400> SEQUENCE: 661

cucaauaaag tgcuuugaaa a                                              21


<210> SEQ ID NO 662
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662

utuucaaagc acutuatuga guu                                            23


<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663

cucaauaaag tgcuuugaaa a                                              21


<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664

utuucaaagc acutuautga guu                                            23


<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665

cucaauaaag tgcuuugaaa a                                              21


<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: Description of Combined DNA/RNA Molecule:
Synthetic oligonucleotide

<400> SEQUENCE: 666
utuucaaagc acutuauuga guu 23

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 667
cucaauaaag tgcuuugaaa a 21

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 668
utuucaaagc acutuauuga guu 23

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 669
aacagugutc tugcucuaua a 21

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 670
utauagagca agaacacugu uuu 23

<210> SEQ ID NO 671
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
aacagugutc tugcucuaua a 21

<210> SEQ ID NO 672
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
utauagagca agaacacugu uuu 23

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
aacagugutc tugcucuaua a 21

<210> SEQ ID NO 674
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
utauagagca agaacacugu uuu 23

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
aacagugutc tugcucuaua a 21

<210> SEQ ID NO 676
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676

utauagagca agaacacugu uuu                                    23


<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 677

aacagtgutc tugcucuaua a                                      21


<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678

utauagagca agaacacugu uuu                                    23


<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679

aacagugutc tugcucuaua a                                      21


<210> SEQ ID NO 680
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680

utauagagca agaacacugu uuu                                    23


<210> SEQ ID NO 681
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 681
aacagugttc tugcucuaua a 21

<210> SEQ ID NO 682
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 682
utauagagca agaacacugu uuu 23

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 683
aacaguguuc tugcucuaua a 21

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 684
utauagagca agaacacugu uuu 23

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 685
aacagugutc tugcucuaua a 21

<210> SEQ ID NO 686
<211> LENGTH: 23

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 686
utauagagca agaacacugu uuu 23

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 687
aacagugutc uugcucuaua a 21

<210> SEQ ID NO 688
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 688
utauagagca agaacacugu uuu 23

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 689
aacagugutc ttgcucuaua a 21

<210> SEQ ID NO 690
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 690
utauagagca agaacacugu uuu 23

<210> SEQ ID NO 691

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 691
aacagugutc tugcucuaua a 21

<210> SEQ ID NO 692
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 692
utauagagca agaacacugu uuu 23

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 693
aacagugutc tugcucuaua a 21

<210> SEQ ID NO 694
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 694
utauagagca agaacacugu uuu 23

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 695
aacagugutc tugctcuaua a 21

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 696
utauagagca agaacacugu uuu 23

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 697
aacagugutc tugcucuaua a 21

<210> SEQ ID NO 698
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 698
utauagagca agaacacugu uuu 23

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 699
aacagugutc tugcuctaua a 21

<210> SEQ ID NO 700
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 700
utauagagca agaacacugu uuu 23

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 701
aacagugutc tugcucuaua a 21

<210> SEQ ID NO 702
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 702
utauagagca agaacacugu uuu 23

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 703
aacagugutc tugcucuata a 21

<210> SEQ ID NO 704
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 704
utauagagca agaacacugu uuu 23

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 705
aacagugutc tugcucuaua a 21

<210> SEQ ID NO 706
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 706
utauagagca agaacacugu uuu 23

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 707
aacagugutc tugcucuaua a 21

<210> SEQ ID NO 708
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 708
utauagagca agaacacugu uuu 23

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 709
aacagugutc tugcucuaua a 21

<210> SEQ ID NO 710
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 710
utatagagca agaacacugu uuu 23

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 711
aacagugutc tugcucuaua a 21

<210> SEQ ID NO 712
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 712
utauagagca agaacacugu uuu 23

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 713
aacagugutc tugcucuaua a 21

<210> SEQ ID NO 714
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 714
utauagagca agaacacugu uuu 23

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 715
aacagugutc tugcucuaua a 21

<210> SEQ ID NO 716
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 716
utauagagca agaacacugu uuu 23

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 717
aacagugutc tugcucuaua a 21

<210> SEQ ID NO 718
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 718
utauagagca agaacacugu uuu 23

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 719
aacagugutc tugcucuaua a 21

<210> SEQ ID NO 720
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 720
utauagagca agaacacugu uuu 23

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 721
aacagugutc tugcucuaua a 21

<210> SEQ ID NO 722
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 722
utauagagca agaacacugu uuu 23

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 723
aacagugutc tugcucuaua a 21

<210> SEQ ID NO 724
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 724
utauagagca agaacacugu uuu 23

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 725
aacagugutc tugcucuaua a 21

<210> SEQ ID NO 726
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 726
utauagagca agaacacugu uuu 23

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 727
aacagugutc tugcucuaua a 21

<210> SEQ ID NO 728
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 728
utauagagca agaacacugu uuu 23

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 729
aacagugutc tugcucuaua a 21

<210> SEQ ID NO 730
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 730
utauagagca agaacacugu uuu 23

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 731
aacagugutc tugcucuaua a 21

<210> SEQ ID NO 732
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 732
utauagagca agaacacugu uuu 23

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 733
aacagugutc tugcucuaua a 21

<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 734
utauagagca agaacacugu uuu 23

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

-continued

<223> OTHER INFORMATION: Description of Combined DNA/RNA Molecule:
      Synthetic oligonucleotide

<400> SEQUENCE: 735
aacagugutc tugcucuaua a 21

<210> SEQ ID NO 736
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
utauagagca agaacacugu uuu 23

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
aacagugutc tugcucuaua a 21

<210> SEQ ID NO 738
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
utauagagca agaacactgu uuu 23

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
aacagugutc tugcucuaua a 21

<210> SEQ ID NO 740
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule: Synthetic oligonucleotide

<400> SEQUENCE: 740
utauagagca agaacacugu uuu 23

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 741
aacagugutc tugcucuaua a 21

<210> SEQ ID NO 742
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 742
utauagagca agaacacugt uuu 23

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 743
aguguucutg cucuauaaac a 21

<210> SEQ ID NO 744
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 744
uguutataga gcaagaacac ugu 23

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 745
agtguucutg cucuauaaac a 21

<210> SEQ ID NO 746
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 746
uguutataga gcaagaacac ugu 23

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 747
aguguucutg cucuauaaac a 21

<210> SEQ ID NO 748
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 748
uguutataga gcaagaacac ugu 23

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 749
agugtucutg cucuauaaac a 21

<210> SEQ ID NO 750
<211> LENGTH: 23
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 750
uguutataga gcaagaacac ugu 23

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 751
agugutcutg cucuauaaac a 21

<210> SEQ ID NO 752
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 752
uguutataga gcaagaacac ugu 23

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 753
aguguucutg cucuauaaac a 21

<210> SEQ ID NO 754
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 754
uguutataga gcaagaacac ugu 23

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 755
aguguucttg cucuauaaac a 21

<210> SEQ ID NO 756
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 756
uguutataga gcaagaacac ugu 23

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 757
aguguucuug cucuauaaac a 21

<210> SEQ ID NO 758
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 758
uguutataga gcaagaacac ugu 23

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 759
aguguucutg cucuauaaac a 21

<210> SEQ ID NO 760
<211> LENGTH: 23
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 760
uguutataga gcaagaacac ugu 23

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 761
aguguucutg cucuauaaac a 21

<210> SEQ ID NO 762
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 762
uguutataga gcaagaacac ugu 23

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 763
aguguucutg ctcuauaaac a 21

<210> SEQ ID NO 764
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 764
uguutataga gcaagaacac ugu 23

<210> SEQ ID NO 765
<211> LENGTH: 21

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765
aguguucutg cucuauaaac a 21

<210> SEQ ID NO 766
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766
uguutataga gcaagaacac ugu 23

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767
aguguucutg cuctauaaac a 21

<210> SEQ ID NO 768
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768
uguutataga gcaagaacac ugu 23

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769
aguguucutg cucuauaaac a 21

<210> SEQ ID NO 770

<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 770
uguutataga gcaagaacac ugu 23

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 771
aguguucutg cucuataaac a 21

<210> SEQ ID NO 772
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 772
uguutataga gcaagaacac ugu 23

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 773
aguguucutg cucuauaaac a 21

<210> SEQ ID NO 774
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 774
uguutataga gcaagaacac ugu 23

<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 775
aguguucutg cucuauaaac a 21

<210> SEQ ID NO 776
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 776
uguutataga gcaagaacac ugu 23

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 777
aguguucutg cucuauaaac a 21

<210> SEQ ID NO 778
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 778
uguutataga gcaagaacac ugu 23

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 779
aguguucutg cucuauaaac a 21

<210> SEQ ID NO 780
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 780
uguutataga gcaagaacac ugu 23

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 781
aguguucutg cucuauaaac a 21

<210> SEQ ID NO 782
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 782
ugtutataga gcaagaacac ugu 23

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 783
aguguucutg cucuauaaac a 21

<210> SEQ ID NO 784
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 784
uguttataga gcaagaacac ugu 23

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 785
aguguucutg cucuauaaac a 21

<210> SEQ ID NO 786
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 786
uguuuataga gcaagaacac ugu 23

<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 787
aguguucutg cucuauaaac a 21

<210> SEQ ID NO 788
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 788
uguutataga gcaagaacac ugu 23

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 789

-continued aguguucutg cucuauaaac a 21

<210> SEQ ID NO 790
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 790
uguutauaga gcaagaacac ugu 23

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 791
aguguucutg cucuauaaac a 21

<210> SEQ ID NO 792
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 792
uguutataga gcaagaacac ugu 23

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 793
aguguucutg cucuauaaac a 21

<210> SEQ ID NO 794
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 794
uguutataga gcaagaacac ugu 23

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 795
aguguucutg cucuauaaac a 21

<210> SEQ ID NO 796
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 796
uguutataga gcaagaacac ugu 23

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 797
aguguucutg cucuauaaac a 21

<210> SEQ ID NO 798
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 798
uguutataga gcaagaacac ugu 23

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 799
aguguucutg cucuauaaac a 21

<210> SEQ ID NO 800
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 800
uguutataga gcaagaacac ugu 23

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 801
aguguucutg cucuauaaac a 21

<210> SEQ ID NO 802
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 802
uguutataga gcaagaacac ugu 23

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 803
aguguucutg cucuauaaac a 21

<210> SEQ ID NO 804
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 804
uguutataga gcaagaacac ugu 23

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 805
aguguucutg cucuauaaac a 21

<210> SEQ ID NO 806
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 806
uguutataga gcaagaacac ugu 23

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 807
aguguucutg cucuauaaac a 21

<210> SEQ ID NO 808
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 808
uguutataga gcaagaacac ugu 23

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 809
aguguucutg cucuauaaac a 21

<210> SEQ ID NO 810
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 810
uguutataga gcaagaacac ugu 23

<210> SEQ ID NO 811
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 811
aguguucutg cucuauaaac a 21

<210> SEQ ID NO 812
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 812
uguutataga gcaagaacac ugu 23

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 813
aguguucutg cucuauaaac a 21

<210> SEQ ID NO 814
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 814
uguutataga gcaagaacac ugu 23

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 815
aguguucutg cucuauaaac a 21

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 816
uguutataga gcaagaacac ugu 23

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 817
ugacaaaata acucacuaua a 21

<210> SEQ ID NO 818
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 818
utauagtgag utatuuuguc aau 23

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 819
ugacaaaata acucacuaua a 21

<210> SEQ ID NO 820
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820
utauagtgag utatuuuguc aau 23

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 821
ugacaaaata acucacuaua a 21

<210> SEQ ID NO 822
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 822
utauagtgag utatuuuguc aau 23

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 823
ugacaaaata acucacuaua a 21

<210> SEQ ID NO 824
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 824
utauagtgag utatuuuguc aau 23

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 825
ugacaaaata acucacuaua a 21

<210> SEQ ID NO 826
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 826
utauagtgag utatuuuguc aau 23

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 827
ugacaaaata acucacuaua a 21

<210> SEQ ID NO 828
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 828
utauagtgag utatuuuguc aau 23

<210> SEQ ID NO 829
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829
ugacaaaata acucacuaua a 21

<210> SEQ ID NO 830
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
utauagtgag utatuuuguc aau 23

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 831
ugacaaaaua acucacuaua a 21

<210> SEQ ID NO 832
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 832
utauagtgag utatuuuguc aau 23

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 833
ugacaaaata acucacuaua a 21

<210> SEQ ID NO 834
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 834
utauagtgag utatuuuguc aau 23

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 835
ugacaaaata acucacuaua a 21

<210> SEQ ID NO 836
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 836
utauagtgag utatuuuguc aau 23

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 837
ugacaaaata acucacuaua a 21

<210> SEQ ID NO 838
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 838
utauagtgag utatuuuguc aau 23

<210> SEQ ID NO 839
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 839
ugacaaaata actcacuaua a 21

<210> SEQ ID NO 840
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 840
utauagtgag utatuuuguc aau 23

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 841
ugacaaaata acucacuaua a 21

<210> SEQ ID NO 842
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 842
utauagtgag utatuuuguc aau 23

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 843
ugacaaaata acucacuaua a 21

<210> SEQ ID NO 844
<211> LENGTH: 23

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 844
utauagtgag utatuuuguc aau 23

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 845
ugacaaaata acucacuaua a 21

<210> SEQ ID NO 846
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 846
utauagtgag utatuuuguc aau 23

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 847
ugacaaaata acucactaua a 21

<210> SEQ ID NO 848
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 848
utauagtgag utatuuuguc aau 23

<210> SEQ ID NO 849

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 849
ugacaaaata acucacuaua a 21

<210> SEQ ID NO 850
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 850
utauagtgag utatuuuguc aau 23

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 851
ugacaaaata acucacuata a 21

<210> SEQ ID NO 852
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 852
utauagtgag utatuuuguc aau 23

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 853
ugacaaaata acucacuaua a 21

<210> SEQ ID NO 854
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 854
utauagtgag utatuuuguc aau 23

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 855
ugacaaaata acucacuaua a 21

<210> SEQ ID NO 856
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 856
utauagtgag utatuuuguc aau 23

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 857
ugacaaaata acucacuaua a 21

<210> SEQ ID NO 858
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 858
utatagtgag utatuuuguc aau 23

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 859
ugacaaaata acucacuaua a 21

<210> SEQ ID NO 860
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 860
utauagtgag utatuuuguc aau 23

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 861
ugacaaaata acucacuaua a 21

<210> SEQ ID NO 862
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 862
utauagtgag utatuuuguc aau 23

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 863
ugacaaaata acucacuaua a 21

<210> SEQ ID NO 864
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 864
utauagugag utatuuuguc aau 23

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 865
ugacaaaata acucacuaua a 21

<210> SEQ ID NO 866
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 866
utauagtgag utatuuuguc aau 23

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 867
ugacaaaata acucacuaua a 21

<210> SEQ ID NO 868
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 868
utauagtgag utatuuuguc aau 23

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 869
ugacaaaata acucacuaua a 21

<210> SEQ ID NO 870
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 870
utauagtgag utatuuuguc aau 23

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 871
ugacaaaata acucacuaua a 21

<210> SEQ ID NO 872
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 872
utauagtgag ttatuuuguc aau 23

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 873
ugacaaaata acucacuaua a 21

<210> SEQ ID NO 874
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 874
utauagtgag uuatuuuguc aau 23

<210> SEQ ID NO 875
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 875
ugacaaaata acucacuaua a 21

<210> SEQ ID NO 876
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 876
utauagtgag utatuuuguc aau 23

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 877
ugacaaaata acucacuaua a 21

<210> SEQ ID NO 878
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 878
utauagtgag utauuuuguc aau 23

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 879
ugacaaaata acucacuaua a 21

<210> SEQ ID NO 880
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 880
utauagtgag utattuuguc aau 23

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 881
ugacaaaata acucacuaua a 21

<210> SEQ ID NO 882
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 882
utauagtgag utatutuguc aau 23

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 883
ugacaaaata acucacuaua a 21

<210> SEQ ID NO 884
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 884
utauagtgag utatuutguc aau 23

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 885
ugacaaaata acucacuaua a 21

<210> SEQ ID NO 886
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 886
utauagtgag utatuuuguc aau 23

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 887
ugacaaaata acucacuaua a 21

<210> SEQ ID NO 888
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 888
utauagtgag utatuuugtc aau 23

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 889
ugacaaaata acucacuaua a 21

<210> SEQ ID NO 890
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 890
utauagtgag utatuuuguc aau 23

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 891
aagcaagata tuuuuauaau a 21

<210> SEQ ID NO 892
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 892
uauuauaaaa atatcuugcu uuu 23

<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 893
aagcaagata tuuuuauaau a 21

<210> SEQ ID NO 894
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 894
uauuauaaaa atatcuugcu uuu 23

<210> SEQ ID NO 895
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 895
aagcaagata tuuuuauaau a 21

<210> SEQ ID NO 896
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 896
uauuauaaaa atatcuugcu uuu 23

<210> SEQ ID NO 897
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 897
aagcaagata tuuuuauaau a 21

<210> SEQ ID NO 898
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 898
uauuauaaaa atatcuugcu uuu 23

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 899
aagcaagata tuuuuauaau a 21

<210> SEQ ID NO 900
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 900
uauuauaaaa atatcuugcu uuu 23

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 901
aagcaagata tuuuuauaau a 21

<210> SEQ ID NO 902
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 902
uauuauaaaa atatcuugcu uuu 23

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 903
aagcaagata tuuuuauaau a 21

<210> SEQ ID NO 904
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 904
uauuauaaaa atatcuugcu uuu 23

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 905
aagcaagaua tuuuuauaau a 21

<210> SEQ ID NO 906
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 906
uauuauaaaa atatcuugcu uuu 23

<210> SEQ ID NO 907
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 907
aagcaagata tuuuuauaau a 21

<210> SEQ ID NO 908
<211> LENGTH: 23
<212> TYPE: DNA
<213> ORGANISM: Artificial Sequence
<220> FEATURE:

<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 908
uauuauaaaa atatcuugcu uuu 23

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 909
aagcaagata uuuuuauaau a 21

<210> SEQ ID NO 910
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 910
uauuauaaaa atatcuugcu uuu 23

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 911
aagcaagata ttuuuauaau a 21

<210> SEQ ID NO 912
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 912
uauuauaaaa atatcuugcu uuu 23

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 913
aagcaagata tutuuauaau a 21

<210> SEQ ID NO 914
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 914
uauuauaaaa atatcuugcu uuu 23

<210> SEQ ID NO 915
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 915
aagcaagata tuutuauaau a 21

<210> SEQ ID NO 916
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 916
uauuauaaaa atatcuugcu uuu 23

<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 917
aagcaagata tuuutauaau a 21

<210> SEQ ID NO 918
<211> LENGTH: 23
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 918
uauuauaaaa atatcuugcu uuu 23

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 919
aagcaagata tuuuuauaau a 21

<210> SEQ ID NO 920
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 920
uauuauaaaa atatcuugcu uuu 23

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 921
aagcaagata tuuuuataau a 21

<210> SEQ ID NO 922
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 922
uauuauaaaa atatcuugcu uuu 23

<210> SEQ ID NO 923
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 923
aagcaagata tuuuuauaau a 21

<210> SEQ ID NO 924
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 924
uauuauaaaa atatcuugcu uuu 23

<210> SEQ ID NO 925
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 925
aagcaagata tuuuuauaau a 21

<210> SEQ ID NO 926
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 926
uauuauaaaa atatcuugcu uuu 23

<210> SEQ ID NO 927
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 927
aagcaagata tuuuuauaat a 21

<210> SEQ ID NO 928

<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 928
uauuauaaaa atatcuugcu uuu 23

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 929
aagcaagata tuuuuauaau a 21

<210> SEQ ID NO 930
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 930
uatuauaaaa atatcuugcu uuu 23

<210> SEQ ID NO 931
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 931
aagcaagata tuuuuauaau a 21

<210> SEQ ID NO 932
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 932
uautauaaaa atatcuugcu uuu 23

<210> SEQ ID NO 933
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 933
aagcaagata tuuuuauaau a 21

<210> SEQ ID NO 934
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 934
uauuauaaaa atatcuugcu uuu 23

<210> SEQ ID NO 935
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 935
aagcaagata tuuuuauaau a 21

<210> SEQ ID NO 936
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 936
uauuataaaa atatcuugcu uuu 23

<210> SEQ ID NO 937
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 937
aagcaagata tuuuuauaau a 21

<210> SEQ ID NO 938
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 938
uauuauaaaa atatcuugcu uuu 23

<210> SEQ ID NO 939
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 939
aagcaagata tuuuuauaau a 21

<210> SEQ ID NO 940
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 940
uauuauaaaa atatcuugcu uuu 23

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 941
aagcaagata tuuuuauaau a 21

<210> SEQ ID NO 942
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 942
uauuauaaaa atatcuugcu uuu 23

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 943
aagcaagata tuuuuauaau a 21

<210> SEQ ID NO 944
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 944
uauuauaaaa atatcuugcu uuu 23

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 945
aagcaagata tuuuuauaau a 21

<210> SEQ ID NO 946
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 946
uauuauaaaa atatcuugcu uuu 23

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 947
aagcaagata tuuuuauaau a 21

<210> SEQ ID NO 948
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 948
uauuauaaaa auatcuugcu uuu 23

<210> SEQ ID NO 949
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 949
aagcaagata tuuuuauaau a 21

<210> SEQ ID NO 950
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 950
uauuauaaaa atatcuugcu uuu 23

<210> SEQ ID NO 951
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 951
aagcaagata tuuuuauaau a 21

<210> SEQ ID NO 952
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 952
uauuauaaaa ataucuugcu uuu 23

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 953
aagcaagata tuuuuauaau a 21

<210> SEQ ID NO 954
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 954
uauuauaaaa atatcuugcu uuu 23

<210> SEQ ID NO 955
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 955
aagcaagata tuuuuauaau a 21

<210> SEQ ID NO 956
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 956
uauuauaaaa atatctugcu uuu 23

<210> SEQ ID NO 957
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 957
aagcaagata tuuuuauaau a 21

<210> SEQ ID NO 958
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 958
uauuauaaaa atatcutgcu uuu 23

<210> SEQ ID NO 959
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 959
aagcaagata tuuuuauaau a 21

<210> SEQ ID NO 960
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 960
uauuauaaaa atatcuugcu uuu 23

<210> SEQ ID NO 961
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 961
aagcaagata tuuuuauaau a 21

<210> SEQ ID NO 962
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide -continued

```
<400> SEQUENCE: 962

uauuauaaaa atatcuugcu uuu                                              23


<210> SEQ ID NO 963
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 963

aagcaagata tuuuuauaau a                                                21


<210> SEQ ID NO 964
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 964

uauuauaaaa atatcuugct uuu                                              23
```